US008119680B2

(12) United States Patent
Cheng et al.

(10) Patent No.: US 8,119,680 B2
(45) Date of Patent: Feb. 21, 2012

(54) α-HALOKETONE DERIVATIVES OF IMIDAZOLYL-SUBSTITUTED AROMATIC COMPOUNDS AND COMPOUNDS PREPARED THEREFROM

(75) Inventors: Soan Cheng, San Diego, CA (US); Daniel D Comer, Spring Valley, CA (US); Long Mao, San Diego, CA (US); Guity P Balow, Fallbrook, CA (US); David Pleynet, San Diego, CA (US)

(73) Assignee: Neurogenetic Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 12/875,935

(22) Filed: Sep. 3, 2010

(65) Prior Publication Data
US 2010/0331551 A1 Dec. 30, 2010

Related U.S. Application Data

(62) Division of application No. 11/765,397, filed on Jun. 19, 2007, now Pat. No. 7,799,808, which is a division of application No. 10/846,941, filed on May 14, 2004, now Pat. No. 7,244,739.

(60) Provisional application No. 60/532,260, filed on Dec. 22, 2003, provisional application No. 60/470,884, filed on May 14, 2003.

(51) Int. Cl.
*A61K 31/415* (2006.01)
*C07D 233/54* (2006.01)

(52) U.S. Cl. .................................. 514/399; 548/341.1
(58) Field of Classification Search .................. 514/399; 548/341.1
See application file for complete search history.

(56) References Cited

U.S. PATENT DOCUMENTS

| | | | |
|---|---|---|---|
| 3,710,795 A | 1/1973 | Higuchi et al. |
| RE28,819 E | 5/1976 | Thompson |
| 4,044,126 A | 8/1977 | Cook et al. |
| 4,328,245 A | 5/1982 | Yu et al. |
| 4,358,603 A | 11/1982 | Yu |
| 4,364,923 A | 12/1982 | Cook et al. |
| 4,409,239 A | 10/1983 | Yu |
| 4,410,545 A | 10/1983 | Yu et al. |
| 4,414,209 A | 11/1983 | Cook et al. |
| 4,766,213 A | 8/1988 | Juraszyk et al. |
| 5,033,252 A | 7/1991 | Carter |
| 5,052,558 A | 10/1991 | Carter |
| 5,323,907 A | 6/1994 | Kalvelage |
| 5,387,742 A | 2/1995 | Cordell |
| 5,594,010 A | 1/1997 | Fey et al. |
| 5,612,486 A | 3/1997 | McConlogue et al. |
| 5,672,805 A | 9/1997 | Neve |
| 5,709,874 A | 1/1998 | Hanson et al. |
| 5,759,542 A | 6/1998 | Gurewich |
| 5,811,633 A | 9/1998 | Wadsworth et al. |
| 5,840,674 A | 11/1998 | Yatvin et al. |
| 5,850,003 A | 12/1998 | McLonlogue et al. |
| 5,860,957 A | 1/1999 | Jacobsen et al. |
| 5,900,252 A | 5/1999 | Calanchi et al. |
| 5,948,433 A | 9/1999 | Burton et al. |
| 5,972,366 A | 10/1999 | Haynes et al. |
| 5,983,134 A | 11/1999 | Ostrow |
| 5,985,307 A | 11/1999 | Hanson et al. |
| 5,985,317 A | 11/1999 | Venkateshwaran et al. |
| 6,004,534 A | 12/1999 | Langer et al. |
| 6,010,715 A | 1/2000 | Wick et al. |
| 6,024,975 A | 2/2000 | D'Angelo et al. |
| 6,037,521 A | 3/2000 | Sato et al. |
| 6,039,975 A | 3/2000 | Shah et al. |
| 6,048,736 A | 4/2000 | Kosak |
| 6,060,082 A | 5/2000 | Chen et al. |
| 6,071,495 A | 6/2000 | Unger et al. |
| 6,120,751 A | 9/2000 | Unger |
| 6,131,570 A | 10/2000 | Schuster et al. |
| 6,139,865 A | 10/2000 | Friend et al. |
| 6,167,301 A | 12/2000 | Flower et al. |
| 6,184,435 B1 | 2/2001 | Benson et al. |
| 6,187,797 B1 | 2/2001 | Pruitt et al. |
| 6,187,992 B1 | 2/2001 | Zheng et al. |
| 6,211,428 B1 | 4/2001 | Singh et al. |
| 6,253,872 B1 | 7/2001 | Neumann |
| 6,256,533 B1 | 7/2001 | Yuzhakov et al. |
| 6,261,595 B1 | 7/2001 | Stanley et al. |
| 6,267,983 B1 | 7/2001 | Fujii et al. |
| 6,271,359 B1 | 8/2001 | Norris et al. |
| 6,274,552 B1 | 8/2001 | Tamarkin et al. |
| 6,316,652 B1 | 11/2001 | Steliou |
| 6,340,783 B1 | 1/2002 | Snow |
| 6,562,817 B1 | 5/2003 | Tanimoto et al. |
| 2003/0158199 A1 | 8/2003 | Stieber et al. |

FOREIGN PATENT DOCUMENTS

| | | |
|---|---|---|
| EP | 0 219 436 | 4/1987 |
| EP | 1 052 238 A1 | 11/2000 |
| JP | 62-181277 | 8/1987 |
| JP | 01-143856 | 6/1989 |
| JP | 04-276551 | 10/1992 |
| JP | 07-048369 | 2/1995 |
| JP | 2002-531503 | 6/2000 |

(Continued)

OTHER PUBLICATIONS

Lubisch et al. CAS: 135: 166828, 2001.* Mishina et al. CAS: 123:83361, 1995.*
Canadian Office Action dated Jun. 29, 2010 for Application No. 2525547.
Dhar et al., A Survey of Cyclic Replacements for the Central Diamide Moiety of Inhibitors of Inosine Monophosphate Dehydrogenase. Bioorganic & Medicinal Chemistry Letters, 12:3125-3128 (2002).
Emilien et al., Prospects for Pharmacological Intervention in Alzheimer Disease, Arch Neuro., 57:176-181 (2000).

(Continued)

*Primary Examiner* — Rei-tsang Shiao
(74) *Attorney, Agent, or Firm* — Foley & Lardner LLP; Stephen E. Reiter

(57) ABSTRACT

Novel compounds, compositions, and kits are provided. Methods of modulating Aβ levels, and methods of treating a disease associated with aberrant Aβ levels are also provided.

25 Claims, No Drawings

FOREIGN PATENT DOCUMENTS

| | | |
|---|---|---|
| JP | 2001-114690 | 4/2001 |
| JP | 2002-121597 | 4/2002 |
| JP | 2002-531504 | 9/2002 |
| JP | 2003-313176 A | 11/2003 |
| JP | 2004-516507 | 6/2004 |
| JP | 2006-500325 | 1/2006 |
| WO | WO-97/36898 | 10/1997 |
| WO | WO-99/38829 | 8/1999 |
| WO | WO-00/33841 | 6/2000 |
| WO | WO-00/33842 | 6/2000 |
| WO | WO-01/87845 | 11/2001 |
| WO | WO-02/50591 | 6/2002 |
| WO | WO-02/083667 | 10/2002 |
| WO | WO-03/007955 | 1/2003 |
| WO | WO-03/032916 | 4/2003 |
| WO | WO-2004/002480 | 1/2004 |
| WO | WO-2004/016997 | 3/2004 |
| WO | WO-2004/046120 | 6/2004 |

OTHER PUBLICATIONS

European Search Report dated Nov. 7, 2007 for EP Application No. 04752297.4.

Examination Report dated Jan. 30, 2006 for SG Application No. 200507305-1.

Examiner's Report dated Oct. 15, 2009 for AU Application No. 2004247013.

Games et al., Alzheimer-type neuropathology in transgenic mice overexpressing V717F β-amyloid precursor protein, Nature 373:523-527 (1995).

Hampel et al, Synthese einiger 2-Alkylamino- und 2-Arylamino-4-aryl-thiazole. Journal fur Praktische Chemie, 1968, 38(5-6):320-326.

Harris et al., Discovery and evaluation of 2-Anilino-5-aryloxazoles as a novel class of VEGFR2 kinase inhibitors, Journal of Medicinal Chemistry, Web release Feb. 9, 2005.

International Search Report and Written Opinion dated Dec. 20, 2004 for PCT Application No. PCT/US04/15239.

Japanese Office Action dated Jun. 1, 2010 for Application No. 2006-533094, English Translation.

Joshi et al., Synthesis of Some Substituted Pyrazoles as Possible Antibacterial Agents, J. Indian Chem. Soc., vol. LIV, pp. 1081-1083 (1977).

Joshua et al, Interaction of Thiocarbamides with α-Bromoketones: Formation of Substituted 2-Aminothiazoles, Indian Journal of Chemistry, 1973, 11(2):118-119.

Klunk et al., Imaging Aβ Plaques in Living Transgenic Mice with Multiphoton Microscopy and Methoxy-X04, a Systematically Administered Congo Red Derivative, J. Neuropathol. Exp. Neurol., 61:797-805 (2002).

Mathis et al., A Lipophilic Thioflavin-T Derivative for Positron emission tomography (PET) Imaging of Amyloid in Brain, Bioorg. Med. Chem. Lett., 12:295-298 (2002).

Nagatomi et al., Studies on the Anti-inflammatory Activity and Ulcerogenic Adverse Effect of Thiazole Derivatives, Especially 2-Amino-thiazoleacetic Acid Derivatives, Arzneiittel-Forschung Druq Research, 1984, 34(5):599-603.

Neve et al., Transgenic Mice Expressing APP-C100 in the Brain, Neurobiol. Aging, 17:191-203 (1996).

Office Action dated Sep. 22, 2006 for IN Application No. 4753/DELNP/2005.

Pruitt et al., CAS: 134:375528 (2001).

Reddy et al, Activity of Acryloyl Thaiazoles, Thiazolyl Aminopyrimidines and Thiazolyl Thiopyrmidines on *Aspergillus flavus* Link, ex Fries In Vitro, Indian Bot. Reptr 4(2):144-147 (1985).

Schumann et al, Synthesis and Characterization of Some Heterocyclic Analogues of N.N'-Perarylated Phenylen-1,4-diamines and Benzidines as a New Class of Hole Transport materials, Synthesis, 2002, No. 9, pp. 1268-1276.

US Notice of Allowance dated Feb. 6, 2007 for U.S. Appl. No. 10/846,841.

US Notice of Allowance dated Apr. 16, 2010 for U.S. Appl. No. 11/779,249.

US Notice of Allowance dated May 5, 2010 for U.S. Appl. No. 11/765,397.

US Office Action dated May 22, 2009 for U.S. Appl. No. 11/779,249.
US Office Action dated Jun. 18, 2009 for U.S. Appl. No. 11/765,397.
US Office Action dated Oct. 16, 2006 for U.S. Appl. No. 10/846,941.
US Office Action dated Dec. 2, 2009 for U.S. Appl. No. 11/779,249.
US Office Action dated Dec. 30, 2009 for U.S. Appl. No. 11/765,397.

Wiltfang et al., Elevation of β-Amyloid Peptide 2-42 in Sporadic and Familial Alzheimer's Disease and Its Generation in PS1 Knockout Cells, J. Biol. Chem., 276:42645-42657 (2001).

Written Opinion dated May 2, 2007 for SG App. No. 200507305-1.
Written Opinion dated Jul. 4, 2006 for SG App. No. 200507305-1.
Official Action for European Application No. 04752297.4 dated Nov. 30, 2010.

US Notice of Allowance dated Apr. 29, 2011 in U.S. Appl. No. 12/861,782.

* cited by examiner

ən# α-HALOKETONE DERIVATIVES OF IMIDAZOLYL-SUBSTITUTED AROMATIC COMPOUNDS AND COMPOUNDS PREPARED THEREFROM

RELATED APPLICATIONS

This application is a divisional of U.S. application Ser. No. 11/765,397, filed Jun. 19, 2007 which is a divisional of U.S. patent application Ser. No. 10/846,941, filed May 14, 2004 which claims the benefit of U.S. Provisional Application No. 60/470,884, filed May 14, 2003, and U.S. Provisional Application No. 60/532,260, filed Dec. 22, 2003, the entire contents of each of which are incorporated herein by reference.

FIELD OF THE INVENTION

Compounds, pharmaceutical compositions, and methods of use of the compounds are provided. In one embodiment, the compounds are useful in treatment of neurodegenerative diseases.

BACKGROUND OF THE INVENTION

The information provided herein and references cited are provided solely to assist the understanding of the reader, and does not constitute an admission that any of the references or information is prior art to the present invention.

Neurodegenerative diseases are disorders characterized by destruction or deterioration of selective neuronal populations. Exemplary neurodegenerative diseases include Alzheimer's disease (AD), Parkinsonian syndromes such as (PD), Huntington's disease (HD), Prion diseases, cerebral amyloid angiopathy (CAA), and mild cognitive impairment (MCI). Neurodegenerative disease is associated with progressive nervous system dysfunction, and often leads to atrophy of affected central or peripheral nervous system structures.

Alzheimer's disease (AD) is a progressive neurodegenerative disorder that is the predominant cause of dementia in people over 65 years of age. Clinical symptoms of the disease begin with subtle short-term memory problems. As the disease progresses, difficulty with memory, language and orientation worsen to the point of interfering with the ability of the person to function independently. Other symptoms, which are variable, include myoclonus and seizures. Duration of AD from the first symptoms of memory loss until death is 10 years on average.

AD is characterized by massive neuronal cell loss in certain brain areas, and by the deposition of proteinaceous material in the brains of AD patients. These deposits contain neurofibrillary tangles and β-amyloid plaques. The major protein component of the β-amyloid plaque is Aβ.

Increased accumulation of Aβ has been postulated to significantly contribute to the pathogenesis of AD, and is also associated with various other amyloidoses and neurological disorders, such as Parkinson's disease, Down syndrome, diffuse Lewy body disease, progressive supranuclear palsy, and Hereditary Cerebral Hemorrhage with Amyloidosis-Dutch Type (HCHWA-D), cerebral amyloid angiopathy (CAA), and mild cognitive impairment (MCI). Support for a role for Aβ in AD can be found in Down patients who develop AD-like symptoms and pathology after age 40. Such patients exhibit AD-like amyloid plaques prior to the onset of other AD symptoms, suggesting that increased amyloid accumulation is an initial pathogenic event. Additional evidence implicating accumulation of Aβ peptides in AD comes from the identification of various mutations that result in increased formation of Aβ by cells that account for certain types of inherited AD (familial AD, or FAD). FAD individuals comprise 10% of all AD cases and generally exhibit symptoms of the disease much earlier than sporadic AD patients.

Aβ peptides are derived from processing of an amyloid precursor protein (APP). mRNA generated from the APP gene on chromosome 21 undergoes alternative splicing to yield about 10 possible isoforms, three of which (APP695, 751, and 770 amino acid isoforms) predominate in the brain. APP695 is the shortest of the three isoforms and is produced mainly in neurons. APP751, which contains a Kunitz-protease inhibitor (KPI) domain, and APP770, which contains both the KPI domain and an MRC-OX2 antigen domain, are found mostly in non-neuronal glial cells.

The major APP isoforms are single-transmembrane proteins, composed of an extracellular amino-terminal domain (approximately 590-680 amino acids) and a cytoplasmic tail containing intracellular trafficking signals (approximately 55 amino acids). Within APP, the Aβ peptide sequence is located partially on the extracellular side of the membrane and extends partially into the transmembrane region. APP isoforms 695, 751, and 770 share the same Aβ, transmembrane, and intracellular domains.

APP is trafficked through the constitutive secretory pathway, where it undergoes post-translational processing, including cleavage via two pathways: an amyloidogenic pathway and a non-amyloidogenic pathway. In the non-amyloidogenic pathway, APP is cleaved by α-secretase within the Aβ domain, releasing a large soluble N-terminal fragment (sAPPα) for secretion and a non-amyloidogenic C-terminal fragment (C83). Because cleavage occurs within the Aβ domain, α-secretase cleavage in the non-amyloidogenic pathway precludes Aβ formation. The C-terminal fragment of APP generated by α-secretase cleavage (C83) is subsequently cleaved by γ-secretase within the predicted transmembrane domain to generate a non-amyloidogenic peptide fragment termed p3 (22-24 residues).

In the amyloidogenic pathway, APP is cleaved by β-secretase (BACE1 or BACE2 enzymes) at the beginning of the Aβ domain that defines the amino terminus of the Aβ peptide. Cleavage by BACE1 or BACE2 generates a shorter soluble N-terminus, sAPPβ, as well as an amyloidogenic C-terminal fragment (C99). Alternatively, BACE1 can also cleave APP 10 amino acids after the beginning of the Aβ domain (between amino acid 10 and 11) to generate a longer N-terminal soluble fragment and a shorter C-terminal fragment (C89). Additional cleavage of either C89 or C99 by γ-secretase, a presenilin-dependent enzyme, produces Aβ peptides of various lengths.

The predominant forms of Aβ found in plaques from AD brains are the Aβ42 and Aβ40 species. Aβ42 is the species initially deposited in brain plaques, and is highly prone to aggregation in vitro. Therefore, the Aβ42 species of amyloid peptide, in particular, may be a viable target in the development of therapeutics for the treatment of disease or disorders characterized by Aβ accumulation.

Currently, there is no cure or effective treatment for AD, and the few approved drugs, including Aricept, Exelon, Cognex and Reminyl, are palliative at best. Based on the correlation between Aβ accumulation, neuronal loss and AD, modulating Aβ levels, such as reducing levels of pathogenic Aβ species, represents a viable way to decrease plaque formation and minimize neuronal cell death. Thus, there exists a medical need for compounds that modulate levels of Aβ, Indeed, such compounds would be useful for the treatment of neurodegenerative disorders, such as AD.

SUMMARY OF THE INVENTION

In accordance with the present invention, novel compounds have been discovered that are useful in the treatment of a variety of diseases. Compositions and kits comprising novel compounds are also presented.

An aspect of the invention provides compounds which have activity in modulating levels of amyloid-beta (Aβ). As a result, such compounds are applicable for treating diseases associated with aberrant levels of Aβ and/or any condition in which modulation of Aβ levels provides a therapeutic effect. Preferably, compounds herein are useful in the treatment of neurodegenerative disorders, such as AD.

DETAILED DESCRIPTION OF THE INVENTION

Unless defined otherwise, all technical and scientific terms used herein have the same meaning as is commonly understood by one of ordinary skill in the art to which this invention belongs. All patents, applications, published applications and other publications are incorporated by reference in their entirety.

I. Invention Compounds

The present invention provides novel compounds having a structure corresponding to Formula (I):

(I)

and pharmaceutically acceptable salts, and prodrugs thereof, wherein:

A is:

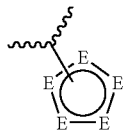

wherein each E is independently N, NR, C, $CR^1$, S, or O provided that no more than four E's are heteroatoms;

R is hydrogen, substituted or unsubstituted alkyl, substituted or unsubstituted alkenyl, substituted or unsubstituted alkynyl, substituted or unsubstituted alkoxy, substituted or unsubstituted alkylamido, substituted or unsubstituted alkylamino, substituted or unsubstituted cycloalkyl, or substituted or unsubstituted aryl;

each $R^1$ is independently hydrogen, halogen, substituted or unsubstituted alkyl, substituted or unsubstituted alkenyl, substituted or unsubstituted alkynyl, substituted or unsubstituted alkoxy, substituted or unsubstituted alkylamido, substituted or unsubstituted alkylamino, substituted or unsubstituted amino, substituted or unsubstituted cycloalkyl, or substituted or unsubstituted aryl;

or A is:

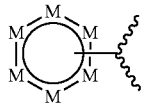

wherein each M is independently selected from $CR^1$ or N, provided that no more than three M's are N; and B is:

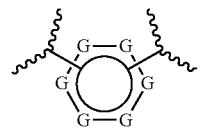

wherein each G is independently $CR^2$ or N, provided that no more than three G's are N;

each $R^2$ is independently selected from hydrogen, halogen, substituted or unsubstituted alkyl, substituted or unsubstituted alkenyl, substituted or unsubstituted alkynyl, substituted or unsubstituted alkoxy, substituted or unsubstituted alkylamido, substituted or unsubstituted alkylamino, substituted or unsubstituted amino;

or B, together with A, forms a fused ring system;

C is:

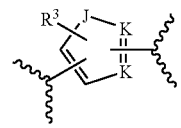

wherein J is selected from the group consisting of $CR^3$, O, S, N, and NR;

each K is independently N, NR, C, or $CR^3$;

each $R^3$ is independently hydrogen, halogen, substituted or unsubstituted alkyl, substituted or unsubstituted cycloalkyl, substituted or unsubstituted aryl, substituted or unsubstituted heteroaryl, or substituted or unsubstituted alkoxy, with a proviso that when C is

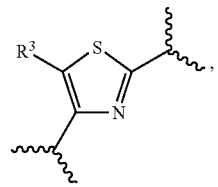

$R^3$ is not —$NH_2$;

or C is:

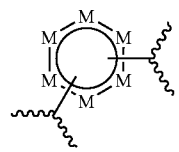

wherein each M is independently selected from $CR^1$ or N, provided that no more than three M's are N;

D is:

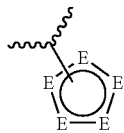

wherein each E is independently N, NR, C, CR¹, S, or O provided that no more than four E's are heteroatoms; or D is:

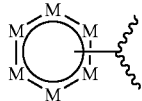

wherein each M is independently selected from $CR^5$ or N, provided that no more than three M's are N;

each $R^5$ is independently selected from hydrogen, halogen, substituted or unsubstituted alkyl, substituted or unsubstituted alkenyl, substituted or unsubstituted alkynyl, substituted or unsubstituted alkoxy, substituted or unsubstituted cycloalkyl, substituted or unsubstituted heterocycle, substituted or unsubstituted aryl, substituted or unsubstituted heteroaryl, or substituted or unsubstituted amino, or substituted or unsubstituted alkylamino;

$L_A$ is optional, and when present, is a covalent bond or a linker selected from the group consisting of —C=C—, —C≡C—, —(C(R')₂)$_z$—, —O—, —O—(C(R')₂)$_z$—, —S—, —NR'—, —NH—(C(R')₂)$_z$—, —N=N—, —C(O)—, —C(O)NR'—, —O—C(O)—, —O—C(O)—O—, —O—C(O)—NR'—, —NR'—C(O)—, —NR'—C(O)—O—, —NR'—C(O)—NR'—, —S—C(O)—, —S—C(O)—O—, —S—C(O)—NR'—, —S(O)—, —S(O)₂—, —O—S(O)₂—, —O—S(O)₂—O—, —O—S(O)₂—NR'—, —O—S(O)—, —O—S(O)—O—, —O—S(O)—NR'—, —O—NR'—C(O)—, —O—NR'—C(O)—O—, —O—NR'—C(O)—NR'—, —NR'—O—C(O)—, —NR'—O—C(O)—O—, —NR'—O—C(O)—NR'—, —O—NR'—C(S)—, —O—NR'—C(S)—O—, —O—NR'—C(S)—NR'—, —NR'—O—C(S)—, —NR'—O—C(S)—O—, —NR'—O—C(S)—NR'—, —O—C(S)—, —O—C(S)—O—, —O—C(S)—NR'—, —NR'—C(S)—, —NR'—C(S)—O—, —NR'—C(S)—NR'—, —S—S(O)₂—, —S—S(O)₂—O—, —S—S(O)₂—NR'—, —NR'—O—S(O)—, —NR'—O—S(O)—O—, —NR'—O—S(O)—NR'—, —NR'—O—S(O)₂—, —NR'—O—S(O)₂—O—, —NR'—O—S(O)₂—NR'—, —O—NR'—S(O)—, —O—NR'—S(O)—O—, —O—NR'—S(O)—NR'—, —O—NR'—S(O)₂—O—, —O—NR'—S(O)₂—NR'—, —O—NR'—S(O)₂—, —O—P(O)(R')₂—, —S—P(O)(R')₂—, and —NR'—P(O)(R')₂—, wherein each R' is independently hydrogen, substituted or unsubstituted alkyl, substituted or unsubstituted alkenyl, substituted or unsubstituted alkynyl, or substituted or unsubstituted cycloalkyl, and z is 1-10;

$L_B$ is independently a covalent bond or a linker selected from the group consisting of —C=C—, —C≡C—, —(C(R')₂)$_z$—, —O—, —O—(C(R')₂)$_z$—, —S—, —NR'—NH—(C(R')₂)$_z$—, —N=N—, —C(O)—, —C(O)NR'—, —O—C(O)—, —O—C(O)—O—, —O—C(O)—NR'—, —NR'—C(O)—, —NR'—C(O)—(O)—, —NR'—C(O)—NR'—, —S—C(O)—, —S—C(O)—O—, —S—C(O)—NR'—, —S(O)—, —S(O)₂—, —O—S(O)₂—, —O—S(O)₂—O—, —O—S(O)₂—NR'—, —O—S(O)—, —O—S(O)—O—, —O—S(O)—NR'—, —O—NR'—C(O)—, —O—NR'—C(O)—O—, —O—NR'—C(O)—NR'—, —NR'—O—C(O)—, —NR'—O—C(O)—O—, —NR'—O—C(O)—NR'—, —O—NR'—C(S)—, —O—NR'—C(S)—O—, —O—NR'—C(S)—NR'—, —NR'—O—C(S)—, —NR'—O—C(S)—O—, —NR'—O—C(S)—NR'—, —O—C(S)—, —O—C(S)—O—, —O—C(S)—NR'—, —NR'—C(S)—, —NR'—C(S)—O—, —NR'—C(S)—NR'—, —S—S(O)₂—, —S—S(O)₂—O—, —S—S(O)₂—NR'—, —NR'—O—S(O)—, —NR'—O—S(O)—O—, —NR'—O—S(O)—NR'—, —NR'—O—S(O)₂—, —NR'—O—S(O)₂—O—, —NR'—O—S(O)₂—NR'—, —O—NR'—S(O)—, —O—NR'—S(O)—O—, —O—NR'—S(O)—NR'—, —O—NR'—S(O)₂—O—, —O—NR'—S(O)₂—NR'—, —O—NR'—S(O)₂—, —O—P(O)(R')₂—, —S—P(O)(R')₂—, and —NR'—P(O)(R')₂—, wherein each R' is independently hydrogen, substituted or unsubstituted alkyl, substituted or unsubstituted alkenyl, substituted or unsubstituted alkynyl, or substituted or unsubstituted cycloalkyl, and z is 1-10;

$L_C$ is —O—, —S—, —S(O)—, —S(O)₂—, —NR—, —C(O)—, —(C(R')$_z$—, or —C(S)—;

with a proviso that when A is

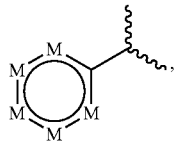

$L_A$ is not —C(O)NH—, —CH₂NH—, —CH₂—O—, or —C(O)N(CH₃)—; and said compound of Formula (I) is not

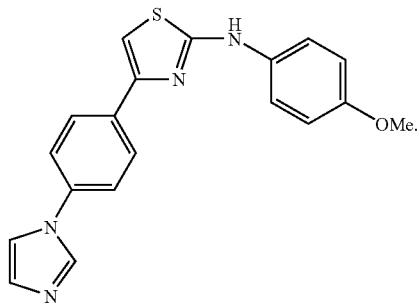

As used herein, reference to a certain element such as hydrogen or H is meant to include all isotopes of that element. For instance, if a group is defined to include hydrogen or H, it also can include deuterium and/or tritium. In the structures provided herein, where a nitrogen atom appears to be divalent, it is assumed that the nitrogen atom is trivalent and the third substituient is hydrogen.

Compounds of the present invention may have asymmetric centers and may occur, except when specifically noted, as mixtures of stereoisomers or as individual diastereomers, or enantiomers, with all isomeric forms being included in the present invention. Compounds of the present invention embrace all conformational isomers. Compounds of the present invention may also exist in one or more tautomeric forms, including both single tautomers and mixtures of tautomers.

The phrase "hydrocarbyl" refers to any organic radical having a directly attachable carbon atom to any molecule presented herein, The phrase "substituted hydrocarbyl" refers to a hydrocarbyl group that is substituted according to the definition provided below. Hydrocarbyl groups include saturated and unsaturated hydrocarbons, straight and branched chain aliphatic hydrocarbons, cyclic hydrocarbons, and aromatic hydrocarbons.

The phrase "substituted" refers to an atom or group of atoms that has been replaced with another substituent. The phrase "substituted" includes any level of substitution, e.g. mono-, di-, tri-, tetra-, or penta-substitution, where such substitution is chemically permissible. Substitutions can occur at any chemically accessible position and on any atom, such as substitution(s) on carbons or any heteroatom. For example, substituted compounds are those where one or more bonds to a hydrogen or carbon atom(s) contained therein are replaced by a bond to non-hydrogen and/or non-carbon atom(s).

The phrase "alkyl" refers to hydrocarbyl chains comprising from 1 to 20 carbon atoms. The phrase "alkyl" includes straight chain alkyl groups, such as methyl, ethyl, propyl, butyl, pentyl, hexyl, heptyl, octyl, nonyl, decyl, undecyl, dodecyl, and the like. The phrase also includes branched chain isomers of straight chain alkyl groups, including but not limited to, the following which are provided by way of example: —CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH$_3$)CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, —CH$_2$CH$_2$C(CH$_2$CH$_3$)$_3$, —CH(CH$_3$)CH$_2$CH(CH$_3$)$_2$, —CH(CH$_3$)CH(CH$_3$)CH(CH$_3$)$_2$, and —CH(CH$_2$CH$_3$)CH(CH$_3$)CH(CH$_3$)(CH$_2$CH$_3$). Thus, alkyl groups include primary alkyl groups, secondary alkyl groups, and tertiary alkyl groups. Preferred alkyl groups include alkyl groups having from 1 to 16 carbon atoms, or from 1 to 3 carbon atoms, such as methyl, ethyl, propyl, and —CH(CH$_3$)$_2$.

The phrase "substituted alkyl" refers to an alkyl group that is substituted according to the definition provided above. Examples of "substituted alkyl" groups include, but are not limited to, replacements of carbon or hydrogen atom(s) with a halogen atom(s), such as trifluoromethyl; an oxygen atom(s) in groups such as hydroxyl groups, alkoxy groups, aryloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, N-alkyloxides, imides, and enamines; a silicon atom in groups such as in trialkylsilyl groups, dialkylarylsilyl groups, alkyldiarylsilyl groups, and triarylsilyl groups; and other various heteroatoms. Additionally, substituted alkyl groups may be bonded to one or more carbon atom(s).

The phrase "alkenyl" refers to hydrocarbyl chains comprising from 2 to 20 carbon atoms and comprising at least one carbon-carbon double bond (—C═C—). The phrase "alkenyl" includes straight chain alkenyl groups, as well as branched chain isomers of straight chain alkenyl groups. Preferably, alkenyl groups comprise from 1 to 8 double bond(s). The phrase "substituted alkenyl" refers to an alkenyl group that is substituted according to the definition provided above.

The phrase "alkynyl" refers to hydrocarbyl chains comprising from 2 to 20 carbon atoms and comprising at least one carbon-carbon triple bond (—C≡C—). The phrase "alkynyl" includes straight chain alkynyl groups, as well as branched chain isomers of straight chain alkynyl groups. Preferably, alkynyl groups comprise from 1 to 8 triple bond(s). The phrase "substituted alkynyl" refers to an alkynyl group that is substituted according to the definition provided above.

The phrase "cycloalkyl" refers to an alicyclic moiety having 3 to 20 carbon atoms and comprising any chemically permissible amount of saturated or unsaturated bonds. Preferably, cycloalkyl groups comprise from 4 to 7 carbons atoms. Cycloalkyl groups include, but are not limited to, cyclopropyl, cyclobutyl, cyclopentyl, cyclohexyl, cycloheptyl, cyclooctyl, and the like. The phrase "substituted cycloalkyl" refers to a cycloalkyl group that is substituted according to the definition provided above. Substituted cycloalkyl groups can have one or more atom substituted with straight or branched chain alkyl groups and can further comprise cycloalkyl groups that are substituted with other rings including fused rings. Examples of cycloalkyl groups that are substituted with fused rings include, but are not limited to, adamantyl, norbornyl, bicyclo[2.2.2]octyl, decalinyl, tetrahydronaphthyl, and indanyl, bornyl, camphenlyl, isocamphenyl, and carenyl groups. Representative substituted cycloalkyl groups may be mono-substituted or substituted more than once, such as, but not limited to, 2,2-, 2,3-, 2,4-, 2,5-, or 2,6-disubstituted cyclohexyl groups or mono-, di- or tri-substituted norbornyl or cycloheptyl groups, which may be substituted with, for example, alkyl, alkoxy, amino, thio, or halo groups.

The phrase "cycloalkylene" refers to divalent cycloalkyl groups comprising from 3 to 20 carbon atoms, and "substituted cycloalkylene" refers to cycloalkylene groups further bearing one or more substituents as set forth above.

The phrase "heterocyclyl", "heterocyclic", or "heterocycle" refers to nonaromatic cyclic hydrocarbyl compounds of which at least one ring member is a heteroatom. Heterocyclic groups include monocyclic, bicyclic, and polycyclic ring compounds containing from 3 to 20 ring members of which one or more is a heteroatom such as, but not limited to, N, O, and S. Heterocyclic groups include, any level of saturation. For instance, heterocyclic groups include unsaturated 3 to 8 membered rings containing 1 to 4 nitrogen atoms; saturated 3 to 8 membered rings containing 1 to 4 nitrogen atoms; condensed unsaturated heterocyclic groups containing 1 to 4 nitrogen atoms; unsaturated 3 to 8 membered rings containing 1 to 2 oxygen atoms and 1 to 3 nitrogen atoms; saturated 3 to 8 membered rings containing 1 to 2 oxygen atoms and 1 to 3 nitrogen atoms; unsaturated condensed heterocyclic groups containing 1 to 2 oxygen atoms and 1 to 3 nitrogen atoms; unsaturated 3 to 8 membered rings containing 1 to 3 sulfur atoms and 1 to 3 nitrogen atoms. Preferred heterocyclyl groups contain 5 or 6 ring members. Examples of heterocyclic groups include, but are not limited to, morpholine and piperazine. The phrase "substituted heterocyclyl" or "substituted heterocyclic" refers to a heterocyclyl group that is substituted according to the definition provided above.

The phrase "heterocyclene" or "heterocyclylene" refers to divalent heterocyclic (i.e., ring-containing) groups comprising from 3 to 20 carbon atoms and "substituted heterocycloalkylene" refers to heterocycloalkylene groups further bearing one or more substituents as set forth above.

The phrase "aryl" refers to single-ring aromatic radicals which may include from 5 to 20 carbon atoms. Aryl groups include, but are not limited to, phenyl, biphenyl, anthracenyl, and naphthenyl. The phrase "substituted aryl group" refers to an aryl group that is substituted according to the definition provided above. For example, substituted aryl groups may be bonded to one or more carbon atom(s), oxygen atom(s), nitrogen atom(s), and/or sulfur atom(s) and also includes aryl groups in which one or more aromatic carbons of the aryl group is bonded to a substituted and/or unsubstituted alkyl, alkenyl, or alkynyl group. This includes bonding arrangements in which two carbon atoms of an aryl group are bonded to two atoms of an alkyl, alkenyl, or alkynyl group to define a fused ring system (e.g. dihydronaphthyl or tetrahydronaphthyl). Thus, the phrase "substituted aryl" includes, but is not limited to tolyl, hydroxyphenyl, and the like.

The phrase "arylene" refers to divalent aryl groups comprising from 3 to 20 carbon atoms and "substituted arylene" refers to arylene groups further bearing one or more substituents as set forth above.

The phrase "heteroaryl" refers to a 3 to 20-membered aromatic ring consisting of carbon atoms and heteroatoms, such as N, S, and O or (ii) an 8- to 10-membered bicyclic or polycyclic ring system containing carbon atoms and heteroatoms, such as N, S, and O, wherein at least one of the rings in the bicyclic system is an aromatic ring. The heteroaryl ring may be attached at any heteroatom or carbon atom. Representative heteroaryl compounds include, for example, imidazolyl, pyridyl, pyrazinyl, pyrimidinyl, thiophenyl, thiazolyl, furanyl, pyridofuranyl, pyrimidofuranyl, pyridothienyl, pyridazothienyl, pyridooxazolyl, pyridazooxazolyl, pyrimidooxazolyl, pyridothiazolyl, pyridazothiazolyl, pyrrolyl, pyrrolinyl, imidazolyl, pyrazolyl, pyridyl, dihydropyridyl, pyrimidyl, pyrazinyl, pyridazinyl, triazolyl (e.g. 4H-1,2,4-triazolyl, 1H-1,2,3-triazolyl, and 2H-1,2,3-triazolyl), tetrazolyl, (e.g. 1H-tetrazolyl and 2H tetrazolyl), pyrrolidinyl, imidazolidinyl, piperidinyl, piperazinyl, indolyl, isoindolyl, indolinyl, indolizinyl, benzimidazolyl, quinolyl, isoquinolyl, indazolyl, benzotriazolyl, oxazolyl, isoxazolyl, oxadiazolyl (e.g. 1,2,4-oxadiazolyl, 1,3,4-oxadiazolyl, and 1,2,5-oxadiazolyl), benzoxazolyl, benzoxadiazolyl, benzoxazinyl (e.g. 2H-1,4-benzoxazinyl), thiazolyl, isothiazolyl, thiadiazolyl (e.g. 1,2,3-thiadiazolyl, 1,2,4-thiadiazolyl, 1,3,4-thiadiazolyl, and 1,2,5-thiadiazolyl). The phrase "substituted heteroaryl" refers to a heteroaryl group that is substituted according to the definition provided above.

The phrase "heteroarylene" refers to divalent aryl groups containing one or more heteroatoms N, O, S or the like) as part of the aromatic ring, and typically having in the range of 3 up to 20 carbon atoms and "substituted heteroarylene" refers to heteroarylene groups further bearing one or more substituents as set forth above.

The phrase "alkoxy" refers to an oxygen-containing alkyl or cycloalkyl group, as defined above.

The phrase "alkylamido" refers to an alkyl group, as defined as above, which comprises —C(O)NR$_2$ wherein each R is independently hydrogen, alkyl, cycloalkyl, aryl, heteroaryl, or the like. Furthermore, alkylamido embraces embodiments wherein R, together with N, forms a cyclic structure.

The phrase "amino" refers to —NR$_2$ wherein each R is independently hydrogen, alkyl, cycloalkyl, aryl, heteroaryl, and the like. Furthermore, amino embraces embodiments wherein R, together with N, forms a cyclic structure.

The phrase "alkylamino" refers to an alkyl group, as defined as above, which comprises an amino group, as defined above.

The phrase "halogen" refers to F, Cl, Br, or I.

The phrase "linker" refers to any chemical moiety which can be used to join, attach, or connect two or more radicals of hydrocarbyl, substituted hydrocarbyl, heteroatom-containing substituted hydrocarbyl, or substituted heteroatom-containing hydrocarbyl groups. Representative linkers include —C≡C—, —C=C—, —(C(R')$_2$)$_z$—, —O—, —O—(C(R')$_2$)$_z$—, —S—, —NR'—, —NH—(C(R')$_2$)$_z$—, —N=N—, —C(O)—, —C(O)NR'—, —O—C(O)—, —O—C(O)—O—, —O—C(O)—NR'—, —NR'—C(O)—, —NR'—C(O)—NR'—, —S—C(O)—, —S—C(O)—O—, —S—C(O)—NR'—, —S(O)—, —S(O)$_2$—, —O—S(O)$_2$—, —O—S(O)$_2$—O—, —O—S(O)$_2$—NR'—, —O—S(O)—, —O—S(O)—O—, —O—S(O)—NR'—, —O—NR'—C(O)—O—, —NR'—O—C(O)—O—, —O—NR'—C(O)—NR'—, —NR'—O—C(O)—, —NR'—O—C(O)—O—, —NR'—O—C(O)—NR'—, —O—NR'—C(S)—, —O—NR'—C(S)—O—, —O—NR'—C(S)—NR'—, —NR'—O—C(S)—, —NR'—O—C(S)—O—, —NR'—O—C(S)—NR'—, —O—C(S)—, —O—C(S)—O—, —O—C(S)—NR'—, —NR'—C(S)—, —NR'—C(S)—O—, —NR'—C(S)—NR'—, —S—S(O)$_2$—, —S—S(O)$_2$—O—, —S—S(O)$_2$—NR'—, —NR'—O—S(O)—, —NR'—O—S(O)—O—, —NR'—O—S(O)—NR'—, —NR'—O—S(O)$_2$—, —NR—O—S(O)$_2$—O—, —NR'—O—S(O)$_2$—NR'—, —O—NR'—S(O)—, —O—NR'—S(O)—O—, —O—NR'—S(O)—NR'—, —O—NR'—S(O)$_2$—O—, —O—NR'—S(O)$_2$—NR'—, —O—NR'—S(O)$_2$—, —O—P(O)(R')$_2$—, —S—P(O)(R')$_2$—, and —NR'—P(O)(R')$_2$—, wherein each R' is independently hydrogen, substituted or unsubstituted alkyl, substituted or unsubstituted alkenyl, substituted or unsubstituted alkynyl, or substituted or unsubstituted cycloalkyl, and z is 1-10. Preferred embodiments herein include compounds of Formula (I) wherein L$_C$ is —NH—.

Embodiments presented herein include compounds of Formula (I) wherein A, together with B, or B, together with C, forms a fused ring system. Exemplary fused systems include,

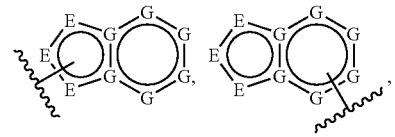

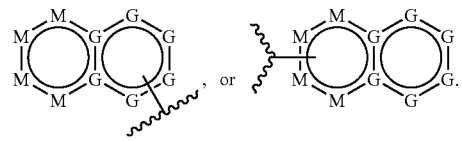

The phrase "fused ring system" refers to two or three rings that are fused together e.g. bicyclic or tricyclic ring systems. Representative fused ring systems include, for example, naphthyl, 1-carbolinyl, and the like; and substituted ring systems, such as biphenyl, phenylpyridyl, diphenylpiperazinyl, and the like.

Preferred embodiments herein include compounds of Formula (I) wherein D is

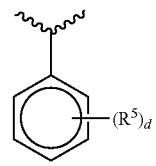

and d is 0-5. Preferred embodiments of each $R^5$, when present, are independently selected from halogen, substituted or unsubstituted $C_1$-$C_5$ alkyl, substituted or unsubstituted $C_1$-$C_5$ alkoxy, substituted or unsubstituted five to six-membered heteroaryl, or $N(R'')_2$ wherein each R'' is independently a substituted or unsubstituted $C_1$-$C_5$ alkyl or $C_3$-$C_{10}$ cycloalkyl. Embodiments of D further include compounds wherein D, together with $R^5$, forms a fused ring system. More preferred embodiments of D are selected from

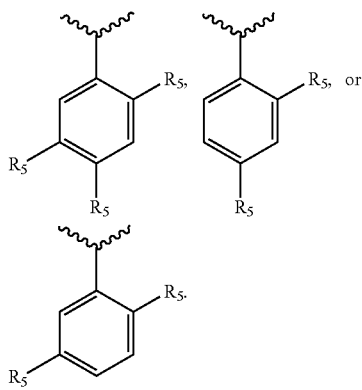

Preferred embodiments herein include compounds of Formula (I) wherein C is

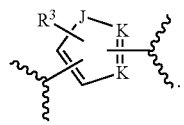

For instance, embodiments of C may be selected from

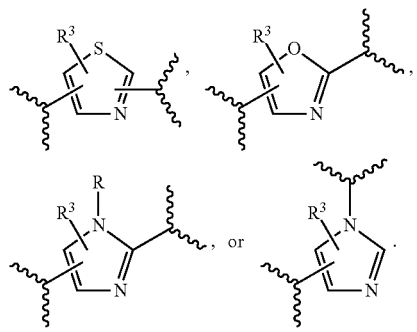

More preferred embodiments include compounds of Formula (I) wherein C is

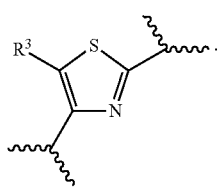

Preferred embodiments herein include compounds of Formula (I) wherein B is

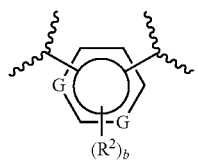

and b is 0-2. For instance, embodiments of B may be selected from

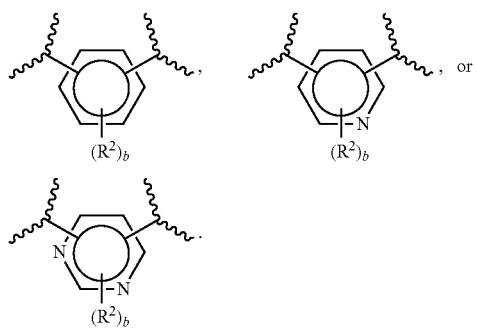

More preferable embodiments include compounds of Formula (I) wherein B is selected from

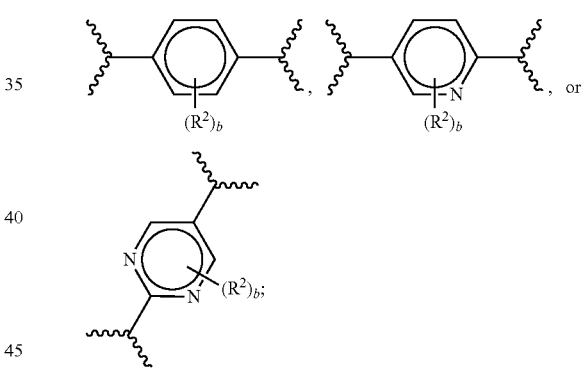

wherein each $R^2$ is independently selected from halogen or substituted or unsubstituted $C_1$-$C_5$ alkyl.

Preferred embodiments herein include compounds of Formula (I) wherein

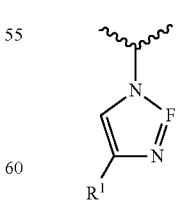

wherein F is CH or N. More preferable embodiments of A include compounds where $R^1$ is halogen or substituted or unsubstituted $C_1$-$C_5$ alkyl.-

Preferable embodiments presented herein include compounds having a structure corresponding to Formula (II):

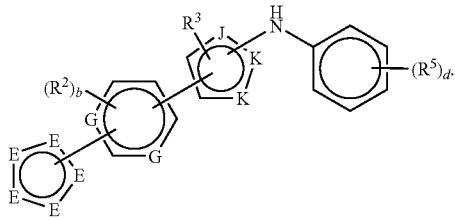

(II)

Additional preferred embodiments herein include compounds having a structure corresponding to Formula (III):

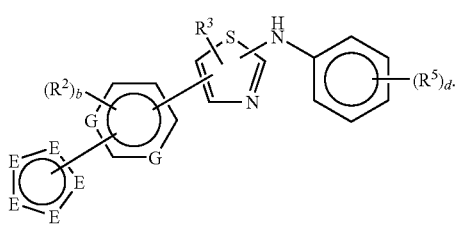

(III)

Further preferred embodiments herein include compounds having a structure corresponding to Formula (IV):

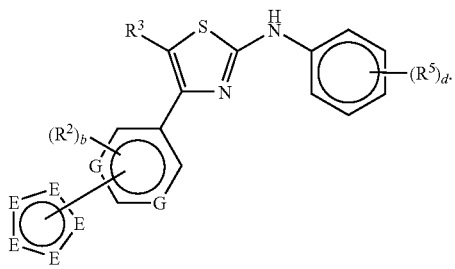

(IV)

Even further preferred embodiments herein include compounds having a structure corresponding to Formula (V):

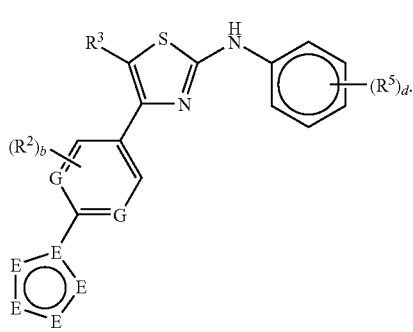

(V)

Especially preferred embodiments herein include compounds having a structure corresponding to Formula (VI):

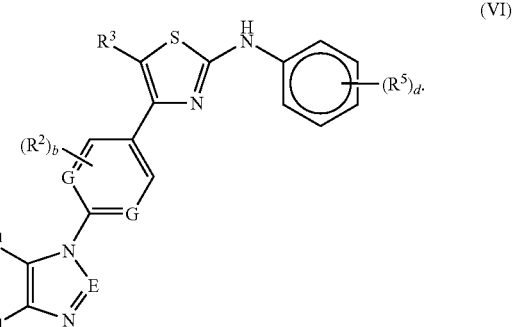

(VI)

Presented embodiments include compositions comprising compounds of Formula (I) and a pharmaceutically acceptable carrier; and kits comprising compounds of Formula (I) and instructions for use.

II. Preparation of Compounds

Presented below are exemplary general SCHEMEs for the preparation of invention compounds. Further details of synthetic methods are provided in the Examples herein. Since compounds herein can be readily prepared according to procedures well known to one of ordinary skill in the art, numerous methods, in lieu of or in addition to the synthetic SCHEMEs presented below, may be employed to prepare compounds herein.

Derivatives and chemically similar compounds within the scope of the instant disclosure may be prepared by routine modification of the procedures provided herein using the appropriate starting materials, the selection of which will be evident to those of skill in the art.

A. General Condensation Scheme

Compounds herein which comprise aminothiazole or aminooxazole moieties (3) can be prepared by combining an α-halogenated ketone derivative (1) with an appropriate thiourea or urea compound (2). For instance, a generalized scheme for preparation of 2-aminothiazole compounds is depicted below in SCHEME 1. SCHEME 1 can be manipulated to prepare invention compounds by varying rings A, B, and D, for instance.

SCHEME 1

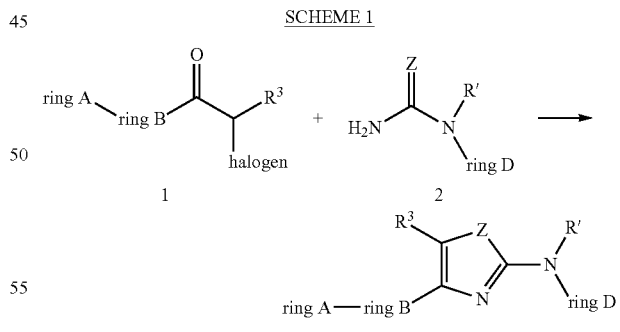

Z = S or O

Alternatively, condensation reactions may also be performed with simple thioureas, such as $NH_2$—C(=S)—$NH_2$, and varying α-bromoketone derivatives. As exemplified in the route of SCHEME 2, the resultant amine (4) may be conjugated with a carboxylic acid derivative comprising ring D (5) in the presence of a coupling agent to produce amide-linked compounds (6).

SCHEME 2

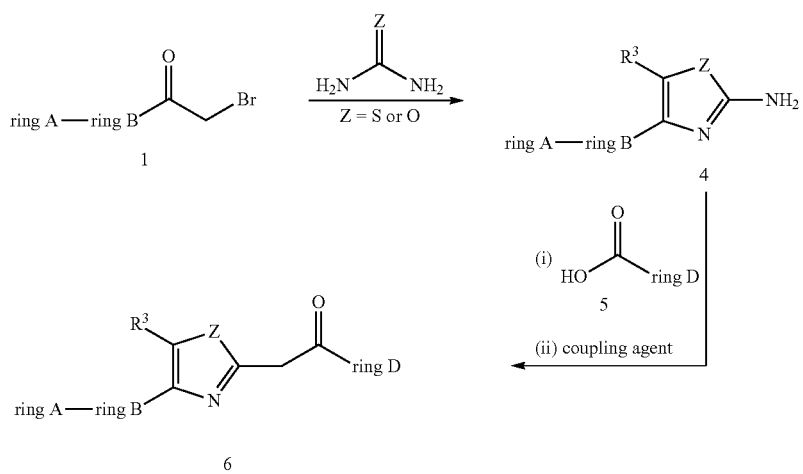

B. Preparation of α-Bromoketone Derivatives

Preferable halogenated ketone derivatives employed in SCHEME 1 include α-bromoketone derivatives. As shown in SCHEME 3 below, bromination of an appropriate alkyl ketone results in formation of an α-bromoketone derivative.

SCHEME 3

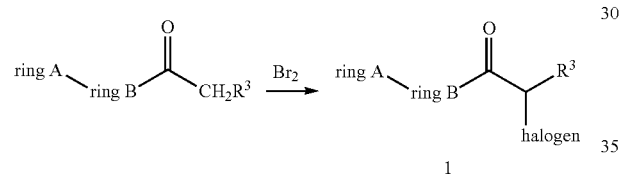

Thus, by varying the moieties for rings A and B in SCHEME 3, a multitude of α-bromoketone derivatives can be prepared. For instance, α-bromoketone derivatives where ring A is an imidazole derivative and ring B is a phenyl derivative (1a) can be prepared according to SCHEME 4. Furthermore, SCHEME 4 can also be employed to prepare α-bromoketone derivatives where ring A is triazole or thiazole derivative, for instance.

SCHEME 4

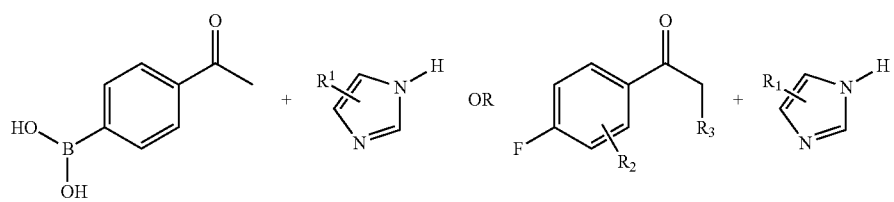

TL., 1998, 39 (19), 2941-2944

Aust. J. Chem., 1977, 30, 629-637
Chem. Pharm. Bull. 1998, 46(4) 623-630

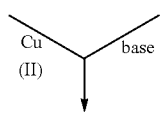

-continued

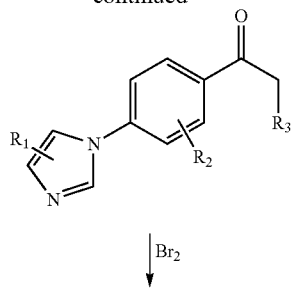

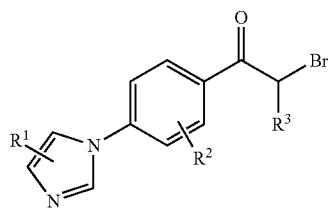
1a

α-bromoketone derivatives where ring A is non-aromatic derivative, such as piperazine, and ring B is a phenyl derivative can be readily prepared by bromination of corresponding ketone.

C. Preparation of Thiourea Derivatives

Thiourea or urea derivatives (2) are employed in the general condensation reaction depicted in SCHEME 1, and can be prepared by SCHEME 5. Generally, urea derivatives can be prepared by addition of an appropriate amine, such as an aniline derivative, to a suitable isothiocyanate compound.

SCHEME 5

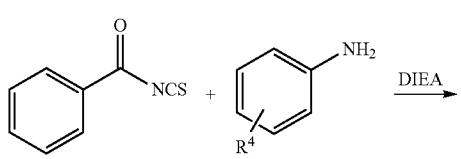
Synthesis, 1998, 456-459

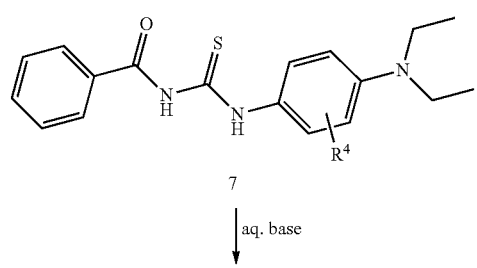
7
↓ aq. base

-continued

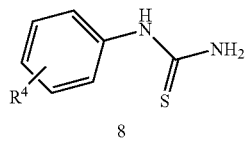
8

DIEA = diisopropyl ethyl amine

Thiourea derivatives 7 or 8 are suitable for condensation with α-bromoketone derivatives. Moreover, the corresponding urea derivatives of 7 or 8 may also be suitably employed in the general condensation presented herein.

D. Alternative Synthetic Route for Preparation of Substituted Aminothiazoles

In addition to the general condensation routes depicted above in SCHEMEs 1 and 2, various substituted thiazole and pyridine derivatives may also be prepared using a modified Suzuki coupling reaction as shown below in SCHEME 6.

SCHEME 6

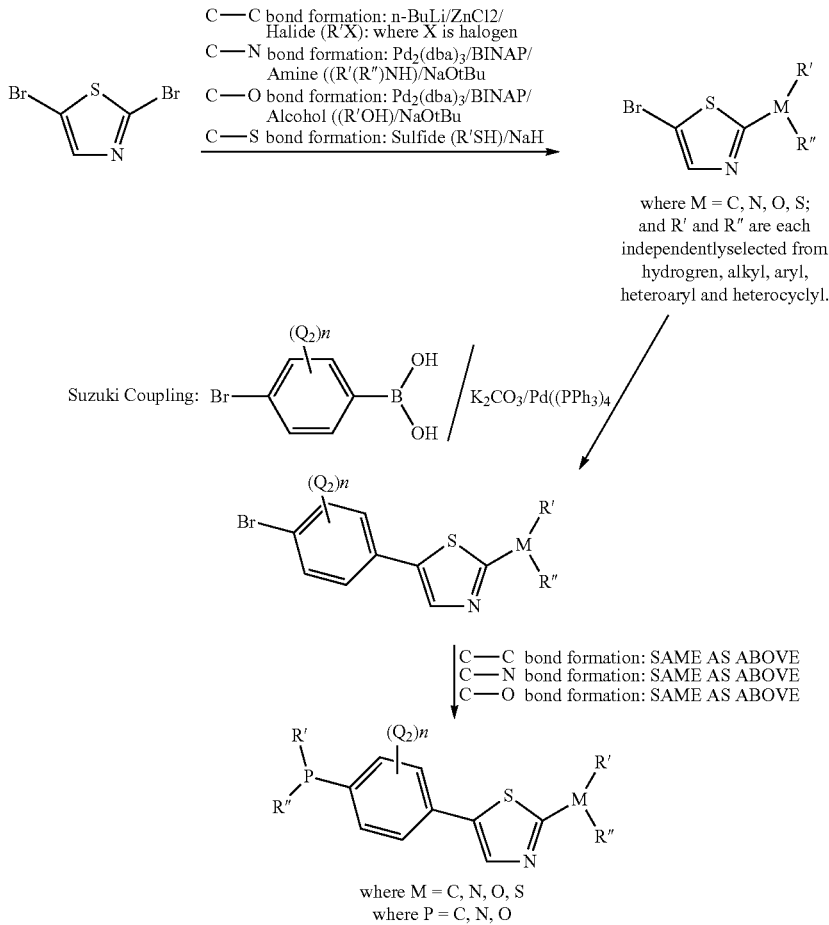

Aminothiazole derivatives can be prepared by modification of SCHEME 6 as shown in SCHEME 7 below. Note that all conditions for bond formations in SCHEME 7 are the same as in SCHEME 6.

SCHEME 7

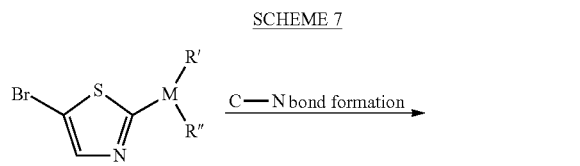

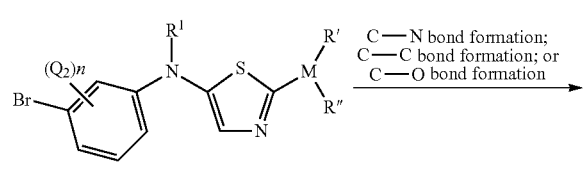

-continued

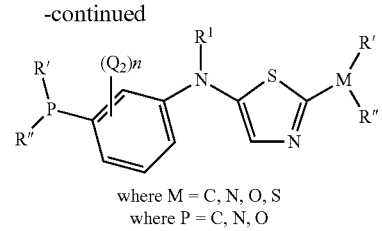

where M = C, N, O, S
where P = C, N, O

III. Methods of Modulating Aβ and Methods for Treating Disease associated with Aβ

An aspect of the invention is drawn to methods of modulating Aβ levels and methods for treating a disease associated with aberrant Aβ levels using compounds having a structure corresponding to Formula (VII):

$$(A_1\text{-}L_{A1})_{0\text{-}1}\text{-}(B_1)\text{-}L_{B1}\text{-}(C_1)\text{-}L_{C1}\text{-}(D_1) \tag{VII}$$

and pharmaceutically acceptable salts, and prodrugs thereof, wherein:

$A_1$ is optional, and when present is a five or six-membered substituted or unsubstituted cycloalkyl, heterocyclyl, aryl, heteroaryl, cycloalkylene, heterocyclylene, arylene, or heteroarylene;

$B_1$ is a five or six-membered substituted or unsubstituted cycloalkylene, heterocyclylene, arylene, or heteroarylene; or $B_1$, together with $A_1$, forms a fused ring system;

$C_1$ is a five or six-membered substituted or unsubstituted arylene or heteroarylene;

$D_1$ is a five or six-membered substituted or unsubstituted aryl, heteroaryl, arylene, or heteroarylene; and $L_{A1}$ is optional, and when present, is a covalent bond or a linker;

each of $L_{B1}$ and $L_{C1}$ is independently a covalent bond or a linker;

wherein said compound of Formula (VII) modulates Aβ levels.

Preferable methods herein include use of compounds of Formula (VII), wherein:

$A_1$ is optional, and when present is:

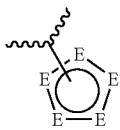

wherein each E is independently N, NR, C, $CR^1$, S, or O provided that no more than four E's are heteroatoms;

R is hydrogen, substituted or unsubstituted alkyl, substituted or unsubstituted alkenyl, substituted or unsubstituted alkynyl, substituted or unsubstituted alkoxy, substituted or unsubstituted alkylamido, substituted or unsubstituted alkylamino, substituted or unsubstituted cycloalkyl, or substituted or unsubstituted aryl;

each $R^1$ is hydrogen, halogen, substituted or unsubstituted alkyl, substituted or unsubstituted alkenyl, substituted or unsubstituted alkynyl, substituted or unsubstituted alkoxy, substituted or unsubstituted alkylamido, substituted or unsubstituted alkylamino, substituted or unsubstituted amino, substituted or unsubstituted cycloalkyl, or substituted or unsubstituted aryl;

or $A_1$, when present is:

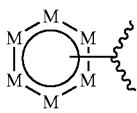

wherein each M is independently selected from $CR^1$ or N, provided that no more than three M's are N; and $B_1$ is:

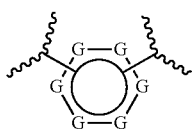

wherein each G is independently $CR^2$ or N, provided that no more than three G's are N;

each $R^2$ is independently selected from hydrogen, halogen, substituted or unsubstituted alkyl, substituted or unsubstituted alkenyl, substituted or unsubstituted alkynyl, substituted or unsubstituted alkoxy, substituted or unsubstituted alkylamido, substituted or unsubstituted alkylamino, substituted or unsubstituted amino;

$C_1$ is:

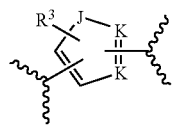

wherein J is selected from the group consisting of $CR^3$, O, S, N, and NR;

each K is independently N, NR, C, or $CR^3$;

$R^3$ is hydrogen, halogen, substituted or unsubstituted alkyl, substituted or unsubstituted cycloalkyl, substituted or unsubstituted aryl, substituted or unsubstituted heteroaryl, or substituted or unsubstituted alkoxy;

or $C_1$ is:

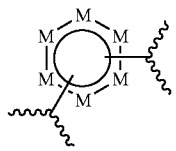

wherein each M is independently selected from $CR^1$ or N, provided that no more than three M's are N;

$D_1$ is:

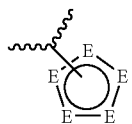

wherein each E is independently N, NR, C, $CR^1$, S, or O provided that no more than four E's are heteroatoms;

or $D_1$ is:

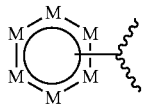

wherein each M is independently selected from $CR^5$ or N, provided that no more than three M's are N;

each $R^5$ is independently selected from hydrogen, halogen, substituted or unsubstituted alkyl, substituted or unsubstituted alkenyl, substituted or unsubstituted alkynyl, substituted or unsubstituted alkoxy, substituted or unsubstituted cycloalkyl, substituted or unsubstituted heterocycle, substituted or unsubstituted aryl, substituted or unsubstituted heteroaryl, or substituted or unsubstituted amino, or substituted or unsubstituted alkylamino;

$L_{A1}$, when present, and each of $L_{B1}$ and $L_{C1}$ is independently a covalent bond or a linker selected from the group consisting of —C=C—, —C≡C—, —(C(R')$_2$)$_z$—, —O—, —O—(C(R')$_2$)$_z$—, —S—, —NR'—, —NH—(C(R')$_2$)$_z$—, —N=N—, —C(O)—, —C(O)NR'—, —O—C(O)—, —O—C(O)—O—, —O—C(O)—NR'—, —NR'—C(O)—, —NR'—C(O)—O—, —NR'—C(O)—NR'—, —S—C(O)—, —S—C(O)—O—, —S—C(O)—NR'—, —S(O)—, —S(O)$_2$—, —O—S(O)$_2$—, —O—S(O)$_2$—O—, —O—S(O)$_2$—NR'—, —O—S(O)—, —O—S(O)—O—, —O—S(O)—NR'—, —O—NR'—C(O)—, —O—NR'—C(O)—O—, —O—NR'—C(O)—NR'—, —NR'—O—C(O)—, —NR'—O—C(O)—O—, —NR'—O—C(O)—NR'—, —O—NR'—C(S)—, —O—NR'—C(S)—O—, —O—NR'—C(S)—NR'—, —NR'—O—C(S)—, —NR'—O—C(S)—O—, —NR'—O—C(S)—NR'—, —O—C(S)—, —O—C(S)—O—, —O—C(S)—NR'—, —NR'—C(S)—, —NR'—C(S)—O—, —NR'—C(S)—NR'—, —S—S(O)$_2$—, —S—S(O)$_2$—O—, —S—S(O)$_2$—NR'—O—S(O)—, —NR'—O—S(O)—O—, —NR'—O—S(O)—NR'—, —NR'—O—S(O)$_2$—, —NR', —O—S(O)$_2$—O—, —NR'—O—S(O)$_2$—NR'—, —O—NR'—S(O)—, —O—NR'—S(O)—NR'—, —O—NR'—S(O)$_2$—O—, —O—NR'—S(O)$_2$—, —O—P(O)(R')$_2$—, —S—P(O)(R')$_2$—, and —NR'—P(O)(R')$_2$—, wherein each R' is independently hydrogen, substituted or unsubstituted alkyl, substituted or unsubstituted alkenyl, substituted or unsubstituted alkynyl, or substituted or unsubstituted cycloalkyl, and z is 1 to 10.

Preferable methods herein include use of compounds of Formula (VII) wherein $L_{C1}$ is —O—, —S—, —S(O)—, —S(O)$_2$—, —NR'—, —C(O)—, —(C(R')$_2$)$_z$—, or —C(S)—.

More preferable embodiments herein include methods of modulating levels and methods for treating a disease associated with aberrant Aβ levels using compounds corresponding to Formulas (II), (III), (IV), (V), or (VI).

The phrase "amyloid-beta" or "Aβ" refers to a peptide from a human or other species that (a) results from processing or cleavage of an APP and that is amyloidogenic, (b) is one of the peptide constituents of β-amyloid plaques, (c) is the 43-amino acid sequence of Aβ (amino acid 672-714 of APP770; GenBank Accession No. P05067), (d) is a fragment of a peptide as set forth in (a), (b) or (c), and/or (e) contains one or more additions, deletions or substitutions relative to (a), (b), (c) or (d). Aβ is also referred to in the art as βAP, AβP, or βA4. Aβ peptides derived from proteolysis of APP generally are ~4.2 kD proteins and are typically 39 to 43 amino acids in length, depending on the carboxy-terminal end-point, which exhibits heterogeneity. However, Aβ peptides containing less than 39 amino acids, e.g., Aβ38, Aβ37, and Aβ34, also may occur.

Aβ peptides can be produced in an amyloidogenic APP processing pathway in which APP is cleaved by β-secretase (BACE) and one or more γ-secretase activities. Aβ peptides include those that begin at position 672 of APP770 and those that begin at position 682 of APP770 (see, for example, GenBank Accession No. P05067). Generally, as used herein, "Aβ" includes any and all Aβ peptides, unless the amino acid residues are specified, such as, for example, 1-43 (Aβ43), 1-42 (Aβ42), 1-40 (Aβ40), 1-39 (Aβ39), 1-38 (Aβ38), 1-37 (Aβ37), 1-34 (Aβ34), 11-43, 11-42, 11-40, 11-39, 11-38, 11-37, 11-34, and others. The various Aβ peptides of differing lengths are referred to herein as "species" of Aβ.

The phrase "amyloid precursor protein" or "APP" refers to a protein that can be proteolytically processed or cleaved by one or more processing or cleavage reactions to produce Aβ. APP includes all isoforms that are generated by alternative splicing, which can be typically distinguished by the number of amino acids in the particular isoform. For example, APP embraces APP695, APP751, and APP770. Other isoforms of APP include, for example, APP714, L-APP752, L-APP733, L-APP696, L-APP677, APP563, and APP365.

APP also includes all isoforms containing mutations found in families with AD and other amyloidosis conditions. For example, these mutations include the Swedish (Lys670Asn, Met671Leu) double mutation; the London mutation (Val717Ile), the Indiana mutation (Val717Leu), Val717Phe, Val717Gly, Ala713Thr, Ala713Val, the Austrian mutation (Thr714Ile), the Iranian mutation (Thr714Ala), the French mutation (Val715Met), the German mutation (Val715Ala), the Florida mutation (Ile716Val), Ile 716Thr, the Australian mutation (Leu723Pro), the Flemish mutation (Ala692Gly), the Dutch mutation (Glu693Gln), the Arctic mutation (Glu693Gly), the Italian mutation (Glu693Lys), and the Iowa mutation (Asp694Asn), and the amyloidsis-Dutch type mutation (Glu693Gln). (All numbering herein is relative to the APP770 form).

The term "APP" further includes proteins containing one or more additions, deletions or substitutions relative to the isoforms described above, and APP proteins from humans and other species. Unless a specific isoform is specified, APP when used herein generally refers to any and all isoforms of APP, with or without mutations, from any species.

The phrase "amyloid precursor protein fragment" refers to any portion of an APP that can be processed or cleaved, by one or more processing or cleavage reactions, to Aβ. Amyloid precursor fragments of APP generally contain either a beta-secretase cleavage site which, when cleaved, generates the N-terminus of Aβ, a gamma-secretase cleavage site which, when cleaved, generates the C-terminus of Aβ or both a beta- and a gamma-secretase cleavage site. Exemplary amyloid precursor fragments include the APP C-terminal fragments designated C99 and C89, as well as portions thereof lacking some or all C-terminal residues that normally reside in the cytosol.

The phrase "source of amyloid precursor protein (APP), amyloid precursor fragment thereof and/or Aβ" refers to any in vivo, ex vivo or in vitro substance containing APP, amyloid precursor fragment thereof and/or Aβ. For example, a "source" can be a live organism (including a human patient, or a laboratory or veterinary animal), a sample therefrom (such as a tissue or body fluid, or extract thereof), a cell (such as a primary cell or cell line, or extract thereof), extracellular medium or matrix or milieu, or isolated protein.

The phrase "modulate" or "modulating" with respect to Aβ level, refers to a detectable increase or decrease in the amount of at least one species of Aβ peptide (such as Aβ43, Aβ42, Aβ40, Aβ39, Aβ38, Aβ37, Aβ34, 11-43, 11-42, 11-40, 11-39, 11-38, 11-37, 11-34, etc.); a detectable increase or decrease in the relative amount of different species of Aβ peptides (such as the ratio of Aβ42 to Aβ40); a detectable increase or decrease in the amount, or relative amount, of Aβ in a particular form (such as monomeric, oligomeric, or fibrillar form; in solution or aggregated in a plaque; in a particular conformation; etc.); and/or a detectable increase or decrease in the amount, or relative amount, of Aβ in a particular location (such as an intracellular, membrane-associated or extracellular location, or in a particular tissue or body fluid). In preferred embodiments, modulation is detectable as a decrease in the level of Aβ42 or Aβ40, or an increase in the level of Aβ37 or Aβ38. Modulation of Aβ level can be evidenced, for example, by an increase or decrease of at least 5%, such as at least 10%, 20%, 30%, 40%, 50%, 75%, 90% or more, of the amount, or relative amount, of an Aβ species, of total Aβ, or of a particular form of Aβ, relative to a reference level. Modulation can be an increase or decrease that is a statistically significant difference relative to the reference level.

The phrase "contacting" refers to bringing into association, either directly or indirectly, two or more substances. Contacting may occur in vivo, ex vivo or in vitro. A source of APP, amyloid precursor fragment thereof and/or Aβ or source of BACE activity, that is a human or other animal can be contacted with a compound, for example, by therapeutic or prophylactic administration of the compound. A source of APP, amyloid precursor fragment thereof and/or Aβ that is a tissue, tissue extract or cell can be contacted with a compound, for example, by introduction of the compound into the culture medium. A source of APP, amyloid precursor fragment thereof and/or Aβ that is a fluid, such as extracellular medium, can be contacted with a compound, for example, by admixing the compound with the fluid.

The phrase "treating" or "treatment" refers to any manner in which one or more of the symptoms of a disease or disorder are ameliorated or otherwise beneficially altered, whether in a permanent or temporary manner, which can be attributed to or associated with administration of the compound or composition herein. The term encompasses any pharmaceutical use, including prophylactic uses in which the development of one or more of the symptoms of a disease or disorder is prevented, delayed or reduced, whether in a permanent or temporary manner, which can be attributed to or associated with administration of the composition. In an embodiment of the invention, treatment encompasses any pharmaceutical use of compounds herein for treating a disease or disorder characterized by altered or aberrant Aβ production, catabolism, processing and/or levels.

The phrase "disease associated with aberrant Aβ levels" refers to any condition characterized by an abnormal amount of at least one species of Aβ peptide (such as Aβ43, Aβ42, Aβ40, Aβ39, Aβ38, Aβ37, Aβ34, 11-43, 11-42, 11-40, 11-39, 11-38, 11-37, 11-34, etc.); by an abnormal relative amount of different species of Aβ peptides (such as the ratio of Aβ42 to Aβ40); by an abnormal amount, or relative amount, of Aβ in a particular form (such as monomeric, oligomeric, or fibrillar form; in solution or aggregated in a plaque; in a particular conformation, etc.); and/or by an abnormal amount, or relative amount, of Aβ in a particular location (such as intracellular, membrane-associated or extracellular location, or in a particular tissue or body fluid). The abnormal amount of one or more Aβ, peptides, Aβ forms and/or Aβ can be relative to a condition that is a normal, non-disease state. Diseases and disorders characterized by altered Aβ levels are known in the art and/or described herein, and include, for example, Down syndrome, Parkinson's disease, diffuse Lewy body disease, progressive supranuclear palsy, Hereditary Cerebral Hemorrhage with Amyloidosis-Dutch Type (HCHWA-D), cerebral amyloid angiopathy (CAA), and mild cognitive impairment (MCI). Embodiments of the invention include methods of treating any disease associated with aberrant Aβ levels, such as AD. Compounds of the present invention can be administered to a subject to treat (including to prevent or to ameliorate) conditions associated with altered Aβ production, fibril formation/deposition, degradation and/or clearance, or any altered isoform of Aβ.

Preferably, compounds of the present invention can be used in the treatment of neurological disorders, including but not limited to neurodegenerative conditions and other dementias or traumatic conditions. Exemplary neurological disorders may include diffuse Lewy body disease, Pick's disease, multisystem degeneration (Shy-Drager syndrome), motor neuron diseases including amyotrophic lateral sclerosis, degenerative ataxias, cortical basal degeneration, ALS-Parkinson's-Dementia complex of Guam, subacute sclerosing panencephalitis, Huntington's disease, synucleinopathies, primary progressive aphasia, striatonigral degeneration, Machado-Joseph diseaseispinocerebellar ataxia type 3 and olivopontocerebellar degenerations, Gilles De La Tourette's disease, bulbar and pseudobulbar palsy, spinal and spinobulbar muscular atrophy (Kennedy's disease), primary lateral sclerosis, familial spastic paraplegia, Werdnig-Hoffmann disease, Kugelberg-Welander disease, Tay-Sach's disease, Sandhoff disease, familial spastic disease, Wohifart-Kugelberg-Welander disease, spastic paraparesis, progressive multifocal leukoencephalopathy, prion diseases (including Creutzfeldt-Jakob, Gerstmann-Straussler-Scheinker disease, Kuru and fatal familial insomnia), age-related dementia and other conditions with memory loss, such as vascular dementia, diffuse white matter disease (Binswanger's disease), dementia of endocrine or metabolic origin, dementia of head trauma and diffuse brain damage, dementia pugilistica and frontal lobe dementia, cerebral ischemia or infaction including embolic occlusion and thrombotic occlusion as well as intracranial hemorrhage of any type (including, but not limited to, epidural, subdural, subarachnoid and intracerebral), and intracranial and intravertebral lesions (including, but not limited to, contusion, penetration, shear, compression and laceration).

IV. Alternative Therapeutic Applications

Compounds and compositions of the instant invention may be used to treat or ameliorate a variety of disorders. Compounds and compositions that may be used in therapeutic applications, in one embodiment have reasonably high bioavailability in a target tissue (i.e. brain, for neurodegenerative disorders; particular peripheral organs for other amyloidogenic conditions), and reasonably low toxicity. Those skilled in the art can assess compounds described herein for their pharmaceutical acceptability using standard methods.

For instance, compounds of the instant invention can be used in the treatment of cancer or other diseases characterized by abnormal cellular proliferation, inflammatory disease, bacterial or viral infection, autoimmune disease, acute pain, muscle pain, neuropathic pain, allergies, neurological disease, dermatological conditions, cardiovascular disease, diabetes, gastrointestinal disorders, depression, endocrine or other disease characterized by abnormal hormonal metabolism, obesity, osteoporosis or other bone disorders, pancreatic disease, epilepsy or seizure disorders, erectile or sexual dysfunction, opthamological disorders or diseases of the eye, cholesterol imbalance, hypertension or hypotension, migraine or headaches, obsessive compulsive disorder, panic disorder, anxiety disorder, post traumatic stress disorder, chemical dependency or addiction, and the like.

Compounds provided herein can also be used to prevent or treat amyloidoses. Amyloidoses include all conditions in which deposition of amyloid in the brain or periphery is a characteristic, including amyloidosis associated with rheumatic diseases, idiopathic diseases, inherited conditions, inflammatory conditions, infectious diseases and malignancies. Amyloidosis disorders include, for example, conditions associated with altered Aβ levels described above (e.g. Alzheimer's disease, Down syndrome, HCHWA-D, cerebral amyloid angiopathy (CAA), and mild cognitive impairment (MCI) etc.), as well as familial amyloid polyneuropathy, familial amyloid cardiomyopathy (Danish type), isolated cardiac amyloid, amyloid angiopathy, systemic senile amyloidosis, familial systemic amyloidosis, light-chain amyloidosis (AL), dialysis-associated amyloidosis, renal amyloidosis, prion-related encephalopathies, diabetes (in which amylin may be deposited in the kidney or pancreas), atrial amyloidosis and pituitary amyloidosis.

Those skilled in the art can determine other diseases and disorders for which administration of a compound or composition described herein can be beneficial.

V. Pharmaceutical Compositions

The phrase "pharmaceutically acceptable carrier" refers to any carrier known to those skilled in the art to be suitable for the particular mode of administration. In addition, the compounds may be formulated as the sole pharmaceutically active ingredient in the composition or may be combined with other active ingredients.

The phrase "pharmaceutically acceptable salt" refers to any salt preparation that is appropriate for use in a pharmaceutical application. Pharmaceutically-acceptable salts include amine salts, such as N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chloro-benzyl-2-pyrrolidin-F-ylmethylbenzimidazole, diethylamine and other alkylamines, piperazine, tris(hydroxymethyl)aminomethane, and the like; alkali metal salts, such as lithium, potassium, sodium, and the like; alkali earth metal salts, such as barium, calcium, magnesium, and the like; transition metal salts, such as zinc, aluminum, and the like; other metal salts, such as sodium hydrogen phosphate, disodium phosphate, and the like; mineral acids, such as hydrochlorides, sulfates, and the like; and salts of organic acids, such as acetates, lactates, malates, tartrates, citrates, ascorbates, succinates, butyrates, valerates, fumarates, and the like.

The phrase "prodrug" refers to a compound that, upon in vivo administration, is metabolized by one or more steps or processes or otherwise converted to the biologically, pharmaceutically or therapeutically active form of the compound. Prodrugs can be prepared by modifying functional groups present in the compound in such a way that the modifications are cleaved, either in routine manipulation or in vivo, to a compound described herein. For example, prodrugs include compounds of the present invention wherein a hydroxy, amino, or sulfhydryl group is bonded to any group that, when administered to a mammalian subject, can be cleaved to form a free hydroxyl, free amino, or free sulfhydryl group, respectively. Representative prodrugs include, for example, esters, enol ethers, enol esters, acetates, formates, benzoate derivatives, and the like of alcohol and amine functional groups in the compounds of the present invention. By virtue of knowledge of pharmacodynamic processes and drug metabolism in vivo, those of skill in this art, once a pharmaceutically active compound is known, can design prodrugs of the compound (see, e.g., Nogrady (1985) *Medicinal Chemistry A Biochemical Approach*, Oxford University Press, New York, pages 388-392).

Compositions herein comprise one or more compounds provided herein. The compounds are, in one embodiment, formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. In one embodiment, the compounds described above are formulated into pharmaceutical compositions using techniques and procedures well known in the art (see, e.g., Ansel *Introduction to Pharmaceutical Dosage Forms, Fourth Edition* 1985, 126).

In the compositions, effective concentrations of one or more compounds or pharmaceutically acceptable derivatives thereof is (are) mixed with a suitable pharmaceutical carrier. The compounds may be derivatized as the corresponding salts, esters, enol ethers or esters, acetals, ketals, orthoesters, hemiacetals, hemiketals, acids, bases, solvates, hydrates or prodrugs prior to formulation, as described above. The concentrations of the compounds in the compositions are effective for delivery of an amount, upon administration, that treats, prevents, or ameliorates one or more of the symptoms of diseases or disorders to be treated.

In one embodiment, the compositions are formulated for single dosage administration. To formulate a composition, the weight fraction of compound is dissolved, suspended, dispersed or otherwise mixed in a selected carrier at an effective concentration such that the treated condition is relieved, prevented, or one or more symptoms are ameliorated.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described herein and in PCT publication WO 04/018997, and then extrapolated therefrom for dosages for humans.

The concentration of active compound in the pharmaceutical composition will depend on absorption, inactivation and excretion rates of the active compound, the physicochemical characteristics of the compound, the dosage schedule, and amount administered as well as other factors known to those of skill in the art.

In one embodiment, a therapeutically effective dosage should produce a serum concentration of active ingredient of from about 0.1 ng/ml to about 50-100 µg/ml. The pharmaceutical compositions, in another embodiment, should provide a dosage of from about 0.001 mg to about 2000 mg of compound per kilogram of body weight per day. Pharmaceutical dosage unit forms are prepared to provide from about 0.01 mg, 0.1 mg or 1 mg to about 500 mg, 1000 mg or 2000 mg, and in one embodiment from about 10 mg to about 500 mg of the active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate. Derivatives of the compounds, such as prodrugs of the compounds may also be used in formulating effective pharmaceutical compositions.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are, in one embodiment, formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents and the like, for example, acetate, sodium citrate, cyclodextrine derivatives, sorbitan monolaurate, triethanolamine sodium acetate, triethanolamine oleate, and other such agents.

Actual methods of preparing such dosage forms are known, or will be apparent, to those skilled in this art; for example, see Remington's Pharmaceutical Sciences, Mack Publishing Company, Easton, Pa., 15th Edition, 1975.

Dosage forms or compositions containing active ingredient in the range of 0.005% to 100% (wt %) with the balance made up from non-toxic carrier may be prepared. Methods for preparation of these compositions are known to those skilled in the art. The contemplated compositions may contain 0.001%-100% (wt %) active ingredient, in one embodiment 0.1-95% (wt %), in another embodiment 75-85% (wt %).

A. Compositions for Oral Administration

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

1. Solid Compositions for Oral Administration

In certain embodiments, the formulations are solid dosage forms, in one embodiment, capsules or tablets. The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an emetic coating; and a film coating. Examples of binders include microcrystalline cellulose, gum tragacanth, glucose solution, acacia mucilage, gelatin solution, molasses, polyinylpyrrolidine, povidone, crospovidones, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

The compound, or pharmaceutically acceptable derivative thereof, could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient may be included.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

2. Liquid Compositions for Oral Administration

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is in one embodiment encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. RE28,819 and 4,358,603. Briefly, such formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl)acetals of lower alkyl aldehydes such as acetaldehyde diethyl acetal.

B. Injectables, Solutions and Emulsions

Parenteral administration, in one embodiment characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. In one embodiment, a therapeutically effective dosage is formulated to contain a concentration of at least about 0.1% w/w up to about 90% w/w or more, in certain embodiments more than 1% w/w of the active compound to the treated tissue(s).

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

C. Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

D. Topical Administration

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will, in one embodiment, have diameters of less than 50 microns, in one embodiment less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%-10% (vol %) isotonic solutions, pH about 5-7, with appropriate salts.

E. Compositions for Other Routes of Administration

Other routes of administration, such as transdermal patches, including iontophoretic and electrophoretic devices, and rectal administration, are also contemplated herein.

Transdermal patches, including iotophoretic and electrophoretic devices, are well known to those of skill in the art. For example, such patches are disclosed in U.S. Pat. Nos. 6,267,983, 6,261,595, 6,256,533, 6,167,301, 6,024,975, 6,010,715, 5,985,317, 5,983,134, 5,948,433, and 5,860,957.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The weight of a rectal suppository, in one embodiment, is about 2 to 3 µm.

Tablets and capsules for rectal administration are manufactured using the same pharmaceutically acceptable substance and by the same methods as for formulations for oral administration.

F. Targeted Formulations

The compounds provided herein, or pharmaceutically acceptable derivatives thereof, may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In one embodiment, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

G. Combination Therapy

In another embodiment, the compounds may be administered in combination, or sequentially, with another therapeutic agent. Such other therapeutic agents include those known for treatment, prevention, or amelioration of one or more symptoms of amyloidosis and neurodegenerative diseases and disorders. Such therapeutic agents include, but are not limited to, donepezil hydrochloride (Aracept), rivastigmine tartrate (Exelon), tacrine hydrochloride (Cognex) and galantamine hydrobromide (Reminyl).

VI. Kits

According to another aspect of the invention, kits are provided. Kits according to the invention include package(s) comprising compounds or compositions of the invention.

The phrase "package" means any vessel containing compounds or compositions presented herein. In preferred embodiments, the package can be a box or wrapping. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment.

The kit can also contain items that are not contained within the package but are attached to the outside of the package, for example, pipettes.

Kits may optionally contain instructions for administering compounds or compositions of the present invention to a subject having a condition in need of treatment. Kits may also comprise instructions for approved uses of compounds herein by regulatory agencies, such as the United States Food and Drug Administration, Kits may optionally contain labeling or product inserts for the present compounds. The package(s) and/or any product insert(s) may themselves be approved by regulatory agencies. The kits can include compounds in the solid phase or in a liquid phase (such as buffers provided) in a package. The kits also can include buffers for preparing solutions for conducting the methods, and pipettes for transferring liquids from one container to another.

The kit may optionally also contain one or more other compounds for use in combination therapies as described herein. In certain embodiments, the package(s) is a container for intravenous administration. In other embodiments, compounds are provided in an inhaler. In still other embodiments compounds are provided in a polymeric matrix or in the form of a liposome.

VII. Evaluation of activity of compounds 1n modulating Aβ Level

The compounds described herein include compounds which modulate Aβ levels. Compounds can be evaluated for activity in modulating Aβ level using a variety of assays known in the art and/or described herein. Generally, a source of APP or fragment thereof and/or Aβ is contacted with a compound for a suitable period of time, and a level of Aβ is directly or indirectly assessed, as described below. The level of Aβ in the presence of the compound is compared to the level in a suitable control (such as a vehicle control or a positive control) to determine whether the compound modulates Aβ level.

A. Source of App, Amyloid Precursor Fragment and/or Aβ

The source of APP, amyloid precursor fragment and/or Aβ used to assess the activity of a compound in modulating Aβ will depend on the product being detected and the nature of the assay. For example, to assess activity of a compound in modulating gamma-secretase cleavage of APP or an amyloid precursor fragment, an APP C-terminal fragment corresponding to a beta-secretase cleavage product can be used, such as C99. In cases in which the effect of the compound is being evaluated at any and all stages in APP production, full-length APP may be preferred.

Suitable sources of APP, amyloid precursor fragment and/or Aβ used to assess the activity of a compound include live laboratory animals (e.g. natural and transgenic animals), as well as tissues (e.g. brain), tissue extracts, body fluids (e.g. blood, plasma, cerebrospinal fluid, urine, etc.) and primary cells from humans or laboratory animals. Other sources include recombinant cell lines, cell lysates therefrom (whole cell extracts, membrane fractions, etc.) and extracellular medium therefrom. For certain applications, substantially purified APP or Aβ may alternatively be used. Methods of isolating tissues, production and maintenance of primary and recombinant cells, preparation of lysates, and protein purification compatible with Aβ assays are known in the art.

To directly or indirectly evaluate effects of a compound on Aβ peptide production, secretion and/or degradation, in vivo or in vitro sources can be used that contain APP, or an amyloid precursor fragment thereof, and have the ability to proteolytically process it to produce Aβ. To evaluate effects of a compound on Aβ form (e.g. monomeric, oligomeric or fibrillar form, or conformation), fibril deposition or fibril degradation, in vitro or in vivo sources containing Aβ monomers, oligomers or fibrils can be used, which optionally may not also contain APP- or amyloid precursor fragment-producing cells.

B. Transgenic Animals

Transgenic animals useful in evaluating compound activity can express any desired wild-type or mutant APP, amyloid precursor fragment or Aβ isoform, as described herein. The resulting animals can advantageously serve as models of human disease, and in particular, models of Alzheimer's disease and other neurodegenerative and amyloidosis-associated diseases. Transgenic animals include, but are not limited to rodents, including mice, rats and hamsters, sheep, goats, chickens, pigs, cattle, monkeys, primates and other non-human mammals.

Optionally, the animal can further exogenously express one or more other genes involved in the APP processing or degradation pathway, such as wild-type or mutant presenilin (PS-1 or PS-2), BACE, IDE and/or neprilysin, and/or one or more other genes involved in pathogenesis, such as tau.

The exogenous gene(s) can be expressed in all tissues or only in selected tissues (e.g. neural tissues), at any or all developmental stages, and at physiological, supra- or subphysiological levels, by appropriate choice of regulatory elements. Transgenic animals can further be homozygous, hemizygous, heterozygous or chimeric for the exogenous gene(s). Transgenic animals can contain the exogenous gene(s) as well as, or instead of (e.g. through "knock-in" methodology), the endogenous counterpart. Methods of producing transgenic animals are described in standard laboratory manuals including, for example, Hogan et al., (1994), Manipulating the Mouse Embryo: A Laboratory Manual, $2^{nd}$ ed., Cold Spring Harbor Laboratory, New York.

APP-expressing transgenic animals are known in the art, and include the Tg2576 mouse, which contains human APP695 with the Swedish (Lys670Asn, Met671Leu) double mutation under the control of the hamster prion protein gene promoter (Hsiao et al. (1996) *Science* 274:99-102; U.S. Pat. No. 5,877,399); the V717F PDAPP mouse, which contains human APP695 (Val717Phe) under the control of the platelet derived growth factor (PDGF) chain gene promoter (Games et al. (1995) *Nature* 373:523-527; U.S. Pat. No. 5,811,633); and the C100 mouse, which contains the neurotoxic C-terminal 100 amino acids of APP under the control of the dystrophin neural promoter (Neve et al. (1996) *Neurobiol. Aging* 17:191-203; U.S. Pat. Nos. 5,672,805). Additional APP-expressing transgenic animals are described, for example, in U.S. Pat. Nos. 5,612,486; 5,850,003; 5,387,742; 6,037,521; 6,184,435; 6,187,992; 6,211,428; and 6,340,783; and are reviewed by Emilien, et al., (2000) *Arch. Neuro.* 57:176-181.

C. Cells

Cells useful in evaluating compound activity can express, either endogenously or recombinantly, any desired wild-type or mutant APP and/or Aβ isoform, as described herein. Cells can be primary cells or cell lines derived from any animal, including humans and other mammals, such as transgenic animals described above. The cells can be of any differentiated lineage, such as neural lineage (e.g. cortical neural cells, microglia, glia, astrocytes), fibroblasts, lymphocytes and epithelial cells, or can be totipotent or pluripotent (see Freshney, R. I. (2000) "Culture of Animal Cells: A Manual of Basic Technique," $4^{th}$ ed., Wiley-Liss). An exemplary cell line suitable for assessing the activity of a compound in modulating Aβ is SH-SY5Y-APP751, which is described in the Example section herein. A further exemplary cell line is HGB, which expresses endogenous APP.

Exemplary primary cells suitable for assessing the activity of a compound in modulating Aβ are mixed brain cultures from Tg2576 transgenic mice, or other APP-expressing transgenic animals. Mixed brain cultures can be prepared, for example, by dissecting brain tissues from approximately 17-day old mouse embryos, dissociating the brain tissue with papain, and culturing the cells by standard procedures for primary neuronal cultures.

APP-, amyloid precursor fragment- or Aβ-encoding nucleic acid, under the control of suitable constitutive or inducible regulatory elements, can be transiently or stably introduced into primary cells or cell lines by various well-known transfection methods (Sambrook and Russell (2000) "Molecular Cloning: A Laboratory Manual" *Cold Spring Harbor Laboratory Press*; Ausubel et al. (eds.) (current edition) "Current Protocols in Molecular Biology" *John Wiley &Sons.*).

D. Assays that Directly Assess aβ Levels

Compounds can be evaluated for their ability to modulate Aβ using assays that directly assess the level of Aβ. Thus, the ability of a compound to modulate Aβ can be evaluated by determining the amount of a particular Aβ peptide (such as Aβ43, Aβ42, Aβ40, Aβ39, Aβ38, Aβ37, Aβ34, 11-43, 11-42, 11-40, 11-39, 11-38, 11-37, 11-34, etc.); by determining the amount of Aβ peptides collectively; by determining the amount of a particular Aβ peptide relative to the amount of a second Aβ peptide (such as the ratio of Aβ42 to Aβ40); by determining the amount, or relative amount, of Aβ in a particular form (such as monomeric, oligomeric, or fibrillar form; in solution or aggregated in a plaque; in a particular conformation, etc.); and/or by determining the amount, or relative amount, of Aβ in a particular location (such as intracellular, membrane-associated or extracellular, or in a particular tissue or body fluid).

Numerous methods are known in the art for determining the amount, or relative amount, of particular Aβ species or forms, or Aβ peptides collectively, in a sample. In such methods, the level of Aβ can optionally be quantified using internal standards and/or calibration curves generated by performing the assay with known amounts of standards.

For example, immunodetection methods can be used that employ Aβ-specific antibodies (e.g. monoclonal and polyclonal antibodies, single-chain antibodies, chimeric antibodies, bifunctional antibodies, humanized antibodies, CDR-grafted antibodies and CDR-grafted alternative scaffolds, as well as antigen-binding fragments thereof). Such antibodies can optionally be specific for particular Aβ species or forms. For instance, antibodies that bind an epitope at or near the N-terminus, C-terminus, or central portion of Aβ can be used to simultaneously detect multiple isoforms of Aβ. Exemplary antibodies include, but are not limited to, 6E10, B436, antibody raised against Aβ 12-28, 21F12, A387, Clone GB-10, and the Aβ40-selective antibodies. Moreover, antibodies selective for any desired epitope of any Aβ species can be readily prepared by well known methods described in the art.

Antibody or binding agent can optionally be detectably labeled or, if a secondary antibody or binding agent is employed, the secondary antibody or agent can be detectably labeled. Exemplary detectable labels include radioactive, fluorescent, bioluminescent, chemiluminescent and enzymatic labels. Methods of detecting such labels, and of quantitatively or qualitatively assessing the amount of bound peptide based on such detection, are well known in the art.

Immunodetection methods that can be adapted for assessing Aβ levels are well known to one of skill in the art. Representative methods include, but are not limited to, immunoprecipitation (optionally in combination with electrophoretic separation or a denaturing or non-denaturing gel, or mass spectroscopic analysis), western hybridization, immunocytochemistry, fluorescence resonance energy transfer (FRET)-based methods, and various formats of enzyme-linked immunosorbent assays (ELISA). For assessing any form of Aβ (e.g. whether the Aβ is in monomeric, oligomeric or fibrillar form, and its conformation), non-denaturing separation conditions (e.g. non-denaturing electrophoresis or chromatography) can be used. For assessing levels of particular species of Aβ, urea-bis-bicine-SDS based electrophoresis can be performed, which can resolve Aβ37, Aβ38, Aβ39, Aβ40, Aβ2-42, and Aβ3-42 species (Wiltfang et al., (2001) *J. Biol. Chem.*, 276: 42645-42657).

Immunodetection methods, such as those described above, can readily be adapted for use with non-antibody-based agents that bind Aβ, such as Aβ-binding proteins, fragments thereof, and small molecule compounds. Proteins and compounds that bind Aβ are known in the art or can be identified by routine screening assays.

Any method of determining the amount of Aβ deposited in tissues of live organisms, including imaging methods, such as multiphoton microscopy and positron emission tomography, can be employed. For example, imaging agents cross the blood-brain barrier and bind amyloid deposits with high affinity, such as the thioflavin-T analogue 2-[4'-(methylamino)phenyl]benzothiazole (Mathis et al. (2002) *Bioorg. Med. Chem. Lett.* 12:295-298) and the Congo red derivative methoxy-X04 (Klunk et al. (2002) *J Neuropathol. Exp. Neurol.* 61:797-805).

E. Assays that Indirectly Assess Aβ Levels

Compounds can alternatively be evaluated for their ability to modulate Aβ using assays that indirectly assess the level of Aβ. Those skilled in the art can determine suitable assays for evaluating modulation of Aβ levels. For example, the amount of uncleaved APP, or of a product of APP processing other than Aβ, can be assessed.

Thus, the ability of a compound to modulate the amount, or relative amount, of APP, and/or of a cleavage product of α-secretase (such as sAPPβ or C83), and/or of a product of the combined cleavage of α-secretase and γ-secretase (such as p3), and/or of a cleavage product of β-secretase (such as sAPPβ, C99, or C89), can be assessed. Methods of determining the amount of APP or of APP processing products are known in the art, and include immunodetection assays similar to those described above for Aβ, employing suitable antibodies.

The following examples are provided to further illustrate aspects of the invention. These examples are non-limiting and should not be construed as limiting any aspect of the invention.

EXAMPLES

All solvents and reagents were obtained from the Aldrich Chemical Company (Milwaukee, Wis.) unless otherwise indicated.

Structural characterization was conducted using $^1$H NMR spectroscopy. Proton nuclear magnetic resonance ($^1$H NMR) spectra were recorded on a Varian 300 MHz NMR spectrometer in deuterated chloroform (CDCl$_3$) or water (D$_2$O) using the residual $^1$H solvent peak as the internal standard.

Purified compounds were analyzed for correct mass and purity using an Applied Biosystems AP150X mass spectrometer coupled with a Shimadzu HPLC system. A typical gradient utilized a mobile phase of acetonitrile/water 1-99% over 4 min. 0.035 to 0.050% of trifluoroacetic acid was added to the mobile phase. Gradients were run at 7 ml/min through a Chromalith™ SpeedRod RP-18e, 4.6×50 mm column. Compound structure was confirmed by the observance of the (M+H$^+$) ion (M+1). Compound purity was assessed by ultraviolet light absorbance at wavelengths of 220 nm and 254 nm. The percent purity was based upon integration of the area under the peaks in the chromatogram.

Example 1

Preparation of Representative Alpha-Bromoketone Derivatives

Representative α-bromoketone derivatives were prepared for condensation with representative thioureas. Described below are exemplary procedures which were used for the synthesis of representative α-bromoketone derivatives.

A. 2-bromo-1-[4-(4-methyl-imidazole-1-yl)-phenyl]-ethanone (10)

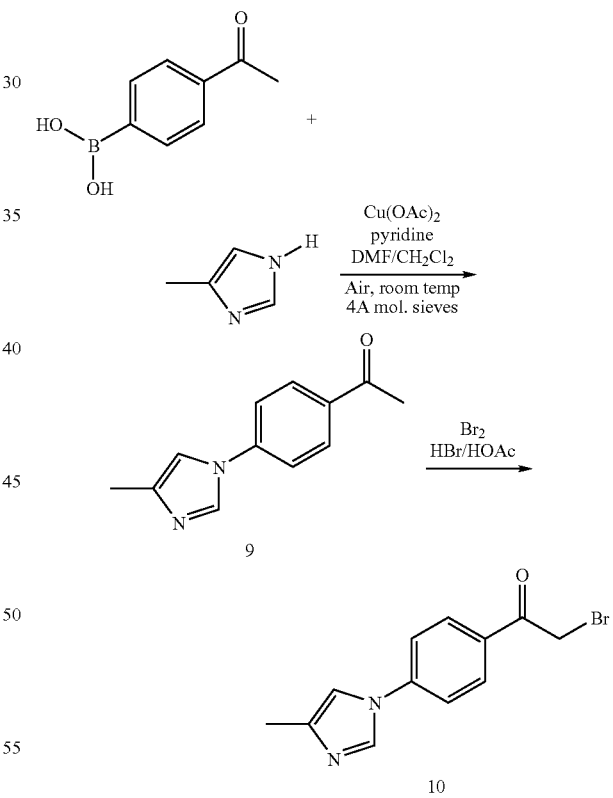

4-acetylphenyl boronic acid (820 mg, 5 mmol, 2.0 eq), and 4-methyl-1H-imidazole (205 mg, 2.5 mmol, 1.0 eq) were dissolved in 22 ml of DMF/CH$_2$Cl$_2$ solution (1:10) in a 100 mL round bottle flask. To this reaction mixture, anhydrous cupric acetate (681 mg, 3.75 mmol, 1.5 eq), 4 Å molecular sieves (1.875 g), and pyridine (0.4 ml, 5 mmol, 2.0 eq) were then added. The reaction was stirred under air at room temperature for 16 h, at which time the reaction was judged to be complete by LC-MS. The reaction was then filtered through Celite, washed with methanol and purified by silica gel chromatography (ISCO system, 0-5% methanol/ethylacetate) to Give compound 9 (200 mg, 40% yield).

Compound 9 (200 mg, 1 mmol) was dissolved in 30% by weight solution of hydrogen bromide in acetic acid (2 mL). To this solution, bromine (160 mg, 1 mmol) was added dropwise. The reaction was stirred at room temperature for 2 h. The reaction mixture was poured into ice-water (~5 g). The desired product precipitated out. The solid precipitate was filtered, washed with ice cold water, and then dried over a vacuum pump to give a yellow solid product 10 (120 mg, HOAc salt), which was carried on to subsequent steps without further purification.

B. 2-bromo-1-[4-(4-methyl-imidazole-1-yl)-phenyl]-propan-1-one (40)

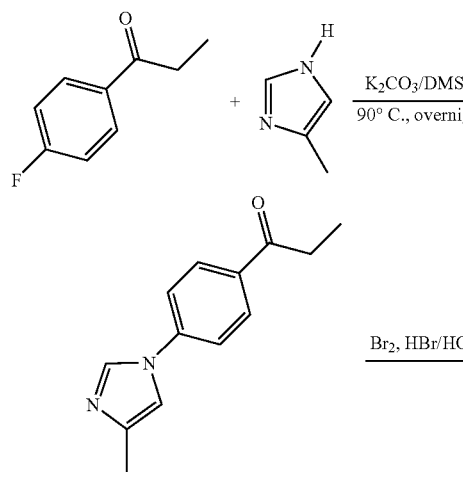

A solution of 4-methyl-imidazole (1.72 g, 21 mmol, 1.05 eq) and 1-(4-fluoro-phenyl)-propan-1-one (3.04 g, 20 mmol, 1.0 eq) in DMSO (15 ml) was stirred with anhydrous potassium carbonate (5.52 g, 40 mmol, 2.0 eq) at 90° C. overnight. At this point, the reaction was judged to be complete by LC-MS. On cooling, the reaction mixture was poured onto ice-water (~50 g). The desired product precipitated out, and the precipitate was filtered, washed with cold water and dried over a vacuum pump to give a light yellow solid product 11 (2.14 g, 50% yield). Compound II was brominated in a similar manner as described above to afford compound 12.

In a similar procedure as described above, 1-(3,4-difluoro-phenyl)-propan-1-one was reacted with 4-methyl-imidazole to give compound 13. Bromination of 13 in a manner as described above afforded {4-[3-Fluoro-4-(4-methyl-imidazol-1-yl)-phenyl]-thiazol-2-yl}-(5-isopropyl-4-methoxy-2-methyl-phenyl)-amine (14).

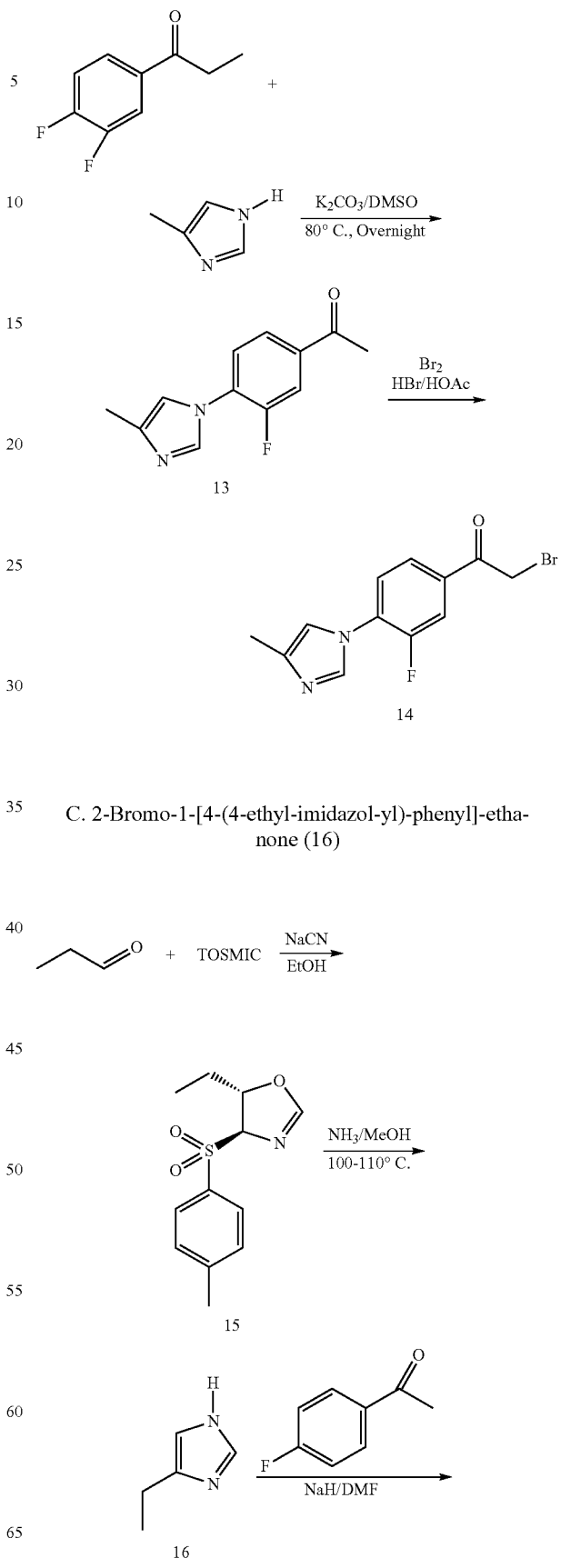

C. 2-Bromo-1-[4-(4-ethyl-imidazol-yl)-phenyl]-ethanone (16)

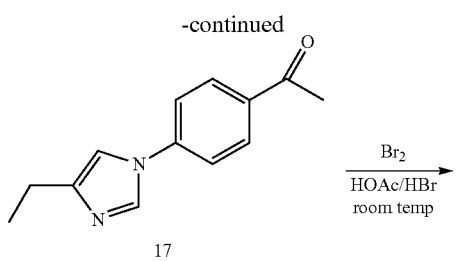

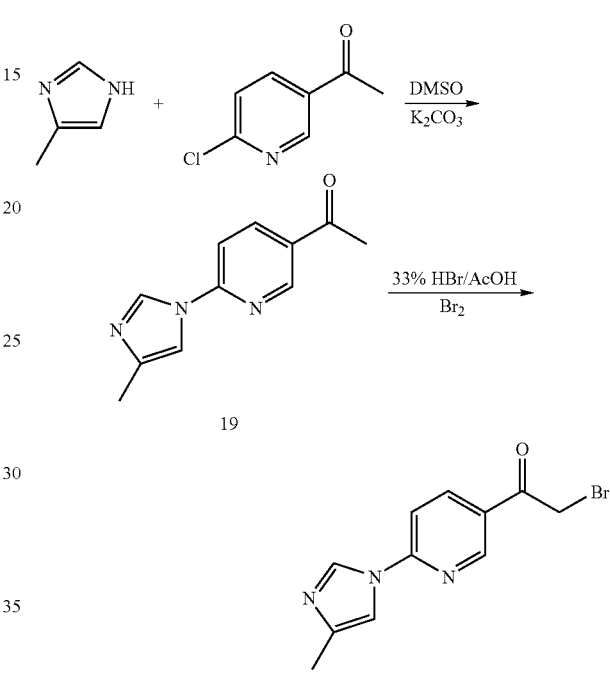

1. 5-Ethyl-4-tosyl-2-oxazoline (15)

To a stirred suspension of tosylmethylisocyanate (TosMIC, 3.90 g, 20 mmol) and propionaldehyde (1.5 mL 20.4 mmol) in 60 mL dry ethanol, finely powdered sodium cyanide (0.098 g, 2 mmol) was added. The reaction mixture became clear and white crystals of oxazoline began to precipitate in 15 min. The reaction was continuously stirred for an additional 30 min. The mixture was filtered and the crystals were washed with ether-hexane (1:1) before drying. Compound 15 was attained in 81% yield (4.1 g). The structure was confirmed by $^1$H NMR in CDCl$_3$. LC-MS: [M+1]=254. Purity was >98%.

2. 4-Ethylimidazole (16)

In a pressure flask, compound 15 was dissolved (1.1 g, 4.3 mmol) in a saturated solution of ammonia in dry methanol (30 mL). The reaction mixture was stirred for 18 h at 100-110° C. The solvent was evaporated and the product was purified by flash chromatography by elution with CH$_2$Cl$_2$-MeOH. Compound 16 was isolated as a light yellow oil (yield 72%, 0.3 g). The structure was confirmed by $^1$H NMR in CDCl$_3$ and purity by TLC in CH$_2$Cl$_2$-MeOH (9:1). Purity was >95%.

3. 1-[4-(4-Ethyl-imidazol-1-yl)-phenyl]-ethanone (17)

NaH (0.068 g in 60% oil dispersion, 1.7 mmol) was added to a solution of compound 16 (0.180 g, 1.8 mmol) in DMF (6 mL) with stirring at room temperature. The mixture was stirred for 15 min and a solution of 4'-fluoroacetophenone (0.215 g, 1.56 mmol) in DMF (2 mL) was added. The reaction mixture was heated at 80° C. for 1 h, and then cooled, diluted with water, and extracted with EtOAc. The organic layer was washed with brine, dried, and evaporated to a yellow solid. Compound 17 crystallized to form white color needles upon standing at room temperature. The yield was 0.270 g, 67%. The structure was confirmed by $^1$H NMR in CDCl$_3$. LC-MS: [M+1]=215. Purity was >98%.

4. 2-Bromo-1-[4-(4-ethyl-imidazol-yl)-phenyl]-ethanone (18)

Ketone 17 (0.160 g, 0.66 mmol) was dissolved in 30% acetic acid/HBr (5 mL) before addition of bromine (0.104 g, 0.66 mmol). The reaction mixture was stirred at room temperature for 1 h, and then poured into cold water (10 mL). The product was extracted with ethylacetate (20 mL). The combined organic layers were washed with water and brine, dried, evaporated to a yellow solid, and crystallized from ethylacetate: hexane (1:1) to yield 0.170 g (77%) of compound 18. The structure was confirmed by $^1$H NMR in CDCl$_3$. LC-MS: [M+1]=294. Purity was >95%.

D. 2-bromo-1-[6-(4-methyl-imidazole-1-yl)-pyridin-3-yl]-ethanone (20)

1. 1-[6-(4-methyl-imidazole-1-yl)-pyridin-3-yl]-ethanone (19)

1-(6-chloro-pyridin-3-yl)-ethanone (7.00 g, 45.16 mmol) and 4-methylimidazole (11.11 g, 135.50 mmol) were combined in DMSO (35 ml), before addition of K$_2$CO$_3$. The mixture was heated at 110° C. for 22 h with rapid stirring. The reaction was then cooled to room temperature and poured into ice water (400 ml) with vigorous stirring for 15 min. The resulting precipitate was collected on a filter and washed generously with water. The resulting material was dried in vacuo to yield 19 as a tan solid (6.1 g, 67%). LC/MS: [M+1]$^+$= 202.2. C$_{11}$H$_{11}$N$_3$O=201.2. $^1$H NMR (DMSO-d6) 300 MHz δ2.18 (3H, s), 2.63 (3H, s), 7.72 (1H, s), 7.87 (2H, d, J=9.0 Hz), 8.41 (2H, d, J=9.0 Hz), 8.51 (1H, s), 8.98 (1H, s).

2. 2-bromo-1-[6-(4-methyl-imidazole-1-yl)-pyridin-3-yl]-ethanone (20)

Compound 19 (6.1 g, 30.30 mmol) was suspended in 30% HBr/AcOH (75 ml). Bromine (4.82 g, 30.30 mmol) was added dropwise over 1 h. The reaction was stirred for 2 h at room temperature. The reaction mixture was poured into 600 mL of ice water and stirred rapidly for 15 min. The resulting precipitate was collected on a filter and washed with water. The compound was air dried to yield 20 as a yellow solid (10.6 g, 80%). LC/MS: [M+1]$^+$=281.1. $C_{11}H_{10}BrN_3O$:2HBr=442.0. $^1$H NMR (DMSO-d6) 300 MHz δ2.36 and 2.37 (6H, two s), 5.06 (2H, s), 8.16 (1H, d, J=9.0 Hz), 8.29 (1H, s), 8.69 (1H, d, J=9.0 Hz), 9.15 (1H, s), 9.93 (1H, s).

E. 1-[4-(5-bromo-thiazol-2-yl)-phenyl]-ethanone (1221) and 2-Bromo-1-[4-(5-bromo-thiazol-2-yl)-phenyl]-ethanone (1222)

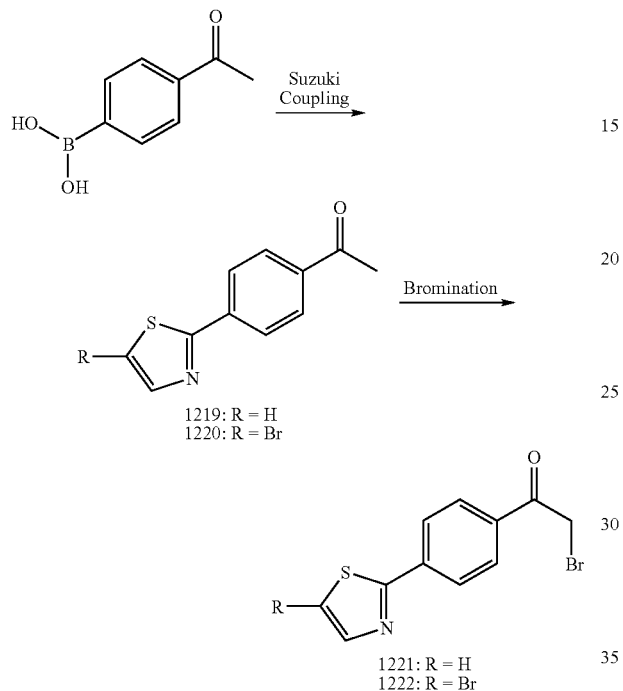

1. 1-[4-(5-bromo-thiazol-2-yl)-phenyl]ethanone (1221)

2-bromo thiazole (1 g, 6.1 mmol) was placed in a flask and toluene:EtOH (4:1, 80 mL:20 mL) was added prior to the addition of 4-acetylphenyl boronic acid (1.2 g, 7.32 mmol), sodium carbonate (2.16 g, 20.4 mmol), and water (3 mL). The reaction mixture was degassed by bubbling nitrogen through it for 30 min. Pd(PPh$_3$)$_4$ was subsequently added and the reaction mixture was heated at 80° C. for 17 h before it was allowed to cool to room temperature. EtOAc (3×100 mL) and water (100 mL) were added. The organic extracts were washed with water (100 mL), brine (100 mL), dried over MgSO$_4$, filtered, and purified by column chromatography (120 g ISCO cartridge). Compound 1219 was isolated as a white powder (974 mg, 79%, mass for $C_{11}H_9NOS$, calculated: 203.3, observed: 204.2 [M+1]). Compound 1219 (204 mg, 1 mmol) was dissolved in 30% HBr in acetic acid (3 mL) before bromine (160 mg, 1 mmol) was added dropwise. The reaction mixture was stirred at room temperature for 6 h before it was poured onto ice-water, stirred for 10 min and the precipitate filtered. Compound 1221 was isolated as a yellow powder (257 mg, 92%, mass for $C_{11}H_9BrNOS$, calculated: 281.2, observed: 282.1 [M+1]).

2. 2-bromo-1-[4-(5-bromo-thiazol-2-yl)-phenyl]-ethanone (1222)

Using the same procedure as described above, compound 1220 was prepared by starting with 2,5-dibromothiazole (809 mg, 4.94 mmol). 1-[4-(5-bromo-thiazol-2-yl)-phenyl]-ethanone 1220 was isolated as pale yellow powder (500 mg, 43%, mass for $C_{11}H_8BrNOS$, calculated: 283.2, observed: 284.1 [M+1]). 2-Bromo-1-[4-(5-bromo-thiazol-2-yl)-phenyl]-ethanone 1222 was isolated as a pale yellow powder (436 mg, 77%, mass for $C_{11}H_7BrNOS$, calculated: 360.1, observed: 361.6 [M+1]).

The following α-bromoketone derivatives listed below in Table 1 are an exemplary illustration of all prepared bromoketone compounds.

TABLE 1

| Compound No. | α-bromoketone |
|---|---|
| 10 | ![structure] |
| 12 | ![structure] |
| 14 | ![structure] |
| 18 | ![structure] |
| 20 | ![structure] |

TABLE 1-continued

| Compound No. | α-bromoketone |
|---|---|
| 21 | (4-(1H-imidazol-1-yl)-3-fluorophenyl α-bromoketone) |
| 22 | (4-(1H-imidazol-1-yl)phenyl α-bromoketone) |
| 23 | (6-(1H-imidazol-1-yl)pyridin-3-yl α-bromoketone) |
| 24 | (4-(4,5-dichloro-1H-imidazol-1-yl)phenyl α-bromoketone) |
| 25 | (4-(4-methyl-1H-pyrazol-1-yl)phenyl α-bromoketone) |
| 26 | (4-(2-methyl-1H-imidazol-1-yl)phenyl α-bromoketone) |
| 27 | (4-azidophenyl α-bromoketone) |
| 28 | (6-(4-bromo-1H-imidazol-1-yl)pyridin-3-yl α-bromoketone) |
| 1221 | (4-(thiazol-2-yl)phenyl α-bromoketone) |
| 1222 | (4-(5-bromothiazol-2-yl)phenyl α-bromoketone) |

Example 2

Preparation of Thiourea Urea Derivatives

Thiourea derivatives were prepared by combining an aniline derivative with an aryl isothiocyanate derivative. Most aniline compounds were commercially available and/or synthesized used well known methods.

An exemplary aniline, 5-(N,N-diethylamino)-2-methyl-aniline, was prepared according to the following representative route. This procedure was also employed to synthesize other 5-(N,N-diethylamino)-2-methyl-aniline analogs.

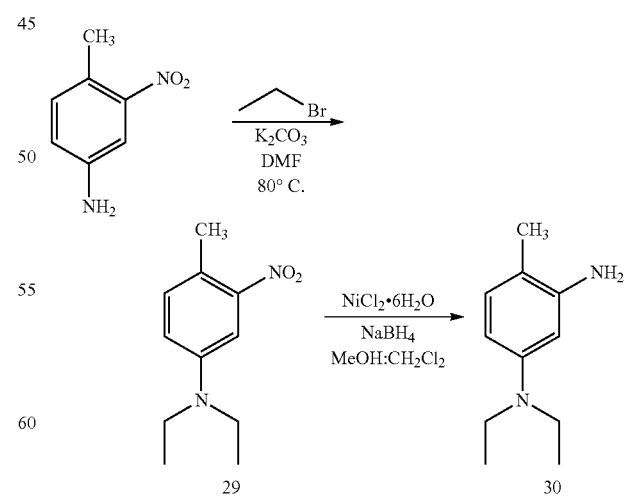

Compound 29, diethyl-(4-methyl-3-nitrophenyl)-amine was prepared by dissolving 4-methyl-3-nitroaniline (25.0 g, 164.5 mmol) and ethyl bromide (44.8 g, 411.2 mmol) in DMF in a 350 mL glass bomb. A large stir bar and K$_2$CO$_3$ (56.75 g, 411.2 mmol) were added. The bomb was tightly capped and placed in an oil bath at 80° C. The mixture was then vigorously stirred for 40 h. The reaction was then cooled and uncapped, and the material was partitioned between EtOAc (400 mL) and water (300 mL). The water layer was then washed twice with EtOAc (150 mL) and the combined EtOAc layers were washed twice with water (500 mL) and once with brine (500 mL). The EtOAc layer was then dried over MgSO$_4$, filtered and concentrated to a dark liquid. The product was purified by silica gel chromatography with 5% EtOAc/hexanes. Pure fractions were concentrated to yield compound 29 as an orange liquid (20.8 g, 61%). LC/MS: [M+H]$^+$=209.1. C$_{11}$H$_{16}$N$_2$O$_2$=208.2. $^1$H NMR (CDCl$_3$) 300 MHz δ1.16 (t, 6H, J=6.9 Hz), 2.44 (s, 3H), 3.35 (q, 4H, J=6.9 Hz), 6.76 (two d, 1H, J=3.0 Hz), 7.09 (two d, 1H, J=0.6 Hz), 7.25 (d, 1H, J=3.0 Hz).

Compound 29 (20.8 g, 100.0 mmol) was dissolved in MeOH: CH$_2$Cl$_2$ and cooled to 0° C. in an ice bath. NiCl$_2$.6H$_2$O (4.0 g, 16.8 mmol) and NaBH$_4$ (11.0 g, 297.3 mmol) were added in 1 g portion over 90 min. TLC confirmed reaction completion. The solvent was removed under reduced pressure and the material was re-suspended in CH$_2$Cl$_2$ (500 mL) and silica gel. The solvent was then removed under reduced pressure until material appeared as a loose grey powder. The powder was placed into a funnel and generously washed with EtOAc (500 mL). The resulting solution was concentrated to a yellow liquid which was purified on a silica gel column eluted with 30% EtOAc/hexanes. Pure fraction were combined and concentrated under reduced pressure to yield compound 30 as a light purple liquid (15.3 g, 85%). LC/MS: [M+H]$^+$=179.2. C$_{16}$H$_{18}$N$_2$=178.2. $^1$H NMR (CDCl$_3$) 300 MHz δ1.13 (t, 6H, J=6.9 Hz), 2.04 (s, 3H), 3.27 (q, 4H, J=6.9 Hz), 3.51 (broad s, 2H), 6.05 (d, 1H, J=2.4 Hz), 6.11 (two d, 1H, J=2.4 Hz), 6.86 (d, 1H, J=8.1 Hz).

The following representative thiourea derivatives were prepared for condensation with representative α-bromoketones. Listed below are exemplary procedures that were employed in the preparation of thiourea derivatives.

A. 2-methyl-5-pyrrol-1-yl-phenyl-thiourea (32)

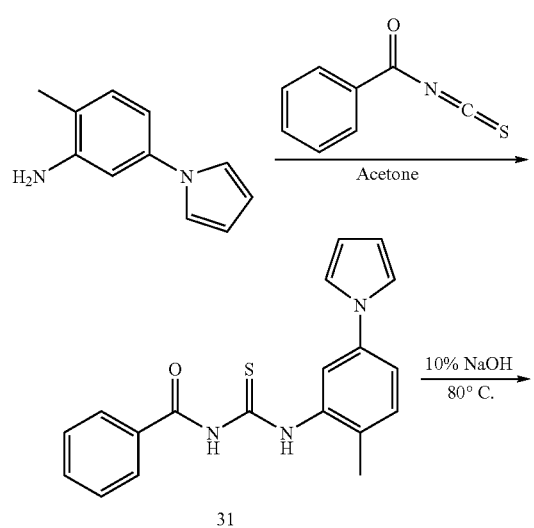

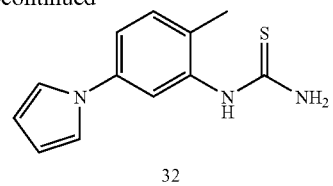

32

To benzoyl isothiocyanate (6.4 mmol, 1.04 g) in 10 mL dry acetone, 2-methyl-5-pyrrol-1-yl-phenylamine was added rapidly with stirring. The reaction was stirred for 2 h at 40° C., and then poured into excess cracked ice with vigorous stirring. The resulting solid was collected, liberally washed with cold water followed by hexane, and then air-dried. The product 31 (90% yield) was used directly for the next step reaction without further purification.

Compound 31 was added in one portion to a preheated (~80° C.) stirring solution of 10% aq NaOH. After stirring overnight, the mixture was poured onto excess ice. The pH value was adjusted to 5-6 with conc. HCl. The resulting co-precipitate of benzoic acid and the desired product 32 were collected and washed with cold water, then hexane to remove benzoic acid. The product was air-dried (80% yield) and carried on to subsequent reactions without further purification.

B. 4-hydroxy-2,5-dimethyl-phenyl-thiourea (34)

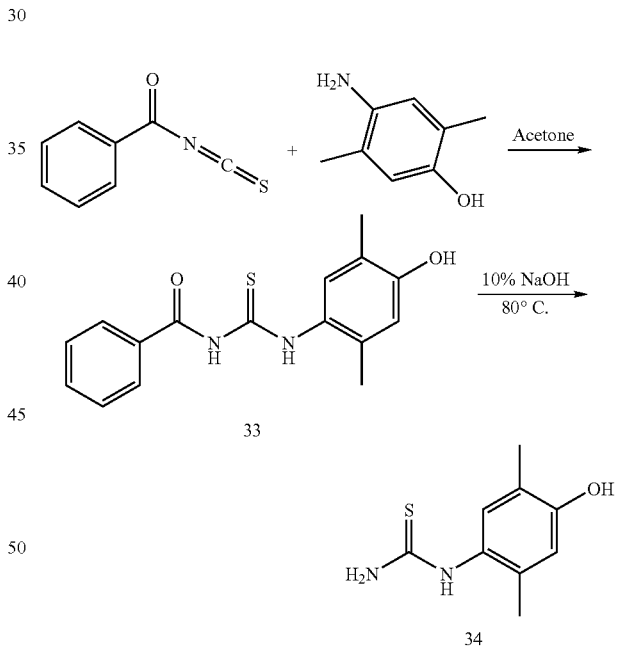

To benzoyl isothiocyanate (33 mmol, 5.38 g) in 30 mL dry acetone the aniline was added rapidly with stirring. The reaction was stirred for 1 h at 40° C., then poured onto excess cracked ice with vigorous stirring. The resulting solid was collected and liberally washed with cold water followed by hexane, then air-dried. The product 33 (over 80% yield) was used directly for the next step reaction without further purification.

Compound 33 was added in one portion to a preheated (~80° C.) stirring solution of 10% aq. NaOH. After stirring overnight, the mixture was poured onto excess ice. The pH value was adjusted to 5-6 with conc. HCl. The resulting co-precipitate of benzoic acid and the desired product 34 were collected and washed with cold water, then hexane to remove benzoic acid. The product was air-dried (~80% yield) and used for subsequent reactions without further purification.

C. (4-ethoxy-2,5-dimethyl-phenyl)-thiourea (39)

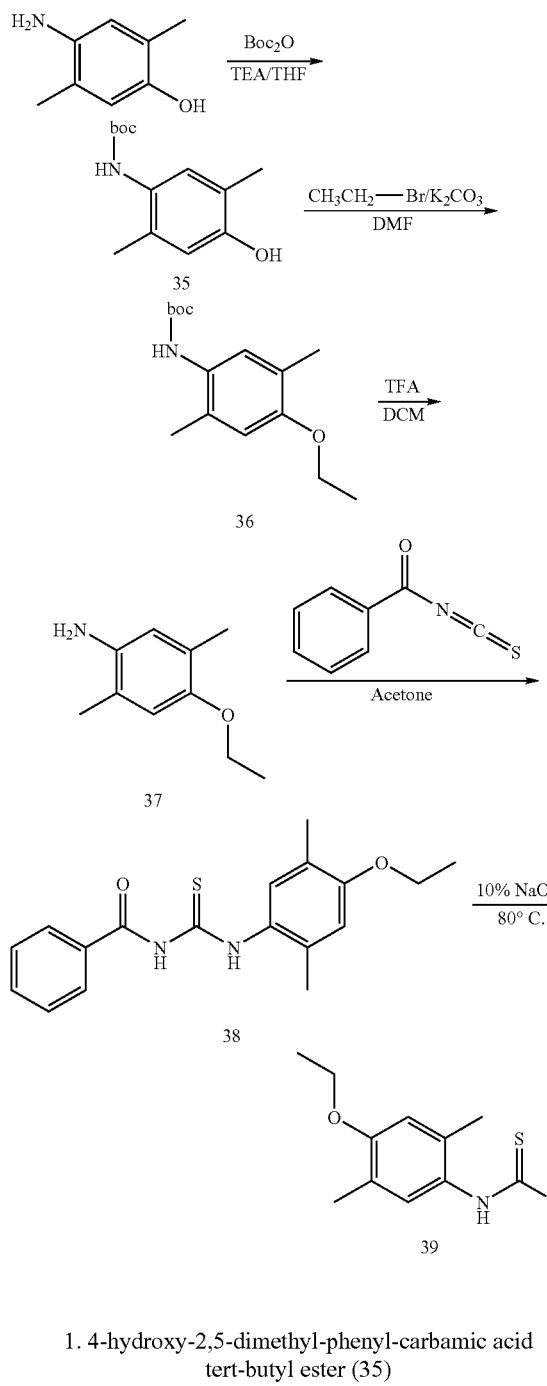

1. 4-hydroxy-2,5-dimethyl-phenyl-carbamic acid tert-butyl ester (35)

To a solution of 4-amino-2,5-dimethyl-phenol (20 mmol, 2.74 g) in 40 mL THF, Boc anhydride (22 mmol, 4.8 g) and TEA (30 mmol, 4.17 mL) were added respectively. After stirring at room temperature overnight, the reaction mixture was concentrated to remove THF, and the residue was re-dissolved in water (50 mL) and ethyl acetate (80 mL). The aqueous layer was extracted with ethyl acetate (3×50 mL). The combined organic layers were dried over $Na_2SO_4$. After removal of the solvent, the crude product was purified by flash chromatography (ISCO system, 5-40% ethyl acetate/hexane) to give the title compound 35 (90% yield).

2. (4-ethoxy-2,5-dimethyl-phenyl)-carbamic acid tert-butyl ester (36)

To a solution of compound 35 (4 mmol, 948 mg) in 5 mL DMF, potassium carbonate ($K_2CO_3$, 8 mmol, 1.1 g) and bromoethane (4.8 mmol, 523 mg) were added. The reaction was stirred overnight at 60° C. Water (2 mL) was added to dissolve the unreacted potassium carbonate, and the reaction mixture was then extracted with ethyl acetate (3×10 mL). The organic layers were combined and dried over $Na_2SO_4$. After removal of the solvent, the crude product was purified by using flash chromatography (0-30% ethyl acetate/hexane) to give the title product 36 (90% yield).

3. 4-ethoxy-2,5-dimethyl-phenylamine (37)

To a solution of 36 (950 mg, 3.6 mmol) in 10 mL dichoromethane, trifloroacetic acid (5 mL) was added. The reaction mixture was stirred for 2 h. At this point, LC-MS showed the reaction to be complete. The reaction flask was concentrated to remove the solvent and most of the TFA. The residue was then dried further in a high vacuum oven over 24 h to give the title compound 37 as TFA salt.

Compound 38 and 39 were synthesized using synthetic procedures described above for the preparation of compounds 33 and 34.

D. N,N-diethyl-2,5-dimethyl-benzene-1,4-diamine-thiourea (44)

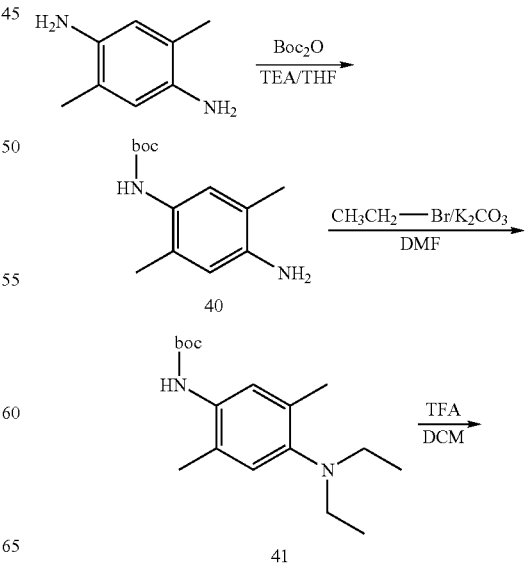

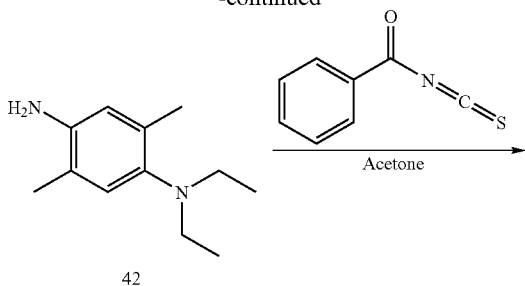

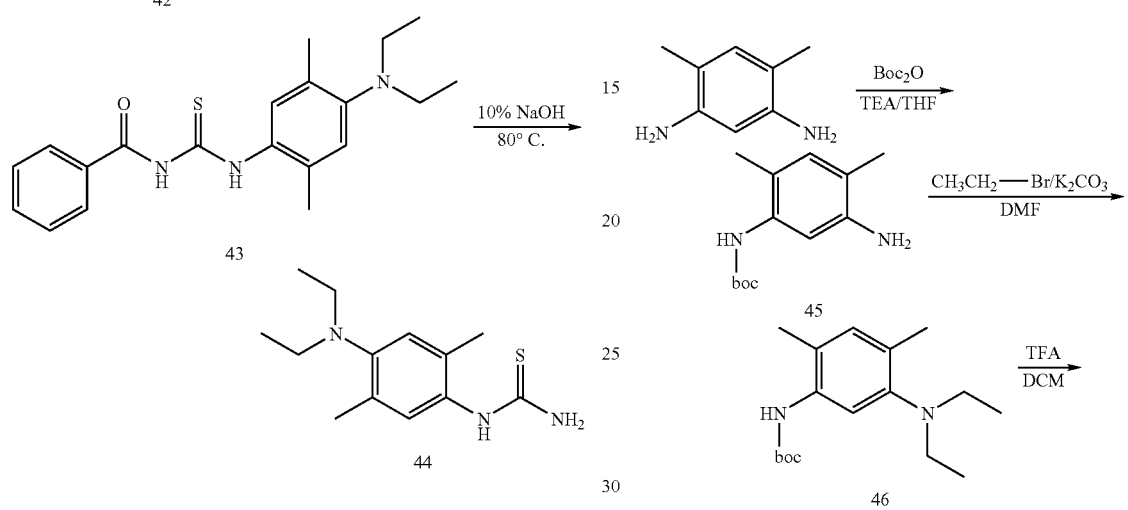

The reaction was concentrated to remove the solvent and most of the TFA. The residue was then dried further in a high vacuum oven over 24 h to give the title compound 42 as TFA salt (100% yield).

Compounds 43 and 44 were synthesized from 42 using similar synthetic procedures described above for the preparation of compounds 33 and 34.

E. N,N-diethyl-4,6-dimethyl-benzene-1,3-diamine-thiourea (49)

1. (4-Amino-2,5-dimethyl-phenyl)-carbamic acid tert-butyl ester (40)

To a solution of 2,5-dimethyl-benzene-1,4-diamine (30 mmol, 4.1 g) in 40 mL THF, boc anhydride (33 mmol, 72 g) and TEA (45 mmol, 6.26 mL) were added respectively. After stirring at room temperature overnight, the reaction mixture was concentrated to remove THF, and the residue was re-dissolved in water and ethyl acetate. The aqueous layer was extracted with ethyl acetate (3×80 mL). The organic layers were combined and dried over $Na_2SO_4$. After removal of the solvent, the crude product was purified by using flash chromatography (5-50% ethyl acetate/hexane) to give the title compound 40 (over 90% yield).

2. (4-diethylamino-2,5-dimethyl-phenyl)-carbamic acid tert-butyl ester (41)

To a solution of 40 (5 mmol, 1.18 g) in 3 mL DMF, potassium carbonate ($K_2CO_3$, 15 mmol, 2.07 g) and bromoethane (12.5 mmol, 1.36 g, 0.93 mL) were added. The reaction was stirred overnight at 70° C. Water (3 mL) was added to dissolve the unreacted potassium carbonate, and the reaction mixture was extracted with ethyl acetate (3×10 mL). The organic layers were combined and dried over $Na_2SO_4$. After removal of the solvent, the crude product was purified by using silica gel chromatography (0-30% ethyl acetate/hexane) to give the title compound 41 (75% yield).

3. N,N-diethyl-2,5-dimethyl-benzene-1,4-diamine (42)

To a solution of 41 in 2 mL dichoromethane, trifloroacetic acid (1 mL) was added. The reaction mixture was stirred for 2 h. At this point, LC-MS showed the reaction to be complete.

1. (5-Amino-2,4-dimethyl-phenyl)-carbamic acid tert-butyl ester (45)

To a solution of 2,6-dimethyl-benzene-1,3-diamine (30 mmol, 4.1 g) in 40 mL THF, boc anhydride (33 mmol, 7.2 g)

and TEA (45 mmol, 6.26 mL) were added respectively. After stirring at room temperature overnight, the reaction mixture was concentrated to remove THF, and the residue was re-dissolved in water and ethyl acetate. The aqueous layer was extracted with ethyl acetate (3×80 mL). The organic layers were combined and dried over $Na_2SO_4$. After removal of the solvent, the crude product was purified by using flash chromatography (5-50% ethyl acetate/hexane) to give the title compound 45 (95% yield).

2. (5-diethylamino-2,4-dimethyl-phenyl)-carbamic acid tert-butyl ester (46)

To a solution of 45 (5 mmol, 1.18 g) in 3 mL DMF, potassium carbonate ($K_2CO_3$, 15 mmol, 2.07 g) and bromoethane (12.5 mmol, 1.36 g, 0.93 mL) were added. The reaction was stirred overnight at 70° C. Water (3 mL) was added to dissolve the unreacted potassium carbonate, and the reaction mixture was then extracted with ethyl acetate (3×10 mL). The organic layers were combined and dried over $Na_2SO_4$. After removal of the solvent, the crude product was purified by using flash chromatography (0-30% ethyl acetate/hexane) to give the title compound 46 (80% yield).

3. N,N-diethyl-4,6-dimethyl-benzene-1,3-diamine (47)

To a solution of 46 (1.16 g, 4.0 mmol) in 10 mL dichoromethane, trifloroacetic acid (5 mL) was added. The reaction mixture was stirred for 2 h. At this point, LC-MS showed the reaction to be complete. The reaction was concentrated to remove the solvent and most of the TFA. The residue was then dried further in a high vacuum oven over 24 h to give the title compound 46 as a TFA salt (100% yield).

Compounds 48 and 49 were synthesized from 47 using similar synthetic procedures described above for the preparation of compounds 33 and 34.

F. 2-methyl-5-bromophenyl thiourea (50)

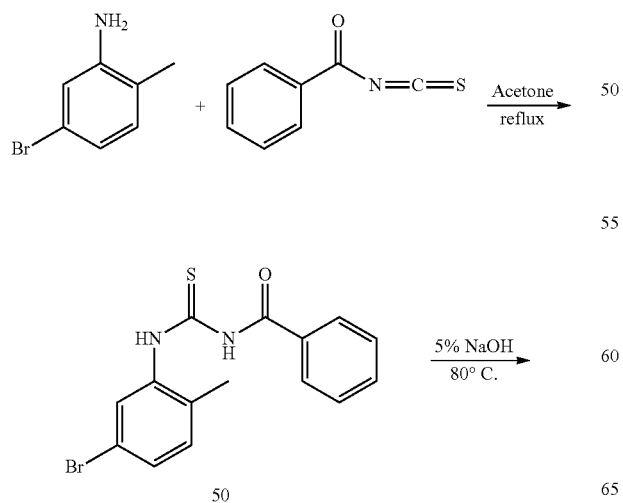

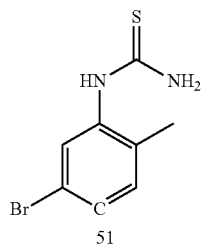

2-methyl-5-bromoaniline (10.8 g, 58.4 mmol) and benzoyl isothiocyanate (9.5 g, 58.4 mmol) were combined in acetone and heated to reflux for 30 min. The reaction was allowed to cool and then poured into stirring ice water. The mixture was stirred for 15 min, and then formed a precipitate, which was filtered and air dried within vacuum for 1 h. The resulting yellow powder was then suspended in a 5% NaOH aqueous solution and stirred for 18 h at 80° C. The reaction was allowed to cool and then poured into stirring ice water (400 ml). After stirring on ice for 1 h, the resulting white solid was vacuum filtered and air vacuum filter dried for 1 h, to yield compound 51 as a white solid (10.1 g, 71%). LC/MS: [M−H]−= 244.1. $C_8H_9BrN_2S$=245.1. $^1H$ NMR (DMSO-d6) 300 MHz δ 2.14 (s, 3H), 7.17 (d, 1H, J=8.4 Hz), 7.31 (d. 1H, J=7.8 Hz) 7.45 (s, 1H), 9.24 (broad s, 1H).

The following thiourea urea derivatives listed below in Table 2 are an exemplary collection of all prepared thiourea compounds.

TABLE 2

| Compound No. | Urea/Thiourea |
|---|---|
| 32 | 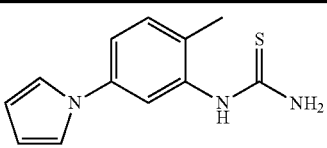 |
| 34 | 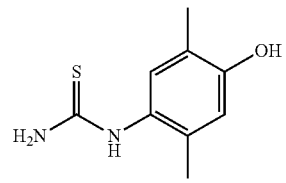 |
| 39 | 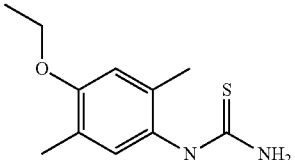 |
| 44 | 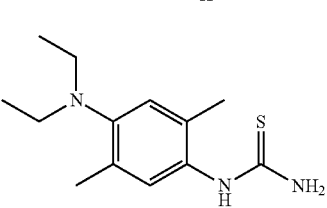 |

TABLE 2-continued
| Compound No. | Urea/Thiourea |
|---|---|
| 49 | 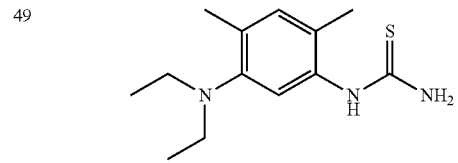 |
| 51 | 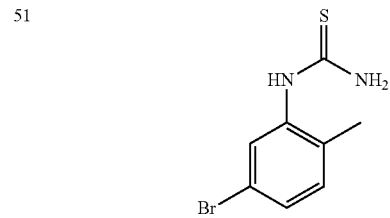 |
| 52 | 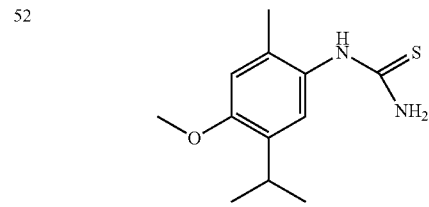 |
| 53 | 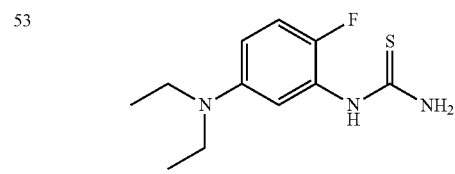 |
| 54 | 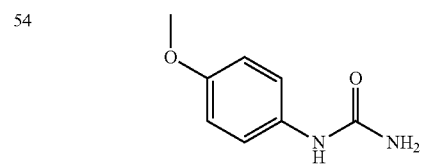 |
| 55 | 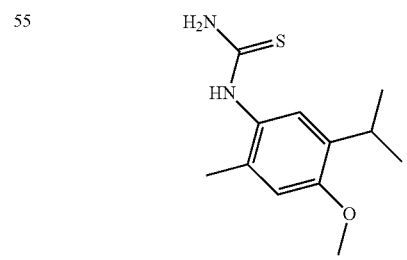 |
| 58 | 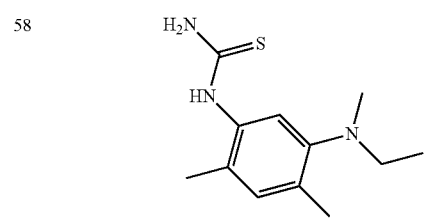 |
TABLE 2-continued
| Compound No. | Urea/Thiourea |
|---|---|
| 59 | 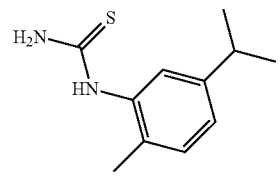 |
| 60 | 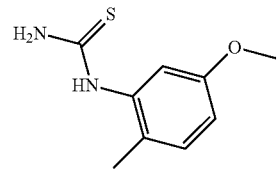 |
| 61 | 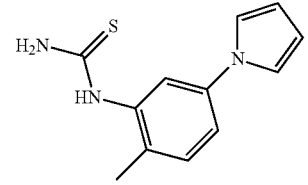 |
| 62 | 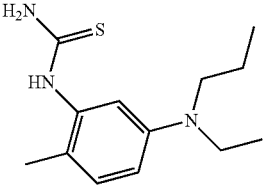 |
| 63 | 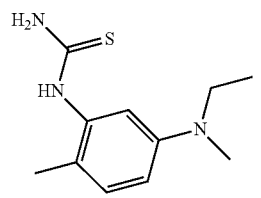 |
| 64 | 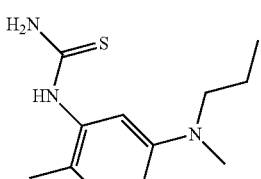 |
| 65 | 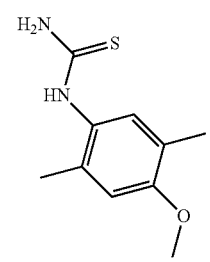 |

TABLE 2-continued

| Compound No. | Urea/Thiourea |
|---|---|
| 66 | 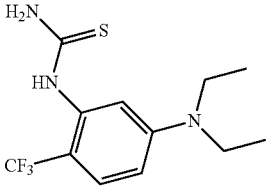 |
| 67 | 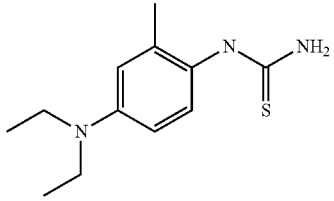 |

Example 3

Condensation of Representative Alpha-Bromoketones with Exemplary Thioureas

Representative α-bromoketone derivatives (0.08 mmol; see "bromoketone" column in Table 3 below) were combined with 4-diethylamino-2-methyl-phenyl-thiourea 67 (0.08 mmol) in 1 mL DMF solution. The reaction was stirred at 70° C. for 4 h-6 h with optional vortexing. After cooling to room temperature, the reaction mixture was directly injected into a reversed phase HPLC (Gilson 215) using an acetonitrile/water/TFA gradient in a $C_{18}$ column to isolate the title product. Title products were concentrated in vacuo as a TFA salt.

TABLE 3

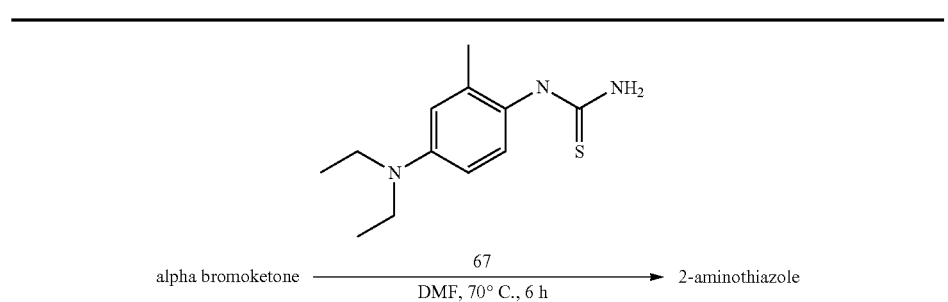

alpha bromoketone $\xrightarrow[\text{DMF, 70° C., 6 h}]{67}$ 2-aminothiazole

| Bromoketone | Title Product | LC-MS |
|---|---|---|
| 10 | 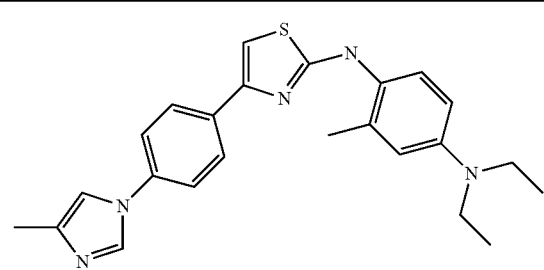 68 | observed [M + 1] = 418.4<br>calculated [M + 1] = 418.6 |
| 12 | 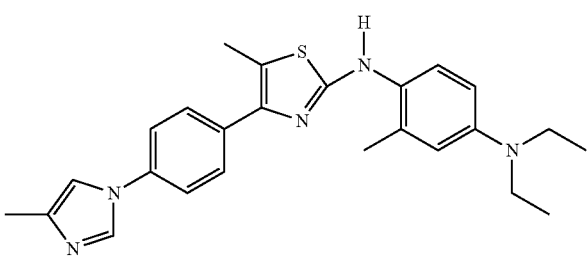 69 | observed [M + 1] = 432.5<br>calculated [M + 1] = 432.6 |

TABLE 3-continued
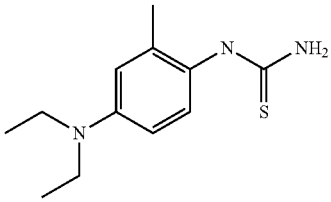
alpha bromoketone $\xrightarrow[\text{DMF, 70° C., 6 h}]{67}$ 2-aminothiazole
| Bromoketone | Title Product | LC-MS |
|---|---|---|
| 18 | 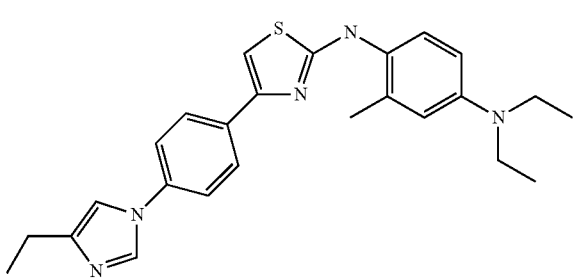<br>70 | observed [M + 1] = 432 |
| 24 | 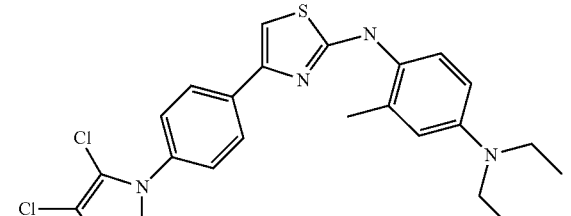<br>71 | observed [M + 1] = 472.2<br>calculated [M + 1] = 472.4 |
| 25 | 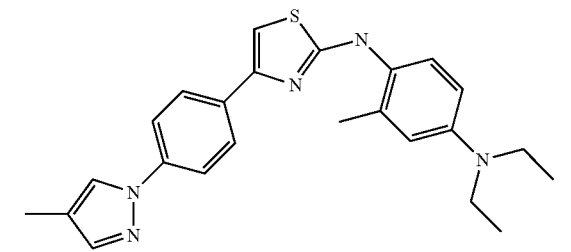<br>72 | observed [M + 1] = 418.4<br>calculated [M + 1] = 418.6 |
| 26 | 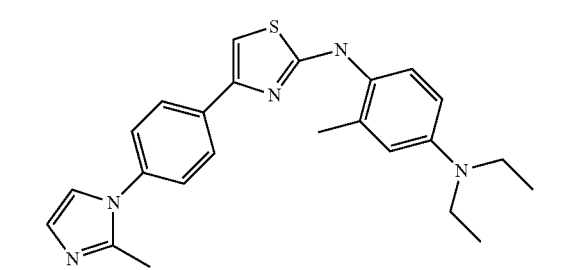<br>73 | observed [M + 1] = 418.4<br>calculated [M + 1] = 418.6 |

The following {4-[6-(4-methyl-imidazol-1-yl)-pyridin-3-yl]-thiazol-2-yl}-(2-methyl-5-pyrrol-1-yl-phenyl)-amine and representative analogs thereof were prepared in a similar procedure as described above. Generally, 0.1 mmol of 32 was dissolved in 1 ml DMF solution with various alpha bromoketone derivatives (sec "bromoketone" column of Table 4 below). The reaction was stirred at 70° C. for 6 h. After cooling to room temperature, the reaction mixture was purified by reversed phase HPLC using acetonitrile/water/TFA gradient and C18 stationary phase. The product was isolated and then concentrate to give the title compound as a TFA salt.

TABLE 4 alpha bromoketone + 32 →(DMF, 70° C.) aminothiazole

| Bromoketone | Title Product | LC-MS |
|---|---|---|
| 10 | 74 | observed [M + 1] = 412.4<br>calculated [M + 1] = 412.5 |
| 12 | 75 | observed [M + 1] = 427.4<br>calculated [M + 1] = 427.6; |
| 20 | 76 | observed [M + 1] = 413.4<br>calculated [M + 1] = 413.5 |

TABLE 4-continued

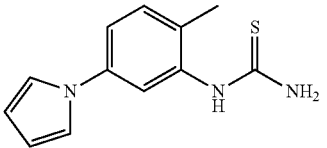

alpha bromoketone $\xrightarrow[\text{DMF}]{32}$ aminothiazole
$\quad$ 70° C.

| Bromoketone | Title Product | LC-MS |
|---|---|---|
| 28 | 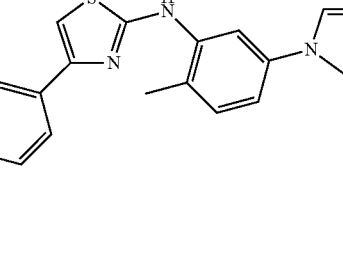  77 | observed [M + 1] = 476.2 & 478.2 calculated [M + 1] = 477.4 |

Various representative N,N-diethyl-2,5-dimethyl-N'-{4-[4-(4-methyl-imidazol-1-yl)-phenyl]-thiazole-2-yl}-benzene-1,4-diamine compounds and exemplary analogs thereof were prepared according to the same procedure as described above. Representative bromoketones employed in this reaction and the resultant title compounds afforded are listed below in Table 5.

TABLE 5

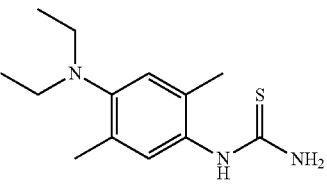

alpha bromoketone $\xrightarrow[\text{DMF}]{44}$ aminothiazole
$\quad$ 70° C.

| Bromoketone | Title Product | LC-MS |
|---|---|---|
| 10 | 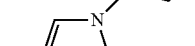  78 | observed [M + 1] = 432.4 calculated [M + 1] = 432.6 |

TABLE 5-continued

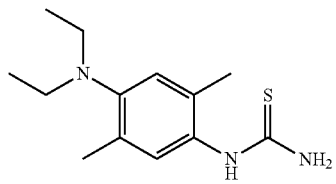

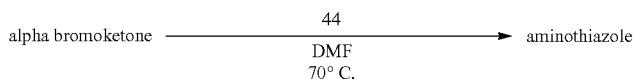

| Bromoketone | Title Product | LC-MS |
|---|---|---|
| 20 | 79 | observed [M + 1] = 433.4<br>calculated [M + 1] = 433.6 |
| 23 | 80 | observed [M + 1] = 418.4<br>calculated [M + 1] = 418.6 |

Various representative N,N-diethyl-4,6-dimethyl-N'-{4-[4-(4-methyl-imidazol-1-yl)-phenyl]-thiazole-2-yl}-benzene-1,3-diamine compounds and exemplary analogs thereof were prepared according to the same procedure as described above. Representative bromoketones employed in this reaction and the resultant title compounds afforded are listed below in Table 6.

TABLE 6

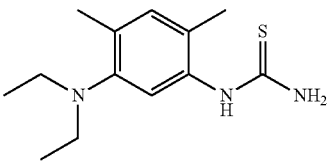

alpha bromoketone  →  aminothiazole
49
DMF
70 C

| Bromoketone | Title Product | LC-MS |
|---|---|---|
| 10 | 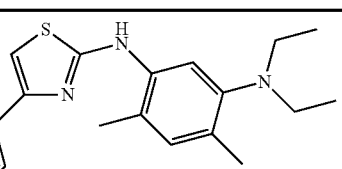<br>81 | observed [M + 1] = 432.3<br>calculated [M + 1] = 432.6 |
| 20 | 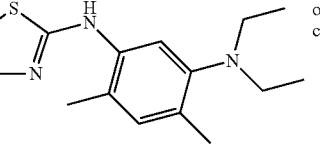<br>82 | observed [M + 1] = 433.4<br>calculated [M + 1] = 433.6 |
| 23 | 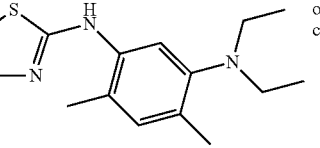<br>83 | observed [M + 1] = 418.4<br>calculated [M + 1] = 418.6 |

Various representative alpha bromoketone derivatives were combined with thiourea derivative 34 in a similar procedure as described above, except that the condensed product (0.1 mmol, 37.5 mg) was subsequently dissolved in 0.5 mL DMF. Potassium carbonate ($K_2CO_3$, 0.2 mmol, 27.6 mg) and bromoethane (0.12 mmol, 13 mg) were added to the solution. The reaction was stirred overnight at room temperature. After removal of the unreacted potassium carbonate, the reaction mixture was purified by reversed phase HPLC using acetonitrile/water/TFA gradient and C18 stationary phase to isolate and then concentrate the title product. Representative bromoketones employed in this reaction and the resultant title compounds afforded are listed below in Table 7.

TABLE 7

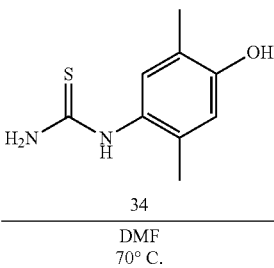

| Bromoketone | Title Product | LC-MS |
|---|---|---|
| 10 | 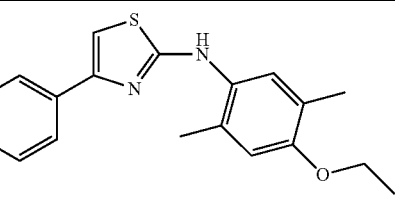<br>84 | observed [M + 1] = 405.4<br>calculated [M + 1] = 405.5 |
| 20 | 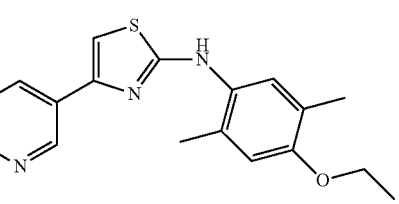<br>85 | observed [M + 1] = 406.4<br>calculated [M + 1] = 406.5 |
| 23 | 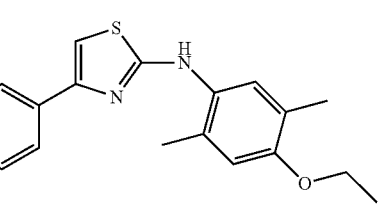<br>86 | observed [M + 1] = 391.4<br>calculated [M + 1] = 391.5 |

Using the similar chemistry described above with different alkyl bromides, 87 was synthesized (observed [M+1]=431.4, calculated [M+1]=431.6).

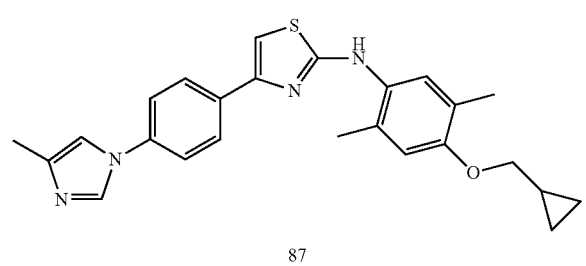

87

Representative thiourea derivatives (see "thiourea" column of Table 8) were combined with 2-bromo-1-(4-(4-methyl-piperazin-1-yl)-phenyl)-ethan-1-one 88 in the preparation of the following representative piperazinyl containing aminothiazole analogs. The following exemplary route was employed to prepare the representative title compounds illustrated in Table 8.

Generally, 0.1 mmol of 2-bromo-1-(4-(4-methyl-piperazin-1-yl)-phenyl)-ethan-1-one was dissolved in 1.0 mL anhydrous N,N-dimethylformamide (DMF) and 0.1 mmol of thiourea was added. The mixture was heated at 70° C. for 4 h with vortexing. After cooling to room temperature, the reaction mixture was directly injected onto a reverse-phase HPLC column using a gradient of 1-99% acetonitrile/water/0.05 TFA over 10 minutes. The desired fraction containing the title compound was concentrated via speedvac. The purity of all title compounds was 95%, as measured by HPLC.

TABLE 8

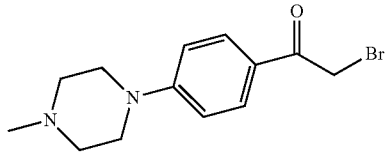

thiourea —88→ aminothiazole
DMF
70° C.

| Thiourea | Title Product | Yield | LC/MS |
|---|---|---|---|
| (3-chlorophenyl)-thiourea | 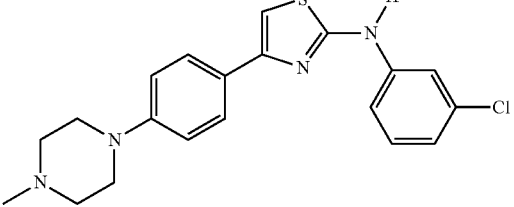<br>89 | 0.024 g = 62% yield | $[M+1]^+ = 385$<br>$C_{20}H_{21}ClN_4S = 384.95$ |
| (2,4-dichlorophenyl)-thiourea | 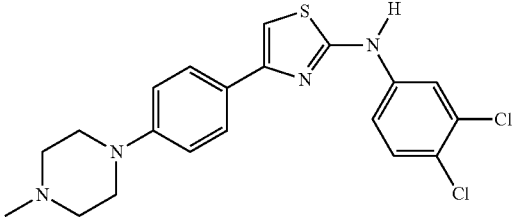<br>90 | 0.028 g = 67 % yield | $[M+1]^+ = 420$<br>$C_{20}H_{20}Cl_2N_4S = 419$ |
| (4-dichlorophenyl)-thiourea | 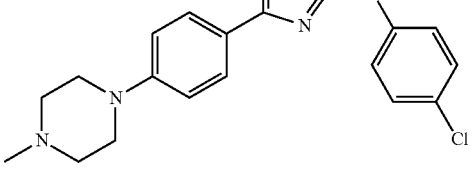<br>91 | 0.028 g = 72% yield | $[M+1]^+ = 385$<br>$C_{20}H_{21}ClN_4S = 384.54$ |
| benzo[1,3]dioxol-5-yl-thiourea | 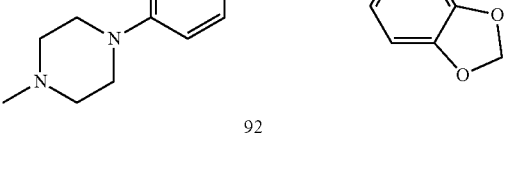<br>92 | 0.024 g = 60% yield. | $[M+1]^+ = 395$<br>$C_{21}H_{22}N_4O_2S = 394.50$ |
| (3-methoxy-phenyl)-thiourea | 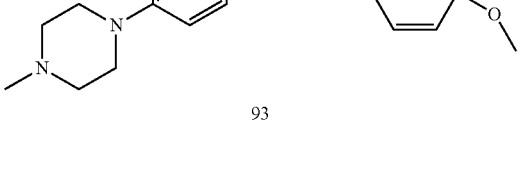<br>93 | 0.034 g = 92% yield. | $[M+1]^+ = 381$<br>$C_{21}H_{24}N_4OS = 380.50$ |

TABLE 8-continued

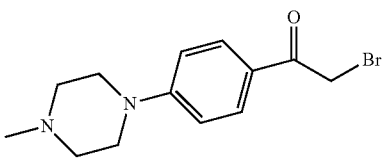

thiourea $\xrightarrow[\text{70° C.}]{\text{88, DMF}}$ aminothiazole

| Thiourea | Title Product | Yield | LC/MS |
|---|---|---|---|
| (2,3-dihydro-benzo[1,4]-dioxin-6-yl)- | 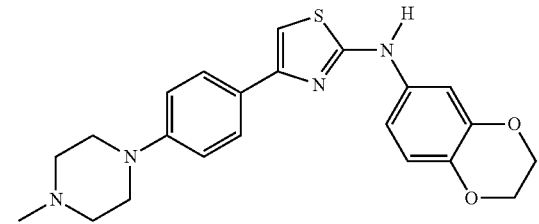<br>94 | 0.026 g = 65% yield. | $[M + 1]^+ = 409$<br>$C_{22}H_{24}N_4O_2S = 408.53.$ |
| (3-methylsulfanyl-phenyl)-thiourea | 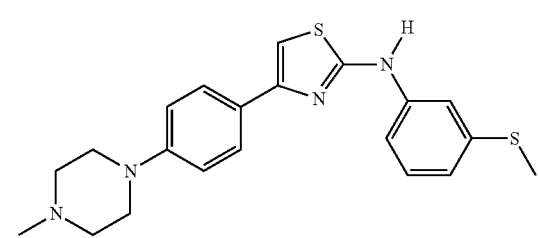<br>95 | 0.033 g = 82% yield. | $[M + 1]^+ = 397$<br>$C_{21}H_{24}N_4S_2 = 396.58$ |
| naphthalen-2-yl- thiourea | 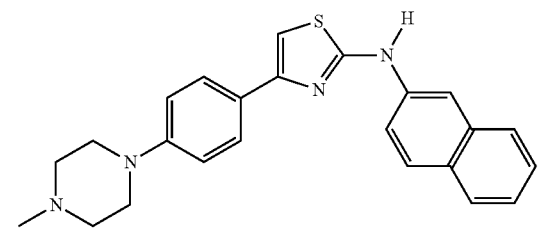<br>96 | 0.038 g = 95% yield | $[M + 1]^+ = 401$<br>$C_{24}H_{24}N_4S = 400.55$ |
| (4-phenoxy-phenyl)-thiourea | 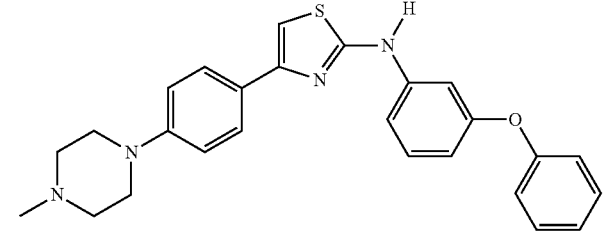<br>97 | 0.026 g = 60% yield | $[M + 1]^+ = 443$<br>$C_{26}H_{26}N_4OS = 442.55$ |

Representative thiourea derivatives (see "thiourea" column of Table 9) were combined with 2-bromo-1-(4-imidazol-1-yl-phenyl)ethan-1-one 22 in the preparation of the following representative imidazolyl containing aminothiazole analogs. The same exemplary procedure as described above was employed to prepare the representative title compounds illustrated in Table 9.

TABLE 9

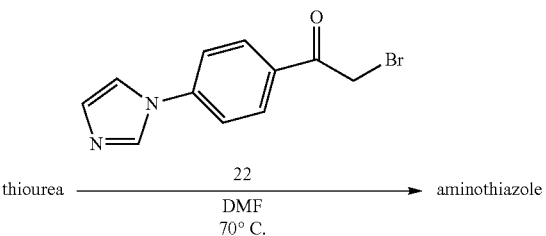

| Thiourea | Title Product | Yield | LC/MS |
|---|---|---|---|
| (3-methyl-sulfanyl-phenyl)-thiourea | 98 | 0.029 g = 80% yield | [M + 1]⁺ = 365 $C_{19}H_{16}N_4S_2$ = 364.49 |
| (3-chloro-phenyl)-thiourea | 99 | 0.021 g = 58% yield | [M + 1]⁺ = 353 $C_{18}H_{13}ClN_4S$ = 352.84 |
| (4-diethylamino-2-methyl-phenyl)-thiourea | 1200 | 0.029 g = 73% yield | [M + 1]⁺ = 404 $C_{23}H_{25}N_5S$ = 403.55 |

Pyrrolidinyl containing analogs were also prepared using a similar procedure as described above. An exemplary pyrrolidinyl analog, compound 1201, was prepared by dissolving 0.1 mmol of 2-bromo-1-(4-pyrrolidin-1-yl-phenyl)ethan-1-one in 1.0 mL anhydrous DMF and adding 0.1 mmol of (3-methylsulfanyl-phenyl)-thiourea. The mixture was heated at 70° C. for 4 h with vortexing. After cooling to room temperature, the reaction mixture was directly injected onto a reverse-phase HPLC column using a gradient of 1-99% acetonitrile/water/0.05 TFA over 10 minutes. The desired fraction was concentrated via speedvac, and the purity of compound 1201 was 95%, as measured by HPLC.

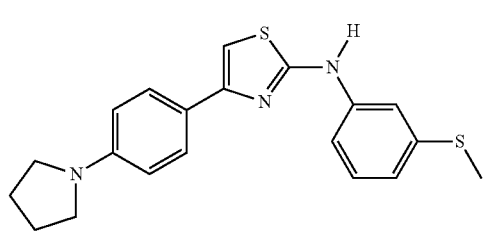

1201

In addition to thiazole containing analogs, oxazolidone containing analogs were also prepared by condensing aryl urea derivatives with bromoketone derivatives, in a similar manner as described above. An exemplary oxazolidone analog, [4-(4-imidazol-1-yl-phenyl)-oxazol-2-yl]-(4-methoxyphenyl)-amine 1202, and exemplary analogs thereof were prepared by the exemplary route depicted below.

In this representative procedure, mixed bromoketone (0.2 g, 0.75 mmol) and urea (0.375 g, 2.26 mmol) were dissolved in 1.5 mL DMF in a sealed glass tube. The mixture was heated at 85-90° C. with stirring for 24 h. After the reaction was cooled to room temperature, the reaction mixture was diluted with DMF and injected directly on a reverse-phase HPLC column using a gradient of 1-99% CH$_3$CN/water/0.05% TFA over 10 min. The desired fraction containing the product was concentrated via speedvac and further purified by precipitation from hexane/EtOAc (1:1) to yield 0.140 g (56%) of compound 1202 as a white solid. Structure was confirmed by $^1$H NMR in DMSO and LC-MS [M+1]=333. Purity, as measured by HPLC, was >95%.

Example 4

Preparation of Representative Thiazoles

A. Addition of cyclic moieties and N-substitution

Various representative N-substituted thiazole containing compounds were prepared by the representative route shown below. Furthermore, this route represents another procedure by which cyclic ring moieties were added to representative thiazole compounds.

In the exemplary route shown below, bromoketone 22 was condensed with 4-bromo-phenyl thiourea to afford 1203 in similar procedures as described in Example 3. Subsequent N-acylation produced 1204, whereas subsequent N-alkylation afforded 1205. Alternatively, heterocyclic rings were further added to 1203 or 1205 to produce 1209 or 1206 and 1207, respectively.

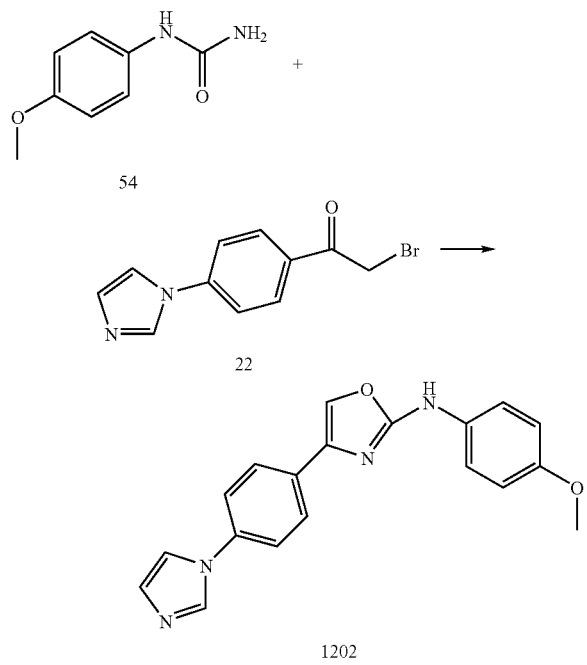

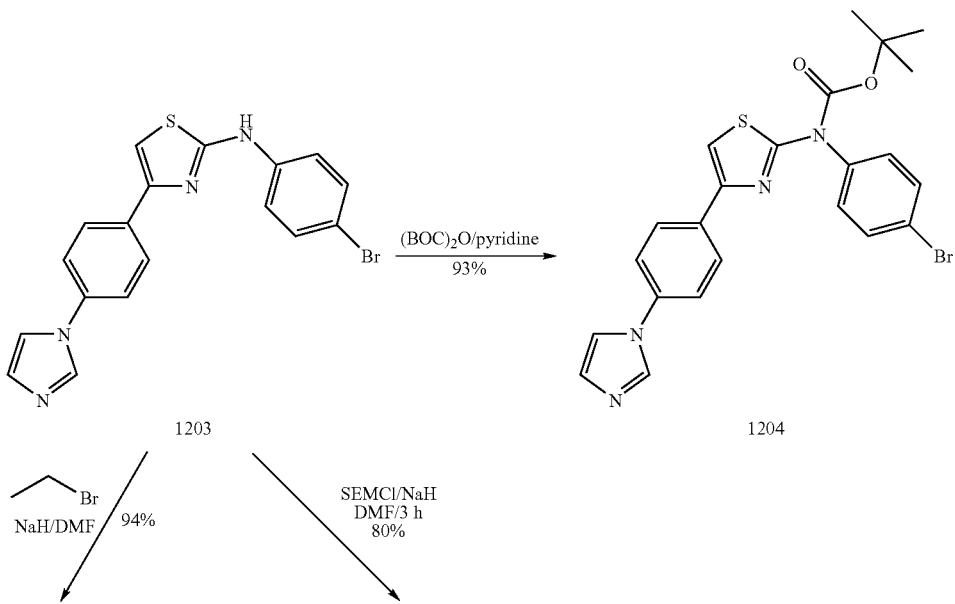

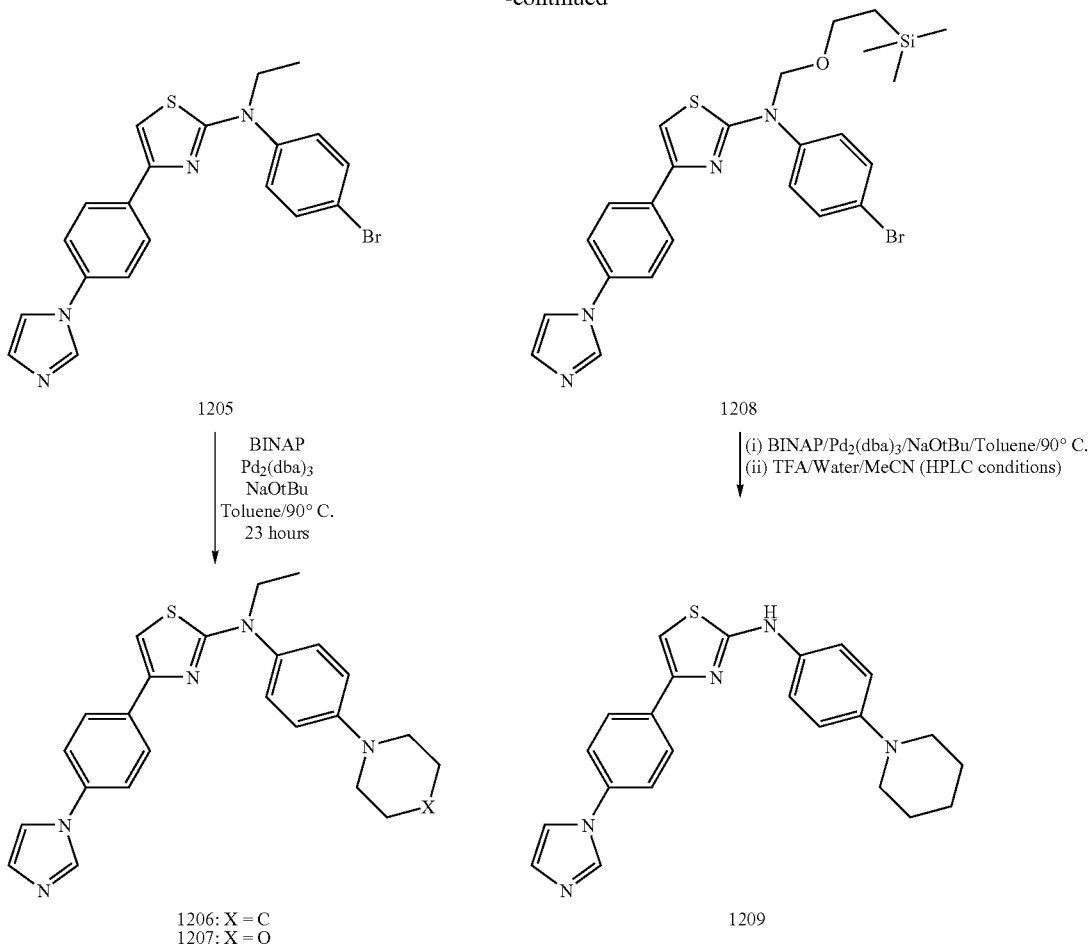

1. (4-bromophenyl)-(4-(4-imidazol-1-ylphenyl)-thiazol-2-yl)-carbamic acid tert-butyl ester (1204)

Compound 1203 (400 mg, 1.0 mmol) was suspended in anhydrous pyridine (5 mL) under an atmosphere of nitrogen before addition of di-tert-butyldicarbonate (262 mg, 1.2 mmol). The reaction mixture was stirred at room temperature for 16 hours (reaction turned clear after 5 minutes) before it was poured onto ice-water. After stirring for 10 minutes, the mixture was filtered and the precipitate was dried in suction for 2 hours. Compound 1204 was isolated as an off-white powder (460 mg). Expected mass spectrometry=497; observed=498 [M+1].

2. 4-bromophenyl-(4-(4-imidazol-1-ylphenyl)-thiazol-2-yl)-(2-trimethylsilanyl-ethoxymethyl)-amine (1208)

Compound 1204 (500 mg, 1.26 mmol) was placed in anhydrous DMF (7 mL) under an atmosphere of nitrogen prior to addition of NaH (35 mg of 95% powder, 1.38 mmol). After stirring at room temperature for 10 minutes, 2-(trimethylsilyl)ethoxymethyl chloride (0.25 mL, 1.38 mmol) was added. The reaction mixture was stirred at room temperature for 3 hours before careful addition of water (50 mL) and EtOAc (3×50 mL). The organic extracts were washed with water (100 mL), brine (100 mL), dried over MgSO$_4$, and filtered. Removal of the solvent in vacuo gave compound 25 as a yellow oil, which solidified upon standing (530 mg). $^1$H NMR (300 MHz, DMSO. δ in ppm) −0.07 (s, 9H), 0.93 (t, J=7.8 Hz, 2H), 3.69 (t, J=7.5 Hz, 2H), 5.32 (s, 2H), 7.11 (s, 1H), 7.44-7.50 (m, 3H), 7.65 (d, J=6.3 Hz, 2H), 7.68 (d, J=5.7 Hz, 2H), 7.78 (d, J=0.9 Hz, 1H), 7.97 (d, J=8.4 Hz, 2H), 8.30 (s, 1H). Expected mass spectrometry=527; observed=528 [M+1].

3. (4-(4-imidazol-1-yl-phenyl)-thiazol-2-yl)-(4-piperidin-1-yl-phenyl)-amine (1209)

In a heat-gun dried vial that was purged with nitrogen, (+/−)-BINAP (10 mg, 0.015 mmol) was dissolved in anhydrous toluene (1 mL). After 2 minutes, Pd$_2$(dba)$_3$ (3 mg, 0.0025 mmol), compound 1208 (53 mg, 0.1 mmol), and piperidine (11 mg, 0.12 mmol) were added to the reaction flask. After stirring at room temperature for 5 minutes, NaOtBu (14 mg, 0.14 mmol) was added and the reaction mixture was heated at 90° C. for 18 hours before passage through a 0.45 μm filter and subsequent HPLC purification. Compound 1209 was isolated as a brown oil (1.3 mg). Expected mass spectrometry=401; observed=402 [M+1].

4. (4-bromophenyl)-ethyl-(4-(imidazol-1-ylphenyl)-thiazol-2-yl)-amine (1205)

Compound 1203 (200 mg, 0.5 mmol) was placed in anhydrous DMF (7 mL) under an atmosphere of nitrogen prior to addition of NaH (17 mg of 95% powder, 0.65 mmol). After

5. N-ethyl-(4-(4-imidazol-1-ylphenyl)-thiazol-2-yl)-(4-piperidin-1-ylphenyl)-amine (1206)

In a heat-gun dried vial that was purged with nitrogen, (+/−)-BINAP (10 mg, 0.015 mmol) was dissolved in anhydrous toluene (1 mL). After 2 minutes, Pd$_2$(dba)$_3$ (3 mg, 0.0025 mmol), compound 1205 (43 mg, 0.1 mmol), and piperidine (11 mg, 0.12 mmol) were added. After stirring at room temperature for 5 minutes, NaOtBu (14 mg, 0.14 mmol) was added and the reaction mixture was heated at 90° C. for 23 hours before passage through a 0.45 μm filter, and subsequent purification by HPLC. Compound 1206 was isolated as a brown oil (12 mg). Expected mass spectrometry=429; observed=430 [M+1].

6. N-ethyl-(4-(4-imidazol-1-yl-phenyl)-thiazol-2-yl)-(4-morpholin-4-yl-phenyl)-amine (1207)

In a heat-gun dried vial that was purged with nitrogen, (+/−)-BINAP (10 mg, 0.015 mmol) was dissolved in anhydrous toluene (1 mL). After 2 minutes, Pd$_2$(dba)$_3$ (3 mg, 0.0025 mmol), compound 1205 (43 mg, 0.1 mmol), and morpholine (11 mg, 0.12 mmol) was added. After stirring at room temperature for 5 minutes, NaOtBu (14 mg, 0.14 mmol) was added and the reaction mixture was heated at 90° C. for 23 hours before it was passed through a 0.45 μm filter, and subsequent purification by HPLC. Compound 1207 was isolated as a brown oil (21 mg). Expected mass spectrometry=431; observed=432 [M+1].

B. Addition of Non-Cyclic Moieties

In addition to cyclic moieties, non-cyclic functionalities were added to representative thiazole compounds after condensation of bromoketone derivatives with thiourea derivatives. As shown in the exemplary route below, thiazole 1208 was N-alkylated to produce 1209. Addition of N,N, diethyl amine resulted in 1210, followed by N-deprotection to give 1211.

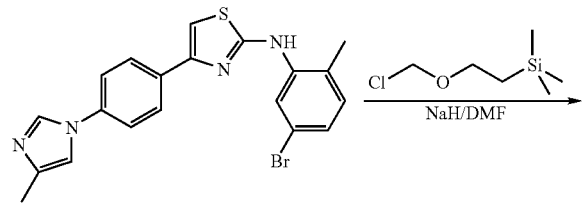

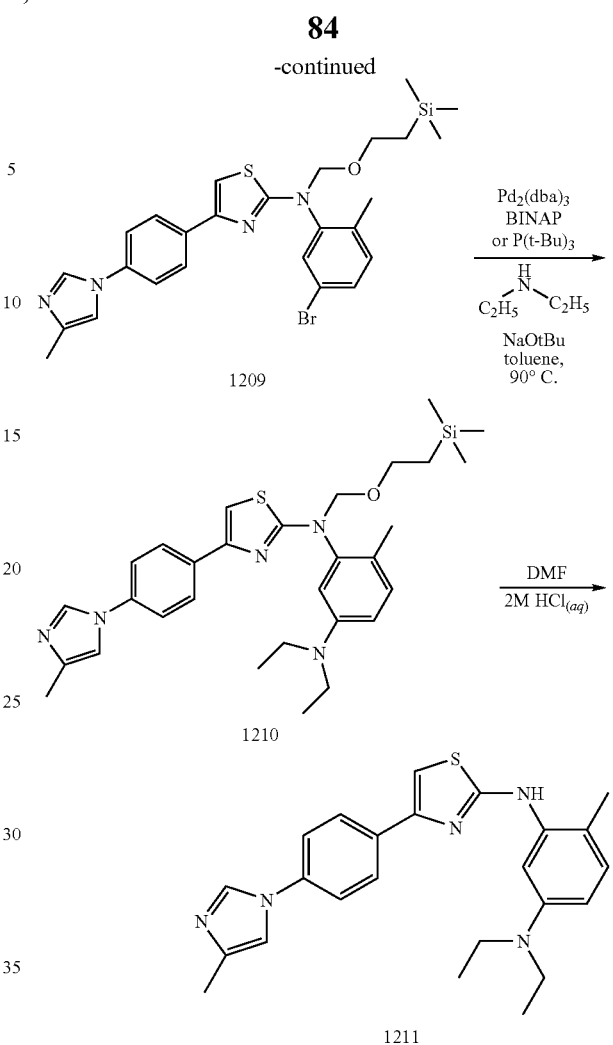

1. N*1,N*1-diethyl-4-methyl-N*-3*-{4-[4-(4-methyl-imidazol-1-yl)-phenyl)-thiazol-2-yl)-N*3*-(2-trimethylsilanyl-ethoxymethyl)-benzene-1,3-diamine (1210)

To a dry screw-capped vial containing a stir bar, tris (dibenzylideneacetone) dipalladium (0) (0.066 g, 0.146 mmol), tri (tert-butyl) phosphine (0.44 ml of a 10% solution in hexanes, 0.146 mmol), a solution of compound 1209 in dry toluene (1.62 in 15 ml toluene, 2.92 mmol), diethylamine (0.90 ml, 8.76 mmol), and sodium tert-butoxide (0.420 g, 4.38 mmol) was added together. The vial was flushed with nitrogen and tightly capped. The mixture was then stirred in an oil bath at 90° C. for 1 hour. The toluene was then removed under reduced pressure. The material was then re-suspended in CH$_2$Cl$_2$ and silica gel. The CH$_2$Cl$_2$ was then removed under reduced pressure to absorb the compound onto the silica gel. The material was then purified by column chromatography and eluted with EtOAc/hexanes to yield product 1210 as a pale yellow semi-solid (0.842 g, 52%). LC/MS: [M+1]$^+$= 548.4. C$_{30}$H$_{41}$N$_5$OSSi=547.8.

2. N*1,N*1-diethyl-4-methyl-N*-3*-{4-[4-(4-methyl-imidazol-1-yl)-phenyl)-thiazol-2-yl)-N*3*-(2-trimethylsilanyl-ethoxymethyl)-benzene-1,3-diamine (1211)

Compound 1210 was dissolved in DMF (5 ml) and aqueous 2 M HCl (5 ml), and stirred at room temperature for 1.5 hours.

The product was then purified by reverse-phase HPLC. Pure fractions were combined and concentrated to dryness under reduced pressure. The resulting material was dissolved in CH$_2$Cl$_2$ (250 ml) and washed 2×saturated NaHCO$_3$ (100 mL) and 1×brine (100 mL). The organic phase was dried over MgSO$_4$, filtered, and concentrated under reduced pressure to yield 1211 as a white solid (free base) (0.610 g, 51%). LC/MS: [M+H]$^+$=418.5. C$_{24}$H$_{27}$C$_5$S=417.5.

3. Dihydrochloride salt of N*1,N*1-diethyl-4-methyl-N*3*-{4-[4-(4-methyl-imidazol-1-yl)-phenyl)-thiazol-2-yl)-N*3*-(2-trimethylsilanyl-ethoxymethyl)-benzene-1,3-diamine Compound 1211 (free base) (0.610 g, 1.46 mmol) was partially dissolved in MeOH (2 ml). 2M HCl/Et$_2$O (1.46 ml, 2.92 mmol) was then added and the solution cleared. The solution was concentrated down to a minimal volume using a stream of nitrogen gas. Et$_2$O (5 ml) was then added and the compound was triturated to a white solid, which was washed with 2×Et$_2$O (5 ml) and dried with a stream of nitrogen. The material was then re-dissolved in dry EtOH (1.5 ml) with gentle heating. The mixture was allowed to cool and the compound crystallized. The crystals were collected on a filter and washed with 2×Et$_2$O (1 ml) and dried in vacuo to yield the dihydrochloride salt as an off-white solid (0.320 g, 26%). LC/MS: [M+1]$^+$=418.5. C$_{24}$H$_{27}$N$_5$S.2HCl=490.5. $^1$H NMR (DMSO-d6) 300 MHz δ1.09-1.36 (6H, t, J=6.9 Hz), 2.34 and 2.36 (6H, two s), 3.51 (4H, broad s), 7.42 (2H, t, J=8.4 Hz), 7.57 (1H, s), 7.79 (2H, d, J=9.0 Hz), 8.07 (1H, t, J=1.2 Hz), 8.19 (2H, d, J=9.0 Hz), 8.57 (1H, s), 9.69 (1H, d, J=1.8 Hz), 9.68 (1H, s).

By using similar procedures with various bromoketone derivatives and thiourea derivatives, a collection of cyclic, non-cyclic, and N-alkylated thiazole containing compounds were synthesized, including representative compound 1212 below, and its dihydrochloride salt (0.032 g, 97%). LC/MS: [M+1]$^+$=433.4. C$_{24}$H$_{28}$N$_6$S.2HCl=505.5. $^1$NMR (DMSO-d6) 300 MHz δ0.856 (3H, t, J=7.2 Hz), 1.07-1.23 (5H, m), 2.35 and 2.38 (6H, two s), 3.43 and 3.54 (4H, two broad s), 7.41 (2H, broad s), 7.73 (1H, s), 8.03 (1H, d, J=9.0 Hz), 8.24 (1H, s), 8.62 (1H, broad s), 8.75 (1H, d, J=8.7 Hz), 9.12 (1H, d, J=1.8 Hz), 9.80 (1H, broad s), 9.90 (1H, d, J=1.5 Hz).

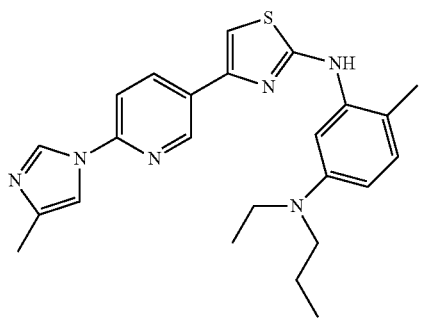

1212

C. Representative C-linked thiazoles

In addition to N-linked thiazoles, various C-linked thiazoles were prepared by the exemplary route shown below.

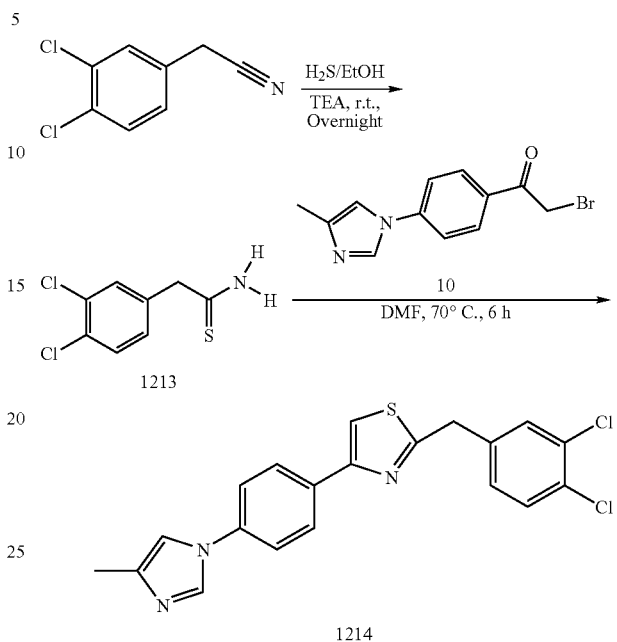

1. 2-(3,4-Dichloro-phenyl)-thioacetamide (1213)

Hydrogen sulfide (gas) was bubbled into a solution of (3,4-dichloro-phenyl)-acetonitrile (1.86 g, 10 mmol, 1.0 eq)) and triethyl amine (10 mmol, 1 eq) in ethanol (10 ml) for about 1 hour. After 1 hour the reaction mixture capped and stirred at room temperature overnight. TLC showed that most of nitrile was converted to thioacteamide. Excess of H$_2$S was removed by bubbling nitrogen into the reaction mixture for 30 min. The reaction mixture was then concentrated and purified by silica gel chromatography (ISCO system, 30-60% ethylacetate/hexane) to give the title compound (1213) (55% yield).

2-(3,4-Dichloro-benzyl)-4-[4-(4-methyl-imidazole-1-yl)-phenyl]-thiazole (1214)

The thioacetamide 1213 (0.08 mmol) and 2-bromo-1-[4-(4-methyl-imidazole-1-yl)-phenyl]-ethanone (0.08 mmol) 10 were dissolved in 1 ml DMF. The reaction was stirred at 70 C for 6 hours. After cooling to room temperature, the reaction mixture was directly injected into a reversed phase HPLC (Gilson 215) using acetonitrile/water/TFA gradient and C18 stationary phase to isolate and then concentrate to give the title product 1214 as a TFA salt.

Example 5

Preparation of Representative Triazolyl and Furanyl Aminothiazole Compounds In the preparation of triazolyl and furanyl containing compounds, the following exemplary general route was employed.

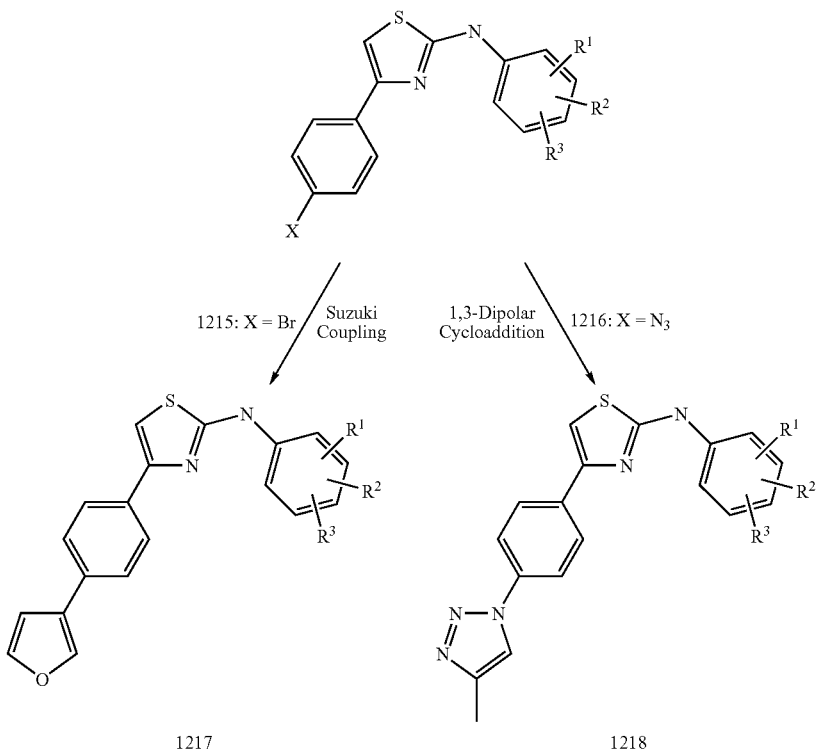

The following route was employed to prepare representative triazolyl aminothiazole compounds.

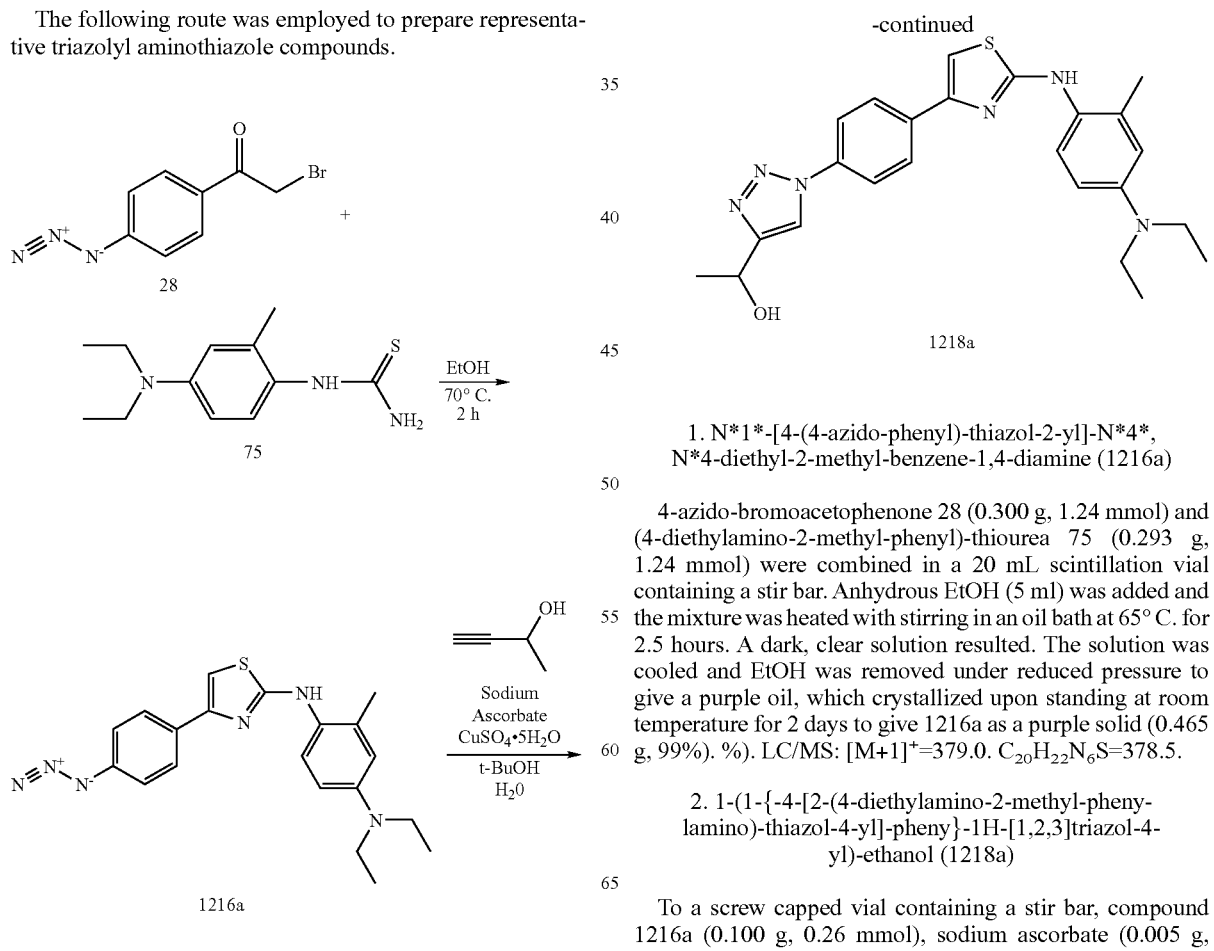

1. N*1*-[4-(4-azido-phenyl)-thiazol-2-yl]-N*4*, N*4-diethyl-2-methyl-benzene-1,4-diamine (1216a)

4-azido-bromoacetophenone 28 (0.300 g, 1.24 mmol) and (4-diethylamino-2-methyl-phenyl)-thiourea 75 (0.293 g, 1.24 mmol) were combined in a 20 mL scintillation vial containing a stir bar. Anhydrous EtOH (5 ml) was added and the mixture was heated with stirring in an oil bath at 65° C. for 2.5 hours. A dark, clear solution resulted. The solution was cooled and EtOH was removed under reduced pressure to give a purple oil, which crystallized upon standing at room temperature for 2 days to give 1216a as a purple solid (0.465 g, 99%). %). LC/MS: [M+1]$^+$=379.0. $C_{20}H_{22}N_6S$=378.5.

2. 1-(1-{-4-[2-(4-diethylamino-2-methyl-phenylamino)-thiazol-4-yl]-pheny}-1H-[1,2,3]triazol-4-yl)-ethanol (1218a)

To a screw capped vial containing a stir bar, compound 1216a (0.100 g, 0.26 mmol), sodium ascorbate (0.005 g, 0.026 mmol), copper (II) sulfate pentahydrate (0.001 g, 0.0026 mmol), and but-3-yn-2-ol (0.018 g, 0.26 mmol) was added. Tert-buty alcohol (1 ml) and water (1 ml) were added to the vial and the vial was capped. The mixture was stirred vigorously for 16 h at room temperature. The solvent was removed under reduced pressure and the resulting residue re-dissolved in DMF (1.5 ml). The product was then isolated by reverse-phase HPLC. The pure fraction was concentrated under reduced pressure to yield 1218a as the ditrfluoroacetate salt (0.038 g, 21%). LC/MS: $[H+1]^+$=449.1 $C_{24}H_{28}N_6OS$=448.5.

The following procedure was used to prepare a representative furanyl aminothiazole compound, N*1*,N*1*-diethyl-N*3*-[4-(4-furan-3-yl-phenyl)-thiazol-2-yl]-4-methyl-benzene-1,3-diamine (1217a).

N*3*-[4-(4-bromo-phenyl)-thiazol-2-yl]-N*1*,N*1*-diethyl-4-meth-benzene-1,3-diamine (104 mg, 0.25 mmol) (1215a) was placed in a flask and toluene:EtOH (4:1, 12 mL:3 mL) were added prior to the addition of 3-furyl boronic acid (34 mg, 0.30 mmol), sodium carbonate (80 mg, 0.75 mmol) and water (1 mL). The reaction mixture was degassed by bubbling nitrogen through it for 30 min. $Pd(PPh_3)_4$ (29 mg, 0.025 mmol) was subsequently added and the reaction mixture was heated at 80° C. for 17 h before it was allowed to cool to room temperature. EtOAc (3×100 mL) and water (100 mL) were added. The organic extracts were washed with water (100 mL), brine (100 mL), dried over $MgSO_4$, filtered, and purified by column chromatography (40 g ISCO cartridge). The title compound was isolated as a yellow powder (40 mg, 40%, mass for $C_{24}H_{25}N_3O_5S$, calculated: 403.5, observed: 404.1 [M+1]).

Example 6

Representative Invention Compounds

Table 10 below illustrates representative compounds which were synthesized using exemplary routes described above in Examples 1-5.

Example 7

ELISA Assay to Assess Aβ Modulation

Compounds were evaluated for activity in modulating Aβ42 and Aβ40 levels in the extracellular medium using the following sandwich ELISA assay.
A. Preparation of cells An APP-expressing neuroblastoma cell line was generated by stably transfecting human SH-SY5Y cells obtained from ATCC (accession no. CRL-2266) with DNA encoding human APP751 contained in vector pcDNA.1. Cells were plated in 384-well plates (~20,000 SH-SY5Y-APP transfected cells per well) and allowed to adhere for at least 18 hours. The cells were then washed in media (DMEM, 10% FBS, 100 units/ml penicillin, 0.1 mg/ml streptomycin), and 30 µl of media was added containing an appropriate concentration of compound.
B. Calculation of potency of compounds Compounds were suspended in DMSO (vehicle). Initial assays to determine whether a compound had activity in reducing Aβ42 level of the extracellular medium were conducted using a single concentration of compound, i.e., 30 µM. Compound was added to cells and the cells were incubated in the presence of compound for 18-22 hours. If the Aβ42 level of the extracellular medium (as assessed by sandwich ELISA described below) of cells contacted with this concentration of a compound was less than about 60% of the level of extracellular medium of cells contacted with vehicle only (negative control), then the compound was assayed at a range of concentrations to determine its potency (i.e. its $IC_{50}$ value) for reduction of Aβ42 levels and Aβ40 levels.

To determine the potency of a compound in reducing Aβ42 level of the extracellular medium, cells were treated with six different concentrations (differing by ½ log dilutions) of compound, and the concentration at which reduction of Aβ42 level was half of the maximum reduction in Aβ42 level was calculated.

Likewise, to determine the potency of a compound in reducing Aβ40 level of the extracellular medium, cells were treated with various concentrations of compound, and the concentration at which reduction of Aβ40 level was half of the maximum reduction in Aβ40 level was calculated.

To determine the degree of selectivity of a compound for reducing Aβ42 level of the extracellular medium relative to reducing Aβ40 level of the extracellular medium, the potency of the compound for reduction of Aβ42 level was compared to the potency of the compound for reduction of Aβ40 level, and expressed as fold selectivity. If the Aβ40 level of the extracellular medium was not reduced greater than 50%, the highest concentration of compound tested (e.g., 30 µM) was used in the calculation.
C. ELISA assay to assess Aβ levels Aβ levels of the extracellular medium were assessed by sandwich ELISA assays of supernatant from the wells of the tissue culture dish using Aβ42- or Aβ40-selective antibodies as capture antibodies. Prior to running the immunoassays, white microtiter 384-well plates were coated overnight with 25 µl of ~5 µg/ml solution of either Aβ42- or Aβ40-selective monoclonal antibody in TBS.

For assessing Aβ42 levels in the supernatant of a sample, the Aβ42-selective monoclonal antibody A387, raised against amino acids 35-42 of Aβ (see WO 04/018997) was used in the first reaction in the sandwich assay (primary or capture antibody). For assessing Aβ40 levels in the supernatant of cells, the Aβ40-selective monoclonal antibody B113, which recognizes amino acids 30-40 of Aβ(see WO 04/018997) was used in the first reaction of the sandwich assay.

The secondary antibody used in the sandwich assay, B436 which was raised against amino acids 1-12 of Aβ (see WO 04/018997), is reactive with both $Aβ_{40}$ and $Aβ_{42}$ peptides. The secondary antibody, which was used as the detection antibody, was conjugated to alkaline phosphatase, and the presence or absence of antibody binding was determined by luminescence of a substrate that emits light in the presence of alkaline phosphatase, i.e., CDP-Star chemiluminescence substrate (Applied Biosciences).

Following overnight coating with the capture antibody at 4° C., the assay plates were blocked with 50 µl of 1% BSA/TBS, Fraction V (Sigma, St. Louis, Mo.). Assay plates containing cells were washed three times with 50 µl of TBS/0.1% Tween-20, and then supernatant from the wells of the tissue culture plates was transferred to the antibody-coated plates (20 µl of supernatant was added to plates coated with Aβ42-selective antibody, and 10 µl of supernatant was added to plates coated with Aβ40-selective antibody). The assay plates were incubated with cell supernatant for 2 hours at room temperature. Plates were then washed three times with 50 µi of TBS/0.1% Tween-20. After washing, wells were incubated with 25 µl of anti-$Aβ_{1-12}$ conjugated to alkaline phosphatase (~0.5 µg/ml in 1% TBS) for 2.5 hours at room temperature. Wells were washed three times with 50 µl of TBS/0.1% Tween-20 and 25 µl of CDP-Star chemiluminescence substrate (i, Inc.) was added and incubated for 20 minutes at room temperature. Luminescence was quantified on an Analyst HT (Molecular Devices Corp.).

The data showed acceptable signal to background (~7-20 fold) with the positive control wells clearly distinguishable from the vehicle controls. The assay for Aβ42 peptide had a large linear range, about 75-2000 pg/well, high dynamic range, about 3-30 fold over background in linear range (signal:background), low sensitivity limit, less than about 20 pg/well, and selectivity for Aβ42, at least about 1000-fold selectivity for $A\beta_{42}$ over other Aβ peptides, making the method highly amenable to high-throughput screening for compounds that modulate Aβ42 levels.

Table 11 below shows representative compounds provided herein that show activity in the above described in vitro assays for Aβ42- and/or Aβ40-lowering activity. Potency data for the representative compounds are denoted as follows: A=<0.2 μM; B=0.2 μM-1.0 μM; C=1.1 μM-5.0 μM; D=5.1 μM-10 μM; E=10.1 μM-30 μM; F=detectable Aβ40-lowering activity at a concentration of about 30 μM.

Table 12 further illustrates representative compounds provided herein that show Aβ42- and/or Aβ40-lowering activity at a concentration of about 30 μM.

Example 8

Assessment of Compound Cytotoxicity

To assess compound cytotoxicity, supernatant of cells treated with compound, as described in Example 7 above, was removed, and a solution containing 10% by volume of the cell viability indicator dye AlamarBlue™ (Biosource, San Diego) was added. Cells were incubated for 3 h at 37° C., after which fluorescence was read on a CytoFluor (Applied Biosystems) spectrophotometer, using a 530-nm excitation filter and 580-nm emission filter. Cells treated with compounds shown in Table 11 exhibited less than 40% decrease in AlamarBlue fluorescence relative to control cells.

Example 9

FRET Assay to Assess Aβ Modulation

Compounds were evaluated for activity in modulating Aβ42 and Aβ40 levels in the extracellular medium using a homogeneous time-resolved fluorescence (HTRF) assay as follows.

SH-SY5Y-APP cells were plated and treated with compounds as described in the above Example, except that to determine compound potency, cells were treated with 11 different concentrations of compound, in quarter-log intervals, typically with a maximum concentration of 1, 3 or 10 μM. For the HTRF assay, either 5 or 10 μl of supernatant from treated cells was added to 10 or 15 μl of labeled antibody pairs, for a total volume of 20 μl, and incubated for 20-24 hours at 4° C. The labeled antibody pairs were either 8000 pg B436-XL665 and 400 pg B113 Europium, for assessing Aβ40 levels, or 8000 pg B436-XL665 and 400 pg A387 Europium, for assessing Aβ42 levels, diluted in 50 mM NaPO4, 0.2% BSA, 0.5M KF, pH 7. The fluorescence was read on a BMG Rubystar at 620 nm and 665 nm. To prepare a concentration response curve, the ratio of the reading at 665/620 nm for each concentration was determined and plotted as a percentage of the reading of untreated cells, and the concentration at which reduction of Aβ42 or Aβ40 level was half of the maximum reduction was calculated as the compound potency.

The invention illustratively described herein may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other documents.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

Other embodiments are set forth within the following claims.

What is claimed is:

1. A compound having a structure corresponding to Formula (I):

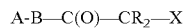

(I)

wherein A is:

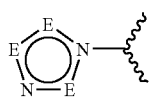

wherein each E is independently CR¹; and
each R¹ is independently hydrogen, halogen, substituted or unsubstituted alkyl, substituted or unsubstituted alkenyl, substituted or unsubstituted alkynyl, substituted or unsubstituted alkoxy, substituted or unsubstituted alkylamido, substituted or unsubstituted alkylamino, substituted or unsubstituted amino, substituted or unsubstituted cycloalkyl, or substituted or unsubstituted aryl;

B is

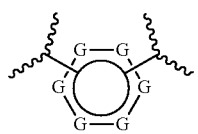

wherein each G is independently CR²; and
wherein each R² is independently selected from hydrogen, halogen, substituted or unsubstituted alkyl, substituted or unsubstituted alkenyl, substituted or unsubstituted alkynyl, substituted or unsubstituted alkoxy, substituted or unsubstituted alkylamido, substituted or unsubstituted alkylamino, substituted or unsubstituted amino, provided that at least one R² is halogen or substituted or unsubstituted alkoxy;
each R is independently hydrogen, substituted or unsubstituted alkyl, substituted or unsubstituted alkenyl, substituted or unsubstituted alkynyl, substituted or unsubstituted alkoxy, substituted or unsubstituted alkylamido, substituted or unsubstituted alkylamino, substituted or unsubstituted cycloalkyl, or substituted or unsubstituted aryl; and
X is halogen.

2. A compound according to claim 1 having the structure:

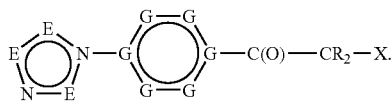

3. A compound according to claim 1 having the structure:

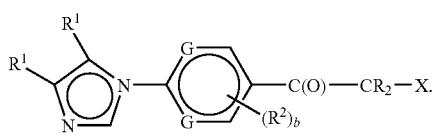

4. A compound according to claim 1 wherein A is unsubstituted imidazolyl.

5. A compound according to claim 1 wherein A is a substituted imidazolyl.

6. A compound according to claim 5 wherein A is a 4-substituted imidazolyl.

7. A compound according to claim 5 wherein said imidazolyl is alkyl substituted.

8. A compound according to claim 5 wherein said imidazolyl is $C_1$-$C_5$ alkyl substituted.

9. A compound according to claim 8 wherein said imidazolyl is methyl substituted.

10. A compound according to claim 8 wherein said imidazolyl is ethyl substituted.

11. A compound according to claim 5 wherein said imidazolyl is halogen substituted.

12. A compound according to claim 11 wherein said imidazolyl is chloro-substituted.

13. A compound according to claim 11 wherein said imidazolyl is bromo-substituted.

14. A compound according to claim 1 wherein at least one R² is a halogen.

15. A compound according to claim 14 wherein said halogen is fluorine.

16. A compound according to claim 1 wherein at least one R² is optionally substituted alkoxy.

17. A compound according to claim 1 wherein at least one R is hydrogen.

18. A compound according to claim 1 wherein each R is hydrogen.

19. A compound according to claim 1 wherein X is chlorine.

20. A compound according to claim 1 wherein X is bromine.

21. A compound according to claim 1 wherein X is iodine.

22. A compound according to claim 1 having a structure selected from the group consisting of:

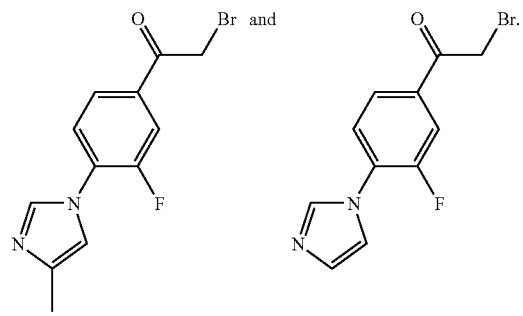

23. A method of making a compound according to claim 1, said method comprising:
    contacting an acetylphenyl-boronic acid with an optionally substituted imidazole in a suitable solvent under conditions suitable to form an imidazolyl phenyl ketone, and thereafter
    contacting said imidazolyl phenyl ketone with bromine under conditions suitable to form a compound of Formula (I).

24. A method of making a compound according to claim 1, said method comprising:
    contacting a 4-fluorophenyl-alkanone with an optionally substituted imidazole in a suitable solvent under conditions suitable to form an imidazolyl phenyl ketone, and thereafter
    contacting said imidazolyl phenyl ketone with bromine under conditions suitable to form a compound of Formula (I).

25. A method of making a compound according to claim 1, said method comprising:

contacting a 3,4-difluorophenyl-alkanone with an optionally substituted imidazole in a suitable solvent under conditions suitable to form an imidazolyl fluorophenyl ketone, and thereafter contacting said imidazolyl fluorophenyl ketone with bromine under conditions suitable to form a compound of Formula (I).

\* \* \* \* \*